(12) United States Patent
Bremer et al.

(10) Patent No.: US 11,667,841 B2
(45) Date of Patent: Jun. 6, 2023

(54) DIBENZOFURAN AND DIBENZOTHIOPHENE DERIVATIVES

(71) Applicant: MERCK PATENT GMBH, Darmstadt (DE)

(72) Inventors: Matthias Bremer, Darmstadt (DE); Constanze Brocke, Gross-Gerau (DE); Atsutaka Manabe, Bensheim (DE); Sven Laut, Weiterstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 91 days.

(21) Appl. No.: 17/289,396

(22) PCT Filed: Oct. 28, 2019

(86) PCT No.: PCT/EP2019/079337
§ 371 (c)(1),
(2) Date: Apr. 28, 2021

(87) PCT Pub. No.: WO2020/089140
PCT Pub. Date: May 7, 2020

(65) Prior Publication Data
US 2021/0403810 A1 Dec. 30, 2021

(30) Foreign Application Priority Data

Oct. 31, 2018 (EP) .................................... 18203594
Dec. 19, 2018 (EP) .................................... 18214085

(51) Int. Cl.
G02F 1/1333 (2006.01)
C09K 19/34 (2006.01)
C07D 307/91 (2006.01)
C07D 333/76 (2006.01)

(52) U.S. Cl.
CPC ........ C09K 19/3405 (2013.01); C07D 307/91 (2013.01); C07D 333/76 (2013.01); C09K 19/3494 (2013.01); C09K 2019/3408 (2013.01)

(58) Field of Classification Search
CPC ............ C09K 19/3405; C09K 19/3494; C09K 19/3408; C09K 19/34; C09K 19/3491; G02F 1/1333; C07D 307/91; C07D 333/76
See application file for complete search history.

(56) References Cited

U.S. PATENT DOCUMENTS

| | | | | |
|---|---|---|---|---|
| 7,514,127 | B2 * | 4/2009 | Lietzau | C09K 19/32 570/183 |
| 10,017,695 | B2 * | 7/2018 | Lietzau | C09K 19/3491 |
| 11,236,063 | B2 * | 2/2022 | Lietzau | C07D 307/91 |
| 2017/0292072 | A1 | 10/2017 | Manabe | |
| 2021/0403810 | A1 * | 12/2021 | Bremer | C09K 19/3405 |

FOREIGN PATENT DOCUMENTS

DE 102005012585 A1 11/2005
EP 3228681 A1 10/2017

OTHER PUBLICATIONS

International Search Report for PCT/EP2019/079337 dated Jan. 21, 2020.
Herzke, D. et al., "Physical-Chemical Properties of Polyfluorinated Dibenzo-p-dioxins and Dibenzofurans," Organohalogen Compounds, 1999, vol. 41, pp. 171-174.
Itoh, T. et al., "A General Palladium-Catalyzed Coupling of Aryl Bromides/Triflates and Thiols," Organic Letters, 2004, vol. 6, No. 24, pp. 4587-4590.
Jepsen T. H. et al., "Synthesis of Functionalized Dibenzothiophenes—An Efficient Three-Step Approach Based on Pd-Catalyzed C—C and C—S Bond Formations," Eur. J. Org. Chem., 2011, pp. 53-57.
English Abstract of DE-10 2005 012585, Publication Date: Nov. 3, 2005.

* cited by examiner

*Primary Examiner* — Geraldina Visconti
(74) *Attorney, Agent, or Firm* — Millen, White, Zelano and Branigan, P.C.; Harry B. Shubin

(57) ABSTRACT

The present invention relates to a compound of the general formula I

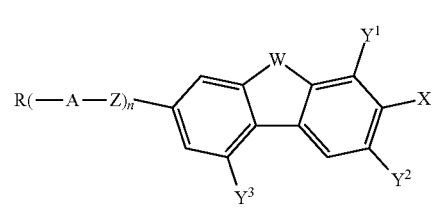

in which the occurring groups and parameters have the meanings indicated in claim 1, to the use thereof in liquid-crystalline or mesogenic media and to liquid-crystalline or mesogenic media comprising these derivatives.

10 Claims, No Drawings

DIBENZOFURAN AND DIBENZOTHIOPHENE DERIVATIVES

The present invention relates to dibenzofuran and dibenzothiophene derivatives, to the use thereof in liquid crystalline media and to liquid crystalline media comprising the dibenzofuran and dibenzothiophene derivatives.

Liquid crystals have found widespread use since the first commercially usable liquid-crystalline compounds were found about 30 years ago. Known areas of application are, in particular, displays for watches and pocket calculators, and large display panels as used in railway stations, airports and sports arenas. Further areas of application are displays of portable computers and navigation systems and video applications. For the last-mentioned applications in particular, high demands are made of the response times and contrast of the images.

The spatial arrangement of the molecules in a liquid crystal has the effect that many of its properties are direction-dependent. Of particular importance for use in liquid-crystal displays are the optical, dielectric and elasto-mechanical anisotropies. Depending on whether the molecules are oriented with their longitudinal axes perpendicular or parallel to the two plates of a capacitor, the latter has a different capacitance; in other words, the dielectric constant ε of the liquid-crystalline medium has different values for the two orientations. Substances whose dielectric constant is larger when the longitudinal axes of the molecules are oriented perpendicular to the capacitor plates than when they are oriented parallel are known as being dielectrically positive. Most liquid crystals used in conventional displays fall into this group.

Both the polarisability of the molecule and the permanent dipole moment play a role for the dielectric anisotropy. On application of a voltage to the display, the longitudinal axis of the molecules orients itself in such a way that the larger of the dielectric constants becomes effective. The strength of the interaction with the electric field depends on the difference between the two constants. In the case of small differences, higher switching voltages are necessary than in the case of large differences. The introduction of suitable polar groups, such as, for example, nitrile groups or fluorine, into the liquid-crystal molecules enables a broad range of working voltages to be achieved.

In the case of the liquid-crystalline molecules used in conventional liquid-crystal displays, the dipole moment oriented along the longitudinal axis of the molecules is larger than the dipole moment oriented perpendicular to the longitudinal axis of the molecules. The orientation of the larger dipole moment along the longitudinal axis of the molecule also determines the orientation of the molecule in a liquid-crystal display in the field-free state. In the most widespread TN ("twisted nematic") cells, a liquid-crystalline layer with a thickness of only from about 5 to 10 μm is arranged between two flat glass plates, onto each of which an electrically conductive, transparent layer of tin oxide or indium tin oxide has been vapour-deposited as electrode. A likewise transparent alignment layer, usually consisting of a polymer (for example polyimides), is located between these films and the liquid-crystalline layer. This alignment layer serves to bring the longitudinal axes of the adjacent crystalline molecules into a preferential direction through surface forces in such a way that, in the voltage-free state, they lie uniformly on the inside of the display surface with the same alignment in a flat manner or with the same small tilt angle. Two polarisation films which only enable linear-polarised light to enter and escape are adhesively bonded to the outside of the display in a certain arrangement.

By means of liquid crystals in which the larger dipole moment is oriented parallel to the longitudinal axis of the molecule, very high-performance displays have already been developed. In most cases here, mixtures of from 5 to 20 components are used in order to achieve a sufficiently broad temperature range of the mesophase and short response times and low threshold voltages. However, difficulties are still caused by the strong viewing-angle dependence in liquid-crystal displays as are used, for example, for laptops. The best imaging quality can be achieved if the surface of the display is perpendicular to the viewing direction of the observer. If the display is tilted relative to the observation direction, the imaging quality drops drastically under certain circumstances. For greater comfort, attempts are being made to make the angle through which the display can be tilted from the viewing direction of an observer as large as possible. Attempts have recently been made to improve the viewing-angle dependence using liquid-crystalline compounds whose dipole moment perpendicular to the longitudinal axis of the molecules is larger than that parallel to the longitudinal axis of the molecule. In the field-free state, these molecules are oriented perpendicular to the glass surface of the display. In this way, it has been possible to achieve an improvement in the viewing-angle dependence. Displays of this type are known as VA-TFT ("vertically aligned") displays.

Also known are so-called IPS ("in-plane switching") displays, which contain an LC layer between two substrates with planar orientation, where the two electrodes are arranged on only one of the two substrates and preferably have interdigitated, comb-shaped structures. On application of a voltage to the electrodes an electric field with a significant component parallel to the LC layer is generated between them. This causes realignment of the LC molecules in the layer plane. Furthermore, so-called FFS ("fringe-field switching") displays have been reported (see, inter alia, S. H. Jung et al., Jpn. J. Appl. Phys., Volume 43, No. 3, 2004, 1028), which contain two electrodes on the same substrate, one of which is structured in a comb-shaped manner and the other is unstructured. A strong, so-called "fringe field" is thereby generated, i.e. a strong electric field close to the edge of the electrodes, and, throughout the cell, an electric field which has both a strong vertical component and also a strong horizontal component. FFS displays have a low viewing-angle dependence of the contrast FFS displays usually contain an LC medium with positive dielectric anisotropy, and an alignment layer, usually of polyimide, which provides planar alignment to the molecules of the LC medium.

In DE 102005012585 A1, dibenzofuran and dibenzothiophene derivatives are proposed for the use in liquid-crystal media. However, due to their substitution pattern, the compounds described therein exhibit negative dielectric anisotropy which makes them unsuitable for the application according to the present invention.

Development in the area of liquid-crystalline materials is far from complete. In order to improve the properties of liquid-crystalline display elements, attempts are constantly being made to develop novel compounds which enable such displays to be optimised.

An object of the present invention was to provide compounds having advantageous properties for use in liquid-crystalline media.

This object is achieved in accordance with the invention by compounds of the general formula I

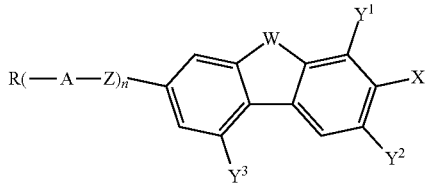

in which
W denotes O or S,
R denotes H, an alkyl radical having 1 to 15 C atoms, wherein one or more $CH_2$ groups in these radicals may each be replaced, independently of one another, by —C≡C—, —$CF_2$O—, —O$CF_2$—, —CH=CH—,

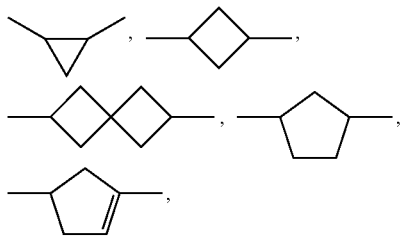

—O—, —CO—O— or —O—CO— in such a way that O atoms are not linked directly to one another, and in which one or more H atoms may be replaced by halogen,
A on each occurrence, identically or differently, denotes a radical selected from the following groups:
  a) the group consisting of trans-1,4-cyclohexylene, 1,4-cyclohexenylene, and decaline-2,6-diyl, in which one or more non-adjacent $CH_2$ groups may be replaced by —O— and/or —S— and in which one or more H atoms may be replaced by F,
  b) the group consisting of 1,4-phenylene and 2,6-naphthylene, in which one or two CH groups may be replaced by N and in which, in addition, one or more H atoms may be replaced by L,
  c) the group consisting of 1,3-dioxane-2,5-diyl, tetrahydrofuran-2,5-diyl, cyclobutane-1,3-diyl, thiophene-2,5-diyl, selenophene-2,5-diyl, and 1,2,3,4-tetrahydronanaphthaline-2,6-diyl, each of which may be mono- or polysubstituted by L,
  d) the group consisting of bicyclo[1.1.1]pentane-1,3-diyl, bicyclo[2.2.2]octane-1,4-diyl, and spiro[3.3]heptane-2,6-diyl, in which one or more H atoms may be replaced by F,
L each, identically or differently, denote halogen, cyano, alkyl, alkoxy, alkylcarbonyl or alkoxycarbonyl group with 1 to 7 C atoms, wherein one or more H atoms may be substituted by F or Cl,
Z on each occurrence, identically or differently, denotes a single bond, —$CF_2$O—, —O$CF_2$—, —$CH_2CH_2$—, —$CF_2CF_2$—, —C(O)O—, —OC(O)—, —$CH_2$O—, —O$CH_2$—, —CF=CH—, —CH=CF—, —CF=CF—, —CH=CH— or —C≡C—, $Y^1$, $Y^2$ and $Y^3$ identically or differently, denote H, F, Cl, $CF_3$, or $CHF_2$, wherein one of $Y^1$ and $Y^2$ is not H,
X denotes F, Cl, CN, NCS, $SF_5$, fluorinated alkyl, alkoxy, alkenyl or alkenyloxy each having up to 5 C atoms, preferably F, $CF_3$, $OCF_3$ or NCS, and
n is 0, 1 or 2, preferably 0 or 1.

A further object of the present invention is to provide liquid-crystalline media, in particular for use in TN, IPS or FFS displays.

This object is achieved in accordance with the invention by the provision of compounds of formula I with positive dielectric anisotropy (Δε).

The compounds of formula I are distinguished by a surprisingly large positive dielectric anisotropy (Δε) and are therefore suitable, in particular, for use in TN-TFT displays, and in IPS- and FFS displays. The compounds have a comparatively very low melting point, a high clearing point and they exhibit very good compatibility with the conventional substances used in liquid-crystal mixtures for displays and are well soluble in such media.

The compounds according to the invention preferably have a Δε of >9, preferably of >15 and particularly preferably a Δε of >20.

If R or L are an alkyl radical and/or an alkoxy radical, this can be straight-chain or branched. It is preferably straight-chain, has 2, 3, 4, 5, 6 or 7 carbon atoms and accordingly is preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

R or L may each, independently of one another, be an alkenyl radical having from 2 to 15 carbon atoms, which may be straight-chain or branched. It is preferably straight-chain and has from 2 to 7 carbon atoms. Accordingly, it is preferably vinyl, prop-1- or -2-enyl, but-1-, -2- or -3-enyl, pent-1-, -2-, -3- or -4-enyl, hex-1-, -2-, -3-, -4- or -5-enyl, or hept-1-, -2-, -3-, -4-, -5- or -6-enyl.

R or L may each, independently of one another, be oxaalkyl, preferably straight-chain 2-oxapropyl (=methoxymethyl), 2-oxabutyl (=ethoxymethyl) or 3-oxabutyl (=methoxyethyl), 2-, 3- or 4-oxapentyl, 2-, 3-, 4- or 5-oxahexyl, or 2-, 3-, 4-, 5- or 6-oxaheptyl.

R or L may each, independently of one another, be an alkyl radical having from 1 to 15 carbon atoms in which one $CH_2$ group has been replaced by —O— and one has been replaced by —CO—, where these are preferably adjacent. This thus contains an acyloxy group —CO—O— or an oxycarbonyl group —O—CO. This is preferably straight-chain and has from 2 to 6 carbon atoms.

R or L may each, independently of one another, be an alkyl radical having from 1 to 15 carbon atoms in which one $CH_2$ group has been replaced by unsubstituted or substituted —CH=CH— and an adjacent $CH_2$ group has been replaced by CO or CO—O or O—CO, where this may be straight-chain or branched. It is preferably straight-chain and has from 4 to 13 carbon atoms.

R or L may each, independently of one another, be an alkyl radical having from 1 to 15 carbon atoms or alkenyl radical having from 2 to 15 carbon atoms, each of which is monosubstituted by —CN or —$CF_3$ and is preferably straight-chain. The substitution by —CN or —$CF_3$ is possible in any desired position.

R or L may each, independently of one another, be an alkyl radical in which two or more $CH_2$ groups have been replaced by —O— and/or —CO—O—, where this may be straight-chain or branched. It is preferably branched and has from 3 to 12 carbon atoms.

R or L may each, independently of one another, be an alkyl radical having from 1 to 15 carbon atoms or an alkenyl radical having from 2 to 15 carbon atoms, each of which is at least monosubstituted by halogen, where these radicals are preferably straight-chain and halogen is preferably —F or —Cl. In the case of polysubstitution, halogen is preferably —F. The resultant radicals also include perfluorinated radicals, such as —CF$_3$. In the case of monosubstitution, the fluorine or chlorine substituent can be in any desired position, but is preferably in the w-position.

The term "fluorinated alkyl radical" preferably encompasses mono- or polyfluorinated radicals. Perfluorinated radicals are included. Particular preference is given to CF$_3$, CH$_2$CF$_3$, CH$_2$CHF$_2$, CHF$_2$, CH$_2$F, CHFCF$_3$ and CF$_2$CHFCF$_3$.

The term "fluorinated alkoxy radical" preferably encompasses mono- or polyfluorinated radicals. Perfluorinated radicals are included. Particular preference is given to OCF$_3$.

In a preferred embodiment of the present invention the compounds of formula I are selected from the compounds of the formulae I-1 to I-6:

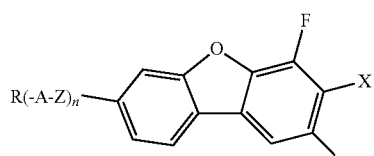

I-1

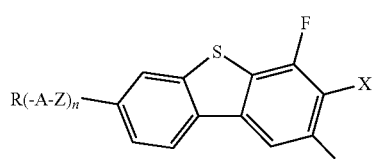

I-2

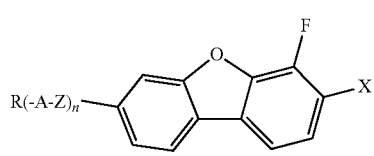

I-3

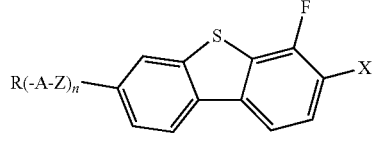

I-4

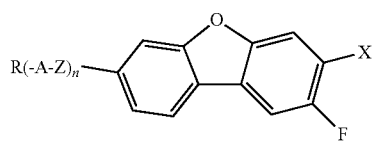

I-5

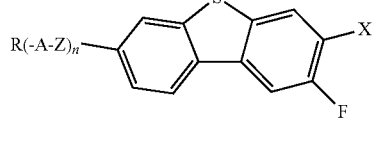

I-6 in which the occurring groups and parameters have the meanings given above for formula I and preferably R denotes H, an alkyl or alkoxy radical each having 1 to 7 C atoms, wherein one or more CH$_2$ groups in these radicals may each be replaced, independently of one another, by

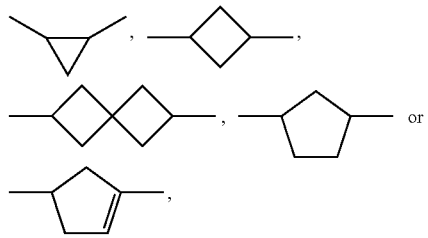

A denotes trans-1,4-cyclohexylene, 1,4-cyclohex-1-enylene, or 1,4-phenylene, in which one or two CH groups may be replaced by N and in which, in addition, one or more H atoms may be replaced by L, L denotes F or Cl, Z on each occurrence, identically or differently, denotes a single bond, —CH$_2$CH$_2$—, —CF$_2$CF$_2$—, —CH$_2$O—, or —C≡C—, preferably a single bond, X denotes F, CF$_3$, OCF$_3$ or NCS, n is 0 or 1.

In a preferred embodiment of the present invention, in the formula I and its sub-formulae I-1, I-2, I-3, I-4, I-5 and I-6, R denotes alkoxy having 1 to 7 C atoms, in particular methoxy, ethoxy, n-propoxy, n-butoxy or n-pentoxy, and n is 0, where the other groups have the meanings given above.

In a preferred embodiment of the present invention, in the formula I and its sub-formulae I-1, I-2, I-3, I-4, I-5 and I-6, n is 1, Z denotes a single bond, and A denotes 4-alkylcyclohexen-1-yl in which alkyl denotes straight chain alkyl having 1 to 7 C atoms, and where the other groups have the meanings given above.

The compounds of the general formula I are prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and are suitable for the said reactions. Use can be made here of variants which are known per se, but are not mentioned here in greater detail.

If desired, the starting materials can also be formed in situ by not isolating them from the reaction mixture, but instead immediately converting them further into the compounds of the general formula I.

Preferred synthetic pathways towards compounds according to the invention are shown in the schemes below and are further illustrated by means of the working examples. The syntheses can be adapted to the particular desired compounds of the general formula I by choice of suitable starting materials.

The dibenzofuran derivatives, i.e. the compounds of formula I wherein W denotes O (formula I') are preferably synthesized as shown in scheme 1 and are obtainable by intramolecular substitution of fluorine by nucleophilic attack of a phenolate by treatment of the phenol P with a base.

Scheme 1

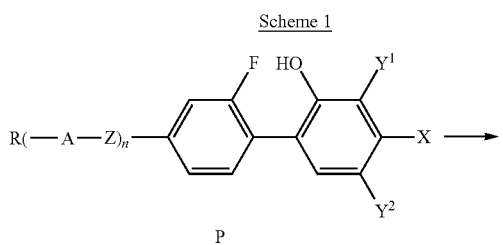

Alternatively, the analogous ring closure where the position of the OH group and the fluorine atom are interchanged, is possible as shown in scheme 2.

Scheme 2

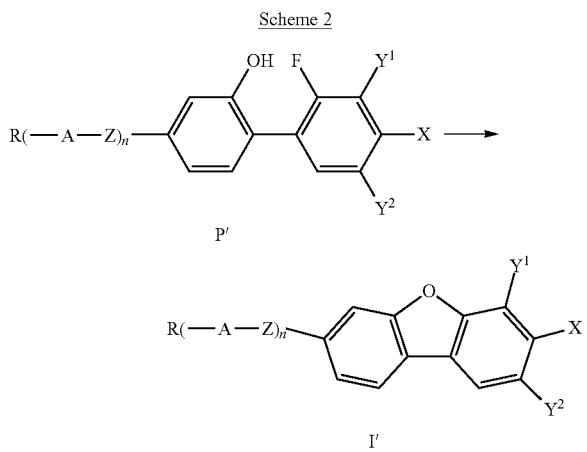

The dibenzofuran derivatives, i.e. the compounds of formula I wherein W denotes S (formula I″) are preferably synthesized as shown in scheme 3.

Scheme 3

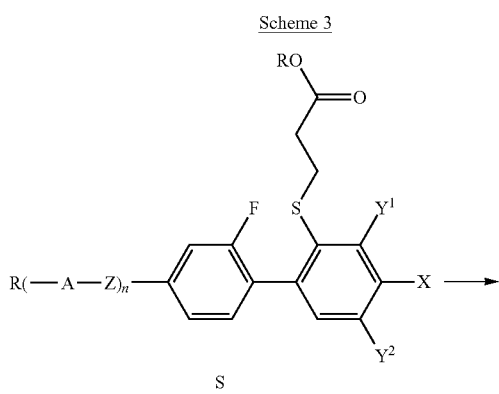

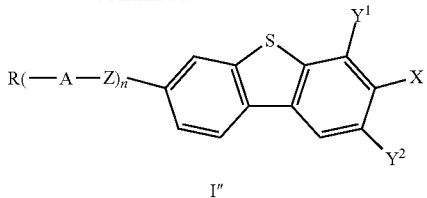

The intermediates S (scheme 3) are obtainable from the phenols P (scheme 1) via the corresponding triflate according to Itoh, Takahiro and Mase, Toshiaki, Organic Letters, 6(24), 4587-4590; 2004. Treatment of the compounds S with a strong, non-nucleophilic base, preferably potassium tert.-butanoate yields compounds I″ (cf. Jepsen, Tue Heesgaard et al., European Journal of Organic Chemistry, (1), 53-57, S53/1-S53/65; 2011).

Another object of the present invention is thus a compound of formula P or P' for use in a process for the synthesis of compounds of formula I, in which the occurring groups and parameters have the meanings given above for formula I.

A further object of the present invention is a process for the synthesis of the compound of formula I from a compound of formula P or P, preferably following the synthetic pathway depicted in scheme 1, scheme 2 or scheme 3 above.

The reactions described should only be regarded as illustrative. The person skilled in the art can carry out corresponding variations of the syntheses described and also follow other suitable synthetic routes in order to obtain compounds of the formula I.

The compounds of the general formula I can be used in liquid-crystalline media. The present invention therefore also relates to a liquid-crystalline medium comprising two or more liquid-crystalline compounds, comprising one or more compounds of the general formula I.

The present invention also relates to liquid-crystalline media comprising 2 to 40, preferably 4 to 30, components as further constituents besides one or more compounds of the formula I according to the invention. These media particularly preferably comprise 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, 1,3-dioxanes, 2,5-tetrahydropyrans, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid or of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-biscyclohexylbenzenes, 4',4'-biscyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylethanes, 1-phenyl-2-cyclohexylphenylethanes, optionally halogenated stilbenes, benzyl phenyl ethers, tolans and substituted cinnamic acids. The 1,4-phenylene groups in these compounds may also be mono- or polyfluorinated.

The most important compounds suitable as further constituents of media according to the invention can be characterised by the formulae (II), (III), (IV), (V) and (VI):

R'-L-E-R" (II)

R'-L-(CO)O-E-R" (III)

R'-L-O(CO)-E-R" (IV)

R'-L-CH$_2$CH$_2$-E-R" (V)

R'-L-CF$_2$O-E-R" (VI)

In the formulae (II), (III), (IV), (V) and (VI), L and E, which may be identical or different, each, independently of one another, denote a divalent radical from the group formed by -Phe-, -Cyc-, -Phe-Phe-, -Phe-Cyc-, -Cyc-Cyc-, -Pyr-, -Dio-, -Thp-, -G-Phe- and -G-Cyc- and their mirror images, where Phe denotes unsubstituted or fluorine-substituted 1,4-phenylene, Cyc denotes trans-1,4-cyclohexylene or 1,4-cyclohexenylene, Pyr denotes pyrimidine-2,5-diyl or pyridine-2,5-diyl, Dio denotes 1,3-dioxane-2,5-diyl, Thp denotes tetrahydropyran-2,5-diyl and G denotes 2-(trans-1,4-cyclohexyl)ethyl, pyrimidine-2,5-diyl, pyridine-2,5-diyl, 1,3-dioxane-2,5-diyl or tetrahydropyran-2,5-diyl.

One of the radicals L and E is preferably Cyc or Phe. E is preferably Cyc, Phe or Phe-Cyc. The media according to the invention preferably comprise one or more components selected from the compounds of the formulae (II), (III), (IV), (V) and (VI) in which L and E are selected from the group Cyc and Phe and simultaneously one or more components selected from the compounds of the formulae (II), (III), (IV), (V) and (VI) in which one of the radicals L and E is selected from the group Cyc and Phe and the other radical is selected from the group -Phe-Phe-, -Phe-Cyc-, -Cyc-Cyc-, -G-Phe- and -G-Cyc-, and optionally one or more components selected from the compounds of the formulae (II), (III), (IV), (V) and (VI) in which the radicals L and E are selected from the group -Phe-Cyc-, -Cyc-Cyc-, -G-Phe- and -G-Cyc-.

In a smaller sub-group of the compounds of the formulae (II), (III), (IV), (V) and (VI), R' and R" each, independently of one another, denote alkyl, alkenyl, alkoxy, alkoxyalkyl (oxaalkyl), alkenyloxy or alkanoyloxy having up to 8 C atoms. This smaller sub-group is called group A below, and the compounds are referred to by the sub-formulae (IIa), (IIIa), (IVa), (Va) and (VIa). In most of these compounds, R' and R" are different from one another, one of these radicals usually being alkyl, alkenyl, alkoxy or alkoxyalkyl (oxaalkyl).

In another smaller sub-group of the compounds of the formulae (II), (III), (IV), (V) and (VI), which is known as group B, E denotes a fluorinated phenylene radical of the formula

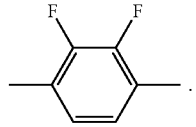

In the compounds of group B, which are referred to by the sub-formulae (IIb), (IIIb), (IVb), (Vb) and (VIb), R' and R" have the meaning indicated for the compounds of the sub-formulae (IIa) to (VIa) and are preferably alkyl, alkenyl, alkoxy or alkoxyalkyl (oxaalkyl).

In a further sub-group of the compounds of the formulae (II), (III), (IV), (V) and (VI), R" denotes —F, —Cl, —CN, —NCS or —(O)$_i$CH$_{3-k}$F$_k$, where i is 0 or 1 and k is 1, 2 or 3. This sub-group is referred to below as group C, and the compounds of this sub-group are correspondingly described by sub-formulae (IIc), (IIIc), (IVc), (Vc) and (VIc). In the compounds of the sub-formulae (IIc), (IIIc), (IVc), (Vc) and (VIc), R' has the meaning indicated for the compounds of the sub-formulae (IIa) to (VIa) and is preferably alkyl, alkenyl, alkoxy or alkoxyalkyl (oxaalkyl).

Besides the preferred compounds of groups A, B and C, other compounds of the formulae (II), (III), (IV), (V) and (VI) having other variants of the proposed substituents are also customary. All these substances are obtainable by methods which are known from the literature or analogously thereto.

Besides the compounds of the general formula I according to the invention, the media according to the invention preferably comprise one or more compounds from groups A, B and/or C. The media preferably comprise one or more compounds from group A and one or more compounds from group B for dielectrically negative mixtures or additionally one or more compounds from group C for dielectrically positive mixtures. The proportions by weight of the compounds from these groups in the media according to the invention are:

group A:

0 to 90%, preferably 15 to 90%, in particular 20 to 85%.

group B:

0 to 80%, preferably 10 to 85%, in particular 15 to 80%.

group C:

0 to 80%, preferably 15 to 90%, in particular 20 to 85%.

The media according to the invention preferably comprise 1 to 30%, particularly preferably 2 to 20%, of the compounds of the formula I according to the invention.

The media preferably comprise one, two, three, four or five compounds of the formula I according to the invention.

In a preferred embodiment of the present invention the liquid-crystalline medium comprises a) one or more compounds selected from the group of compounds of formulae II and III, preferably having a dielectric anisotropy of greater than 3:

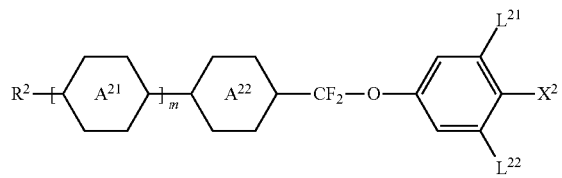
II

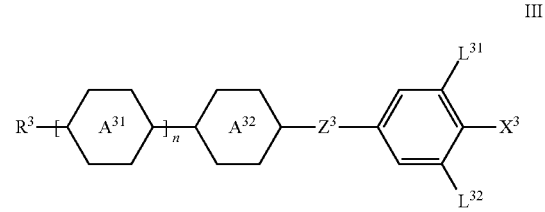
III in which
R² denotes alkyl, alkoxy, fluorinated alkyl or fluorinated alkoxy having 1 to 7 C atoms, alkenyl, alkenyloxy, alkoxyalkyl or fluorinated alkenyl having 2 to 7 C atoms and preferably alkyl or alkenyl,

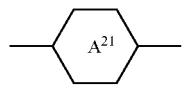 and 

on each appearance, independently of one another, denote

, ,

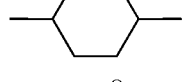, 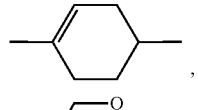,

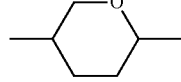, 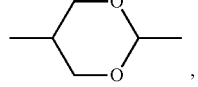,

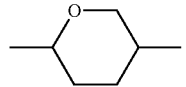, 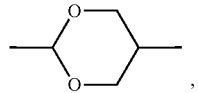,

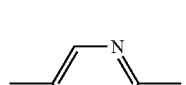, 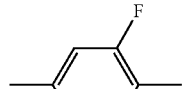,

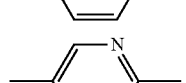, 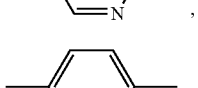,

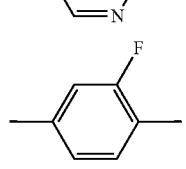, 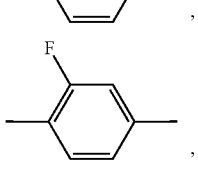,

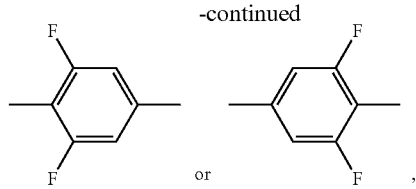 or preferably

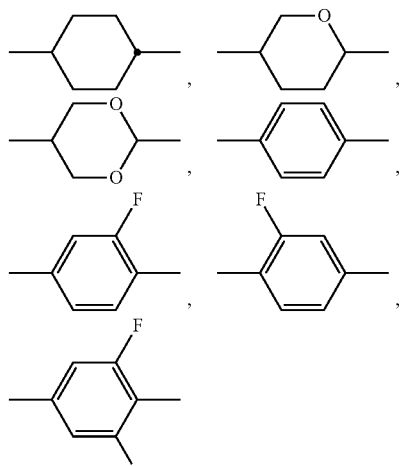

$L^{21}$ and $L^{22}$ denote H or F, preferably $L^{21}$ denotes F,
$X^2$ denotes halogen, halogenated alkyl or alkoxy having 1 to 3 C atoms or halogenated alkenyl or alkenyloxy having 2 or 3 C atoms, preferably F, Cl, —OCF₃, —O—CH₂CF₃, —O—CH=CF₂ or —CF₃, very preferably F, Cl, —O—CH=CF₂ or —OCF₃,
m is 0, 1, 2 or 3, preferably 1 or 2 and particularly preferably 1,
R³ denotes alkyl, alkoxy, fluorinated alkyl or fluorinated alkoxy having 1 to 7 C atoms, alkenyl, alkenyloxy, alkoxyalkyl or fluorinated alkenyl having 2 to 7 C atoms and preferably alkyl or alkenyl,

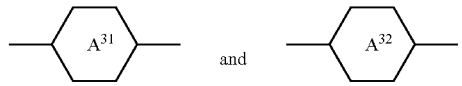 and on each appearance, independently of one another, are

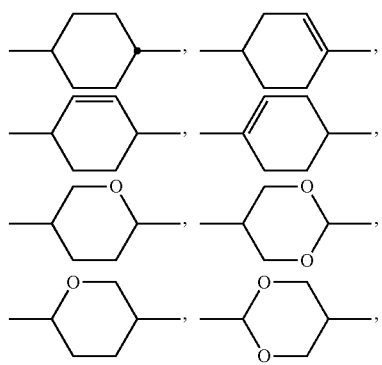

-continued

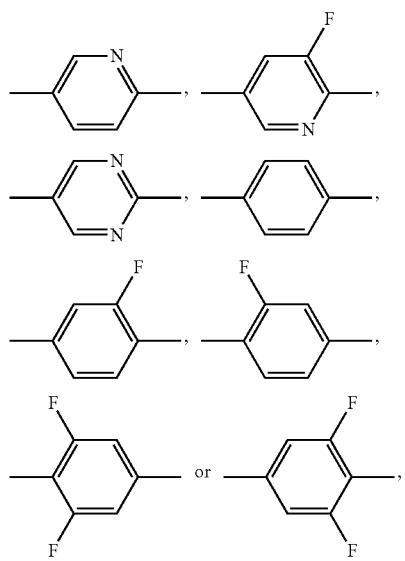

preferably

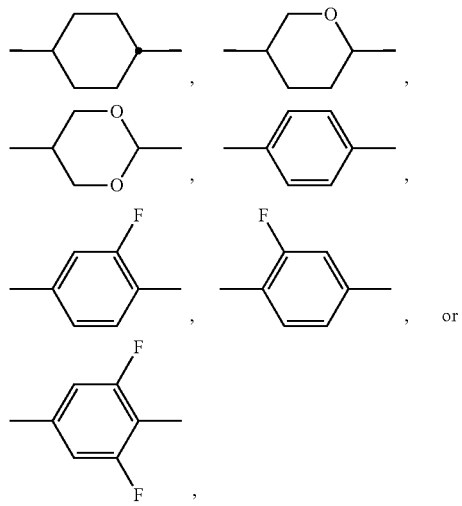

L³¹ and L³², independently of one another, denote H or F, preferably L³¹ denotes F, X³ denotes halogen, halogenated alkyl or alkoxy having 1 to 3 C atoms or halogenated alkenyl or alkenyloxy having 2 or 3 C atoms, preferably F, Cl, —OCF₃, —OCHF₂, —O—CH₂CF₃, —O—CH=CF₂, —O—CH=CH₂ or —CF₃, very preferably F, Cl, —O—CH=CF₂, —OCHF₂ or —OCF₃, Z³ denotes —CH₂CH₂—, —CF₂CF₂—, —COO—, trans-CH=CH—, trans-CF=CF—, —CH₂O— or a single bond, preferably —CH₂CH₂—, —COO—, trans-CH=CH— or a single bond and very preferably —COO—, trans-CH=CH— or a single bond, and n is 0, 1, 2 or 3, preferably 1, 2 or 3 and particularly preferably 1, and b) optionally one or more, preferably dielectrically neutral, compounds selected from the group of formulae IV and V:

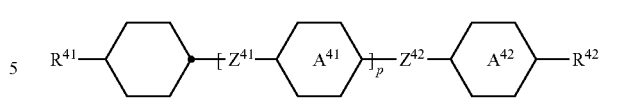

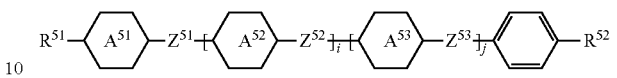

in which

R⁴¹ and R⁴², independently of one another, have the meaning indicated above for R² under formula II, preferably R⁴¹ denotes alkyl and R⁴² denotes alkyl or alkoxy or R⁴¹ denotes alkenyl and R⁴² denotes alkyl,

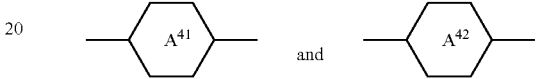

independently of one another and, if

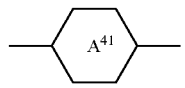

occurs twice, also these independently of one another, denote

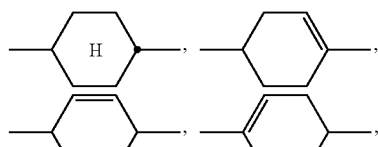

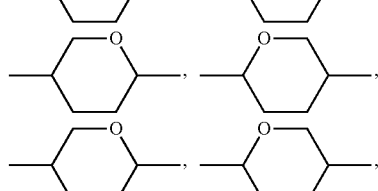

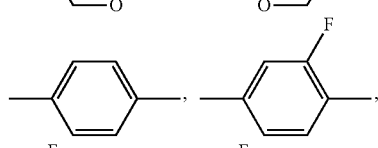

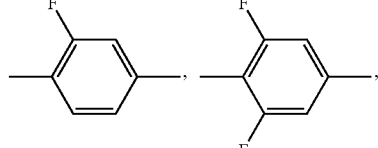

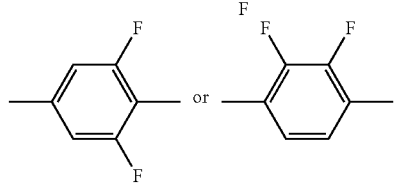

preferably one or more of

 and 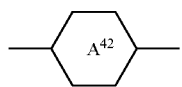

denotes or denote,

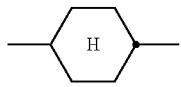

$Z^{41}$ and $Z^{42}$, independently of one another and, if $Z^{41}$ occurs twice, also these independently of one another,
denote —CH$_2$CH$_2$—, —COO—, trans-CH=CH—, trans-CF=CF—, —CH$_2$O—, —CF$_2$O—, —C≡C— or a single bond, preferably one or more thereof denotes/denote a single bond, and p denotes 0, 1 or 2, preferably 0 or 1, and $R^{51}$ and $R^{52}$, independently of one another, have one of the meanings given for $R^{41}$ and $R^{42}$ and preferably denote alkyl having 1 to 7 C atoms, preferably n-alkyl, particularly preferably n-alkyl having 1 to 5 C atoms, alkoxy having 1 to 7 C atoms, preferably n-alkoxy, particularly preferably n-alkoxy having 2 to 5 C atoms, alkoxyalkyl, alkenyl or alkenyloxy having 2 to 7 C atoms, preferably having 2 to 4 C atoms, preferably alkenyloxy,

 to , if present, each, independently of one another, denote

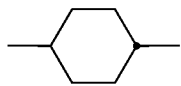, ,

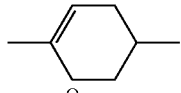, 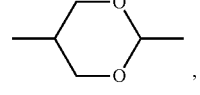,

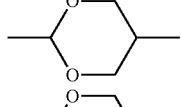, 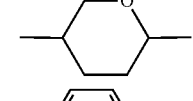,

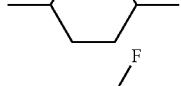 or 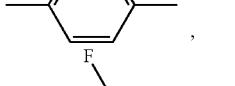, preferably

, ,

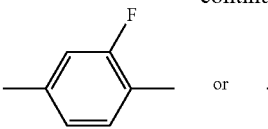 or 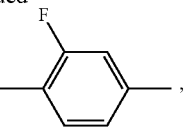, preferably

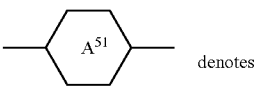 denotes 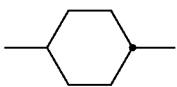, and, if present,

preferably denotes

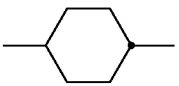, $Z^{51}$ to $Z^{53}$ each, independently of one another, denote —CH$_2$—CH$_2$—, —CH$_2$—O—, —CH=CH—, —C≡C—, —COO— or a single bond, preferably —CH$_2$—CH$_2$—, —CH$_2$—O— or a single bond and particularly preferably a single bond, i and j each, independently of one another, denote 0 or 1, (i+j) preferably denotes 0, 1 or 2, more preferably 0 or 1 and, most preferably, 1.

The present invention also relates to electro-optical liquid-crystal display elements containing a liquid-crystalline medium according to the invention.

The media according to the invention are prepared in a manner conventional per se. In general, the components are dissolved in one another, advantageously at elevated temperature. By means of suitable additives, the liquid-crystalline phases of the present invention can be modified in such a way that they can be used in all types of liquid-crystal display elements that have been disclosed hitherto. Additives of this type are known to the person skilled in the art and are described in detail in the literature (H. Kelker/R. Hatz, Handbook of Liquid Crystals, Verlag Chemie, Weinheim, 1980). For example, pleochroic dyes can be used for the preparation of coloured guest-host systems or substances can be added in order to modify the dielectric anisotropy, the viscosity and/or the alignment of the nematic phases.

For the present invention and in the following examples, the structures of the liquid-crystal compounds are indicated by means of acronyms, with the transformation into chemical formulae taking place in accordance with Tables A to C below. All radicals C$_n$H$_{2n+1}$, C$_m$H$_{2m+1}$ and C$_l$H$_{2l+1}$ or C$_n$H$_{2n}$, C$_m$H$_{2m}$ and C$_l$H$_{2l}$ are straight-chain alkyl radicals or alkylene radicals, in each case having n, m and l C atoms respectively. Preferably n, m and l are independently of each other 1, 2, 3, 4, 5, 6, or 7. Table A shows the codes for the ring elements of the nuclei of the compound, Table B lists the bridging units, and Table C lists the meanings of the symbols for the left- and right-hand end groups of the molecules. The acronyms are composed of the codes for the ring elements with optional linking groups, followed by a first hyphen and the codes for the left-hand end group, and a second hyphen and the codes for the right-hand end group. Table D shows illustrative structures of compounds together with their respective abbreviations.

TABLE A

Ring elements

| | | | |
|---|---|---|---|
| C | 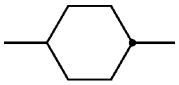 | | |
| D | 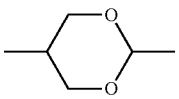 | DI | 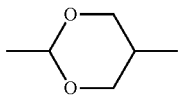 |
| A | 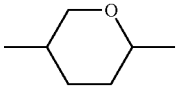 | AI | 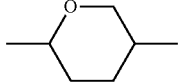 |
| P | 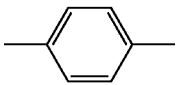 | | |
| G | 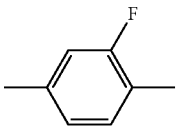 | GI | 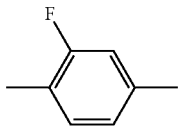 |
| U | 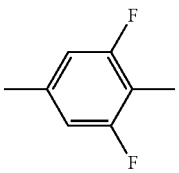 | UI | 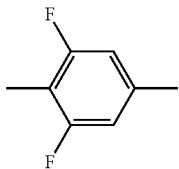 |
| Y | 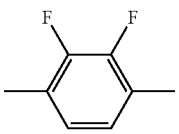 | | |
| P(F, Cl)Y | 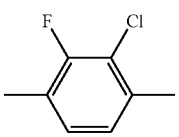 | P(Cl,F)Y | 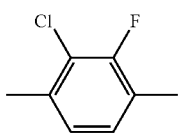 |
| np | 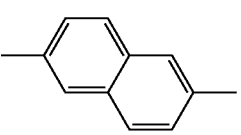 | | |
| n3f | 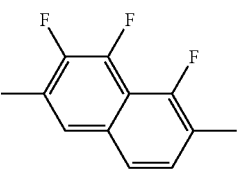 | nN3fl | 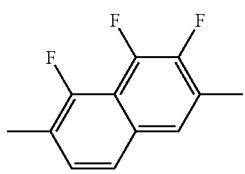 |
| th | 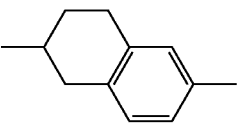 | thl | 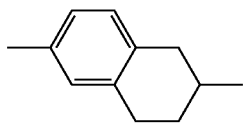 |

TABLE A-continued

| Ring elements | | | |
|---|---|---|---|
| tH2f | (structure) | tH2fl | (structure) |
| o2f | (structure) | o2fl | (structure) |
| dh | (structure) | | |
| B | (structure) | B(S) | (structure) |
| Bh | (structure) | Bh(S) | (structure) |
| BhF | (structure) | BhF(S) | (structure) |
| O | (structure) | S | (structure) |
| K | (structure) | KI | (structure) |
| L | (structure) | LI | (structure) |
| F | (structure) | Fl | (structure) |

TABLE B

Bridging units

| | | | |
|---|---|---|---|
| E | —CH₂—CH₂— | | |
| V | —CH=CH— | | |
| T | —C≡C— | | |
| W | —CF₂—CF₂— | | |
| B | —CF=CF— | | |
| Z | —CO—O— | ZI | —O—CO— |
| X | —CF=CH— | XI | —CH=CF— |
| O | —CH₂—O— | OI | —O—CH₂— |
| Q | —CF₂—O— | QI | —O—CF₂— |

TABLE C

End groups

| On the left individually or in combination | | On the right individually or in combination | |
|---|---|---|---|
| -n- | $C_nH_{2n+1}$— | -n | —$C_nH_{2n+1}$ |
| -nO- | $C_nH_{2n+1}$—O— | -nO | —O—$C_nH_{2n+1}$ |
| -V- | CH₂=CH— | -V | —CH=CH₂ |
| -nV- | $C_nH_{2n+1}$—CH=CH— | -nV | —$C_nH_{2n}$—CH=CH₂ |
| -Vn- | CH₂=CH—$C_nH_{2n}$— | -Vn | —CH=CH—$C_nH_{2n+1}$ |
| -nVm- | $C_nH_{2n+1}$—CH=CH—$C_mH_{2m}$— | -nVm | —$C_nH_{2n}$—CH=CH—$C_mH_{2m+1}$ |
| -N- | N≡C— | -N | —C≡N |
| -S- | S=C=N— | -S | —N=C=S |
| -F- | F— | -F | —F |
| -Cl- | Cl— | -Cl | —Cl |
| -M- | CFH₂— | -M | —CFH₂ |
| -D- | CF₂H— | -D | —CF₂H |
| -T- | CF₃— | -T | —CF₃ |
| -MO- | CFH₂O— | -OM | —OCFH₂ |
| -DO- | CF₂HO— | -OD | —OCF₂H |
| -TO- | CF₃O— | -OT | —OCF₃ |
| -A- | H—C≡C— | -A | —C≡C—H |
| -nA- | $C_nH_{2n+1}$—C≡C— | -An | —C≡C—$C_nH_{2n+1}$ |
| -NA- | N≡C—C≡C— | -AN | —C≡C—C≡N |

| On the left only in combination | | On the right only in combination | |
|---|---|---|---|
| -...n...- | —$C_nH_{2n}$— | -...n... | —$C_nH_{2n}$— |
| -...M...- | —CFH— | -...M... | —CFH— |
| -...D...- | —CF₂— | -...D... | —CF₂— |
| -...V...- | —CH=CH— | -...V... | —CH=CH— |
| -...Z...- | —CO—O— | -...Z... | —CO—O— |
| -...ZI...- | —O—CO— | -...ZI... | —O—CO— |
| -...K...- | —CO— | -...K... | —CO— |
| -...W...- | —CF=CF— | -...W... | —CF=CF— | in which n and m are each integers, and the three dots "..." are placeholders for other abbreviations from this table.

In addition to the compounds of formula I, the mixtures according to the invention preferably comprise one or more compounds of the compounds shown in Table D below.

The following abbreviations are used:

(n, m, k and l are, independently of one another, each an integer, preferably 1 to 9 preferably 1 to 7, k and l possibly may be also 0 and preferably are 0 to 4, more preferably 0 or 2 and most preferably 2, n preferably is 1, 2, 3, 4 or 5, in the combination "-nO-" it preferably is 1, 2, 3 or 4, preferably 2 or 4, m preferably is 1, 2, 3, 4 or 5, in the combination "-Om" it preferably is 1, 2, 3 or 4, more preferably 2 or 4. The combination "-IVm" preferably is "2V1".)

TABLE D

Examples of compounds of formula I

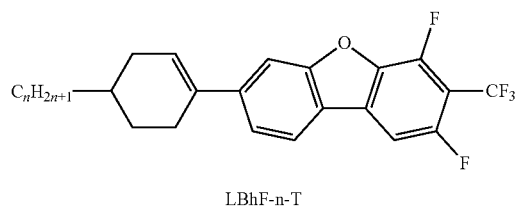

LBhF-n-T

TABLE D-continued

Examples of compounds of formula I

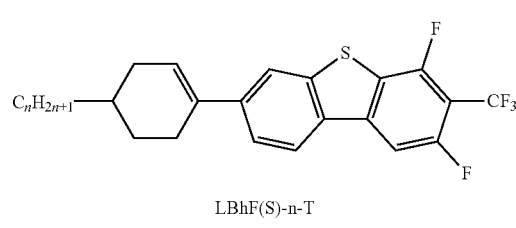

LBhF(S)-n-T

Exemplary, preferred dielectrically positive compounds that can be used in combination with compounds of formula I
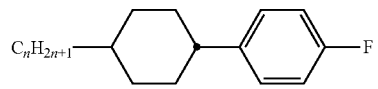
CP-n-F
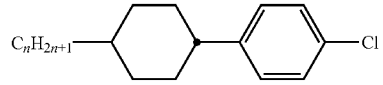
CP-n-CL
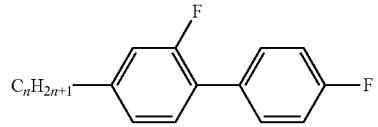
GP-n-F
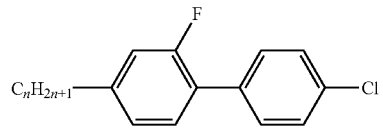
GP-n-CL
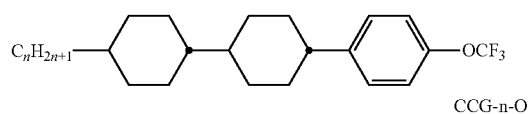
CCP-n-OT
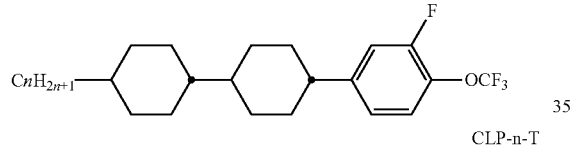
CCG-n-OT
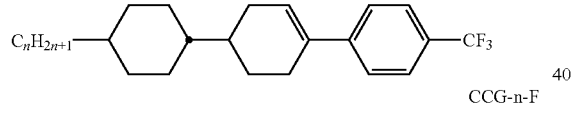
CLP-n-T
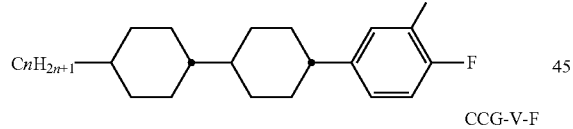
CCG-n-F
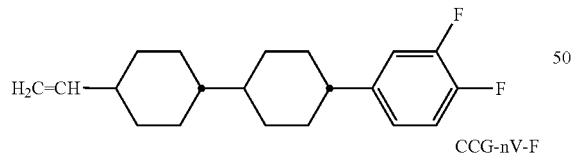
CCG-V-F
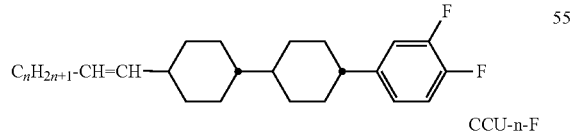
CCG-nV-F
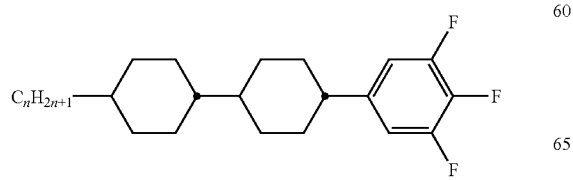
CCU-n-F
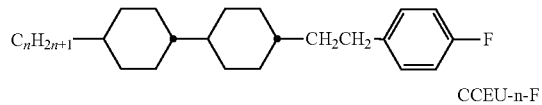
CCEP-n-F
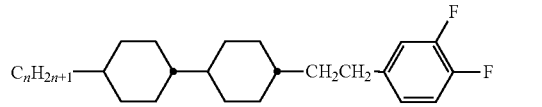
CCEU-n-F
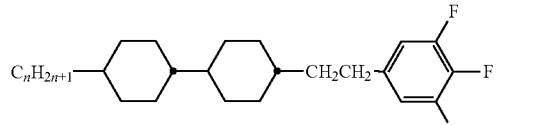
CCEU-n-F
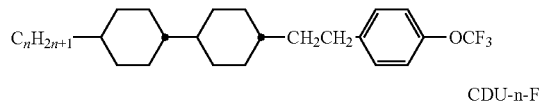
CCEP-n-OT
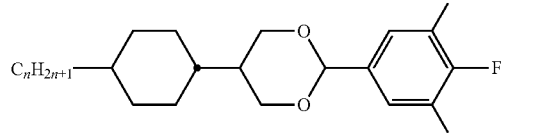
CDU-n-F
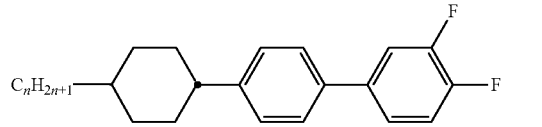
CPG-n-F
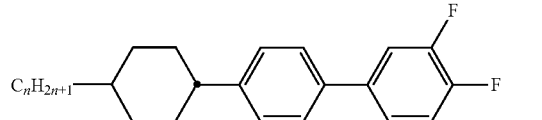
CPU-n-F
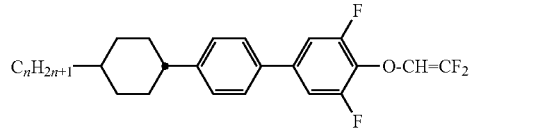
CPU-n-OXF
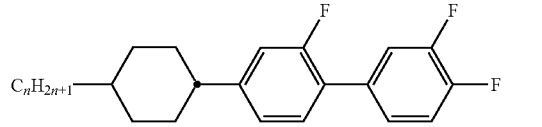
CGG-n-F
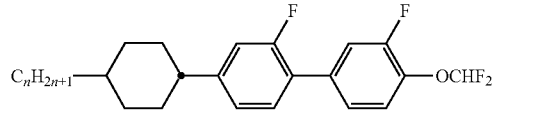
CGG-n-OD

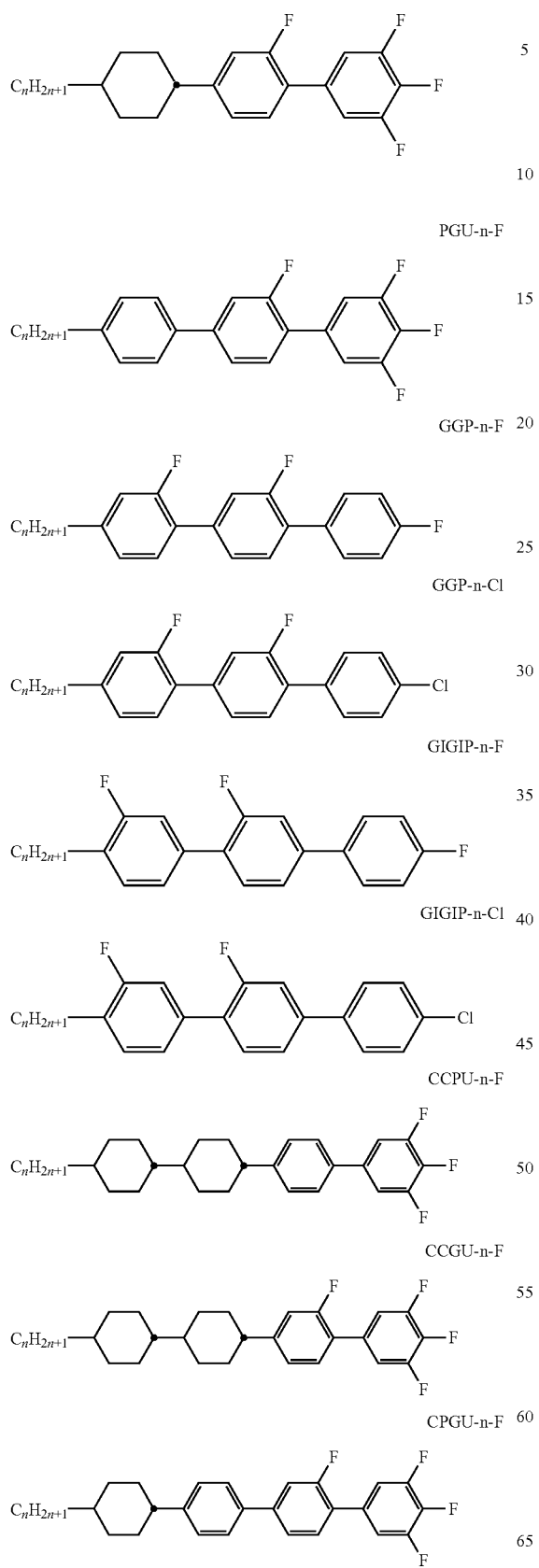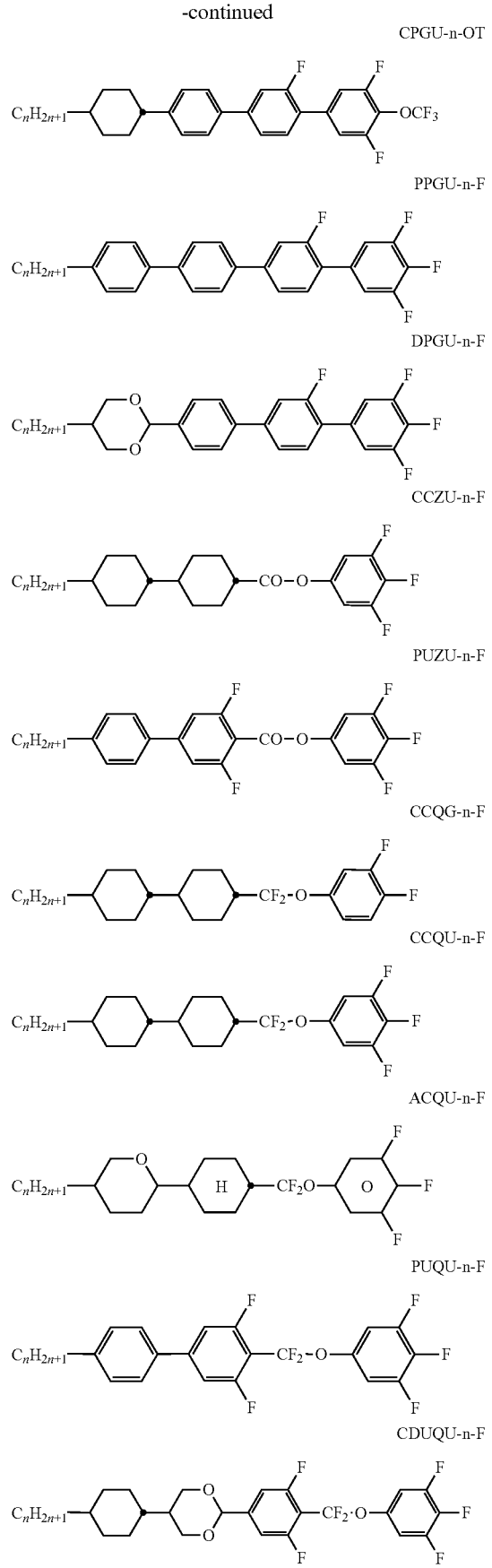

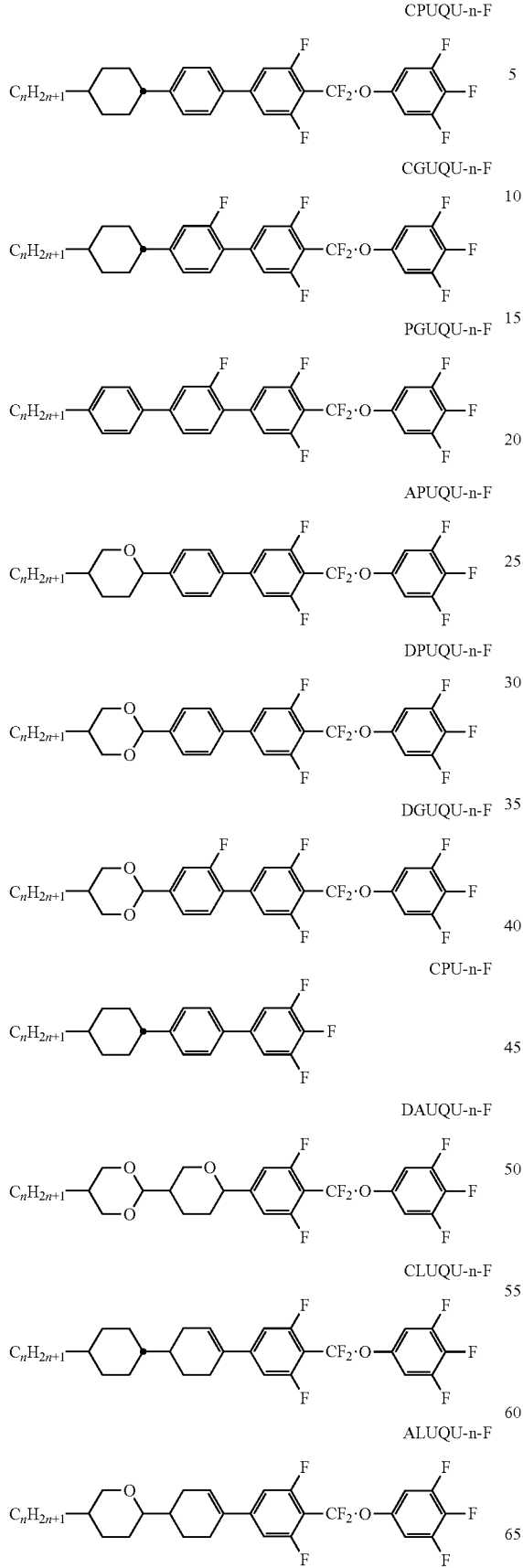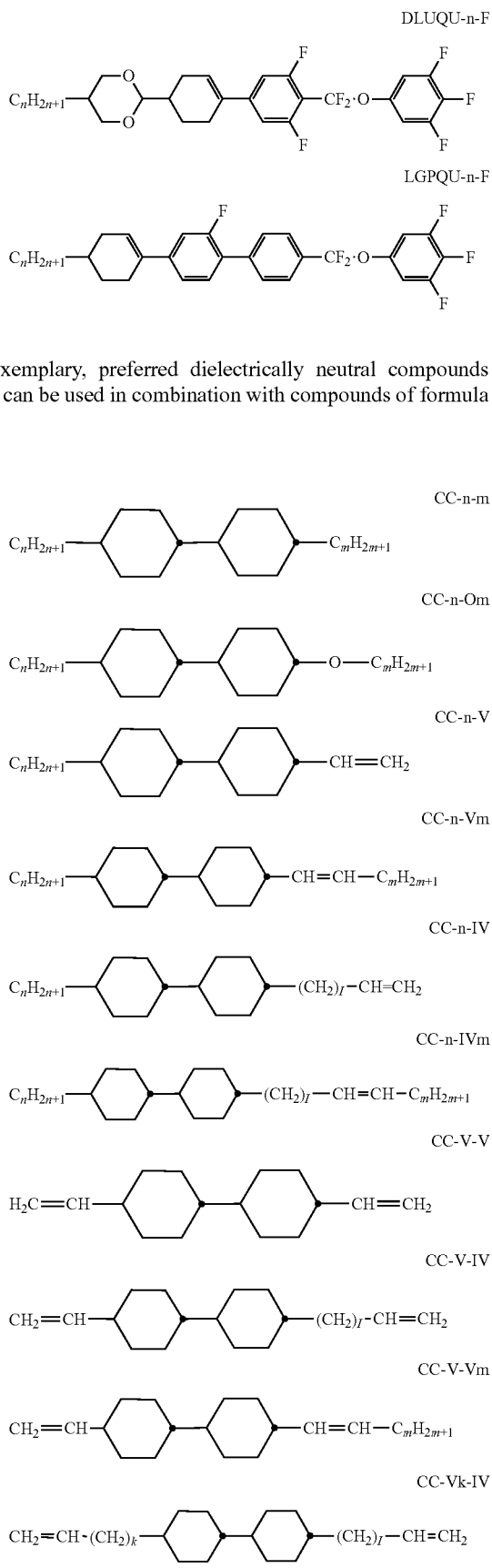
Exemplary, preferred dielectrically neutral compounds that can be used in combination with compounds of formula I CC-nV-IV
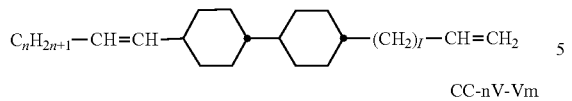
CC-nV-Vm
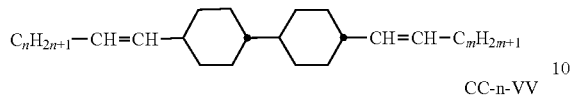
CC-n-VV
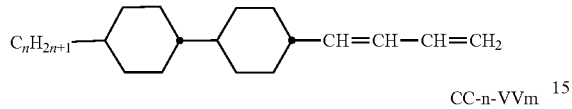
CC-n-VVm
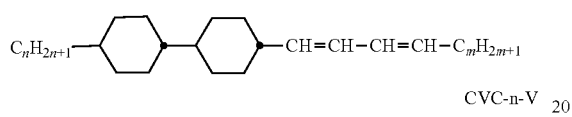
CVC-n-V
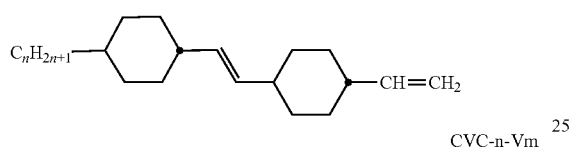
CVC-n-Vm
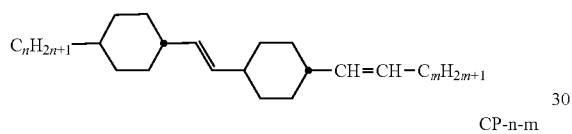
CP-n-m
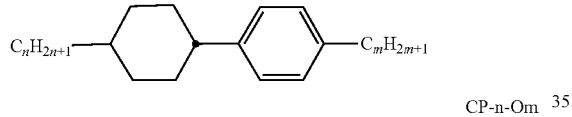
CP-n-Om
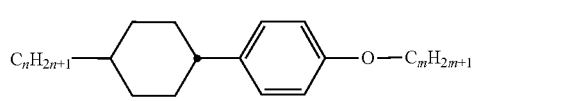
PP-n-m
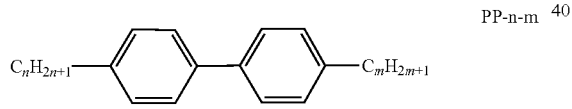
PP-n-Om
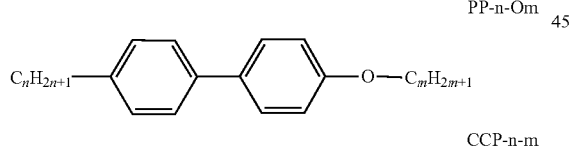
CCP-n-m
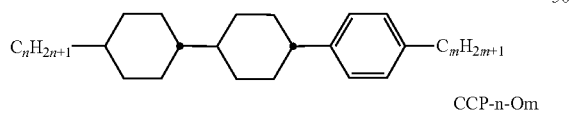
CCP-n-Om
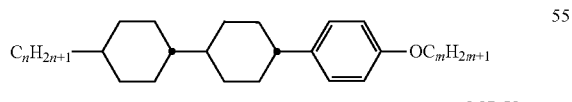
CCP-V-m
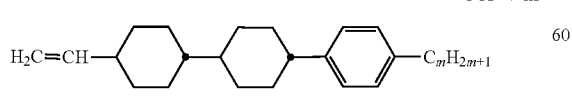
CCP-nV-m
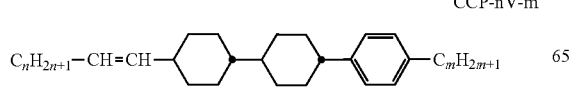
CCP-VI-m
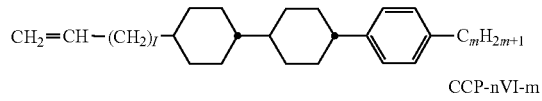
CCP-nVI-m
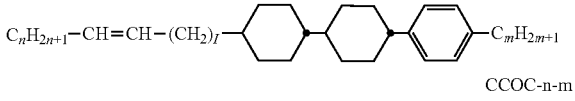
CCOC-n-m
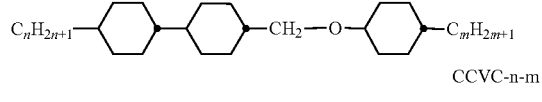
CCVC-n-m
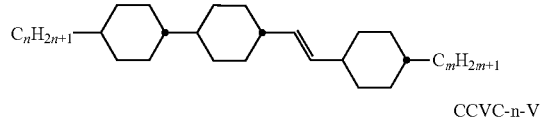
CCVC-n-V
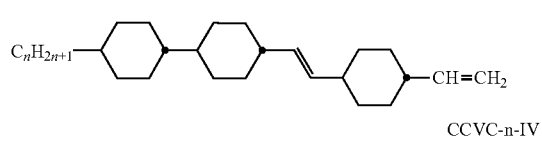
CCVC-n-IV
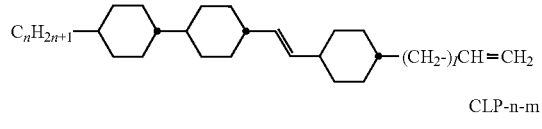
CLP-n-m
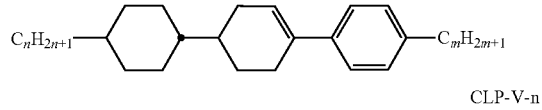
CLP-V-n
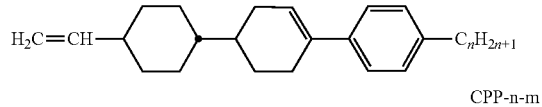
CPP-n-m
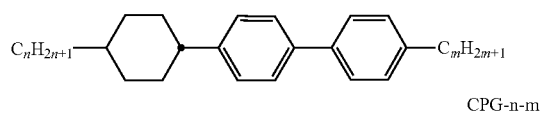
CPG-n-m
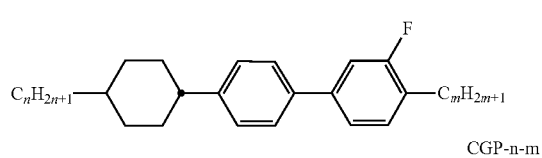
CGP-n-m
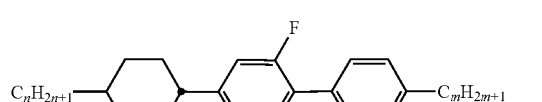
PGP-n-m
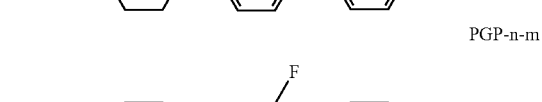
PGP-n-IV
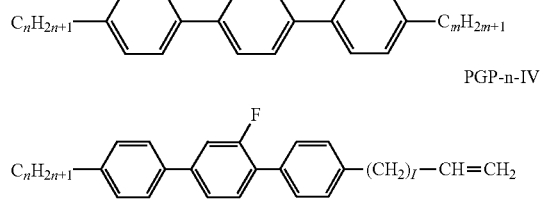

-continued
PGP-n-IVm
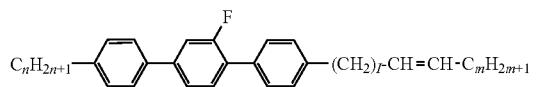
CGPC-n-m
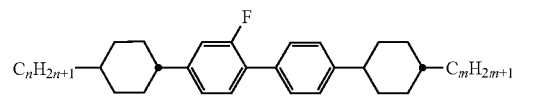
CCZPC-n-m
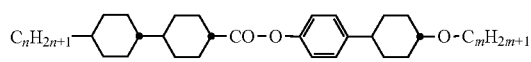
CPGP-n-m
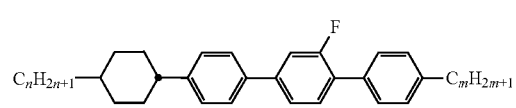
CPPC-n-m
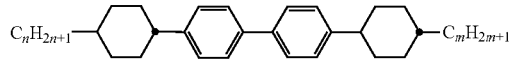
Table E shows chiral dopants which are preferably employed in the mixtures according to the invention.
TABLE E
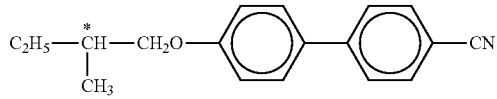
C 15
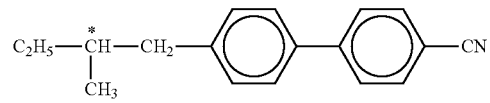
CB 15
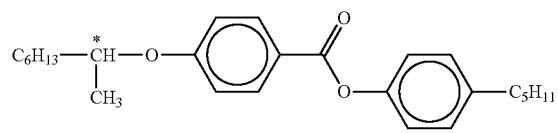
CM 21
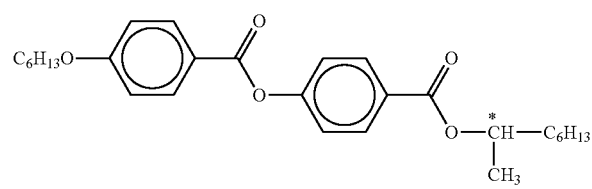
R S-811/S-811
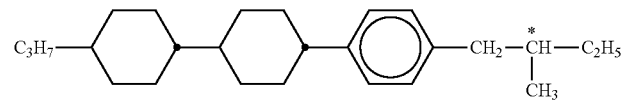
CM 44
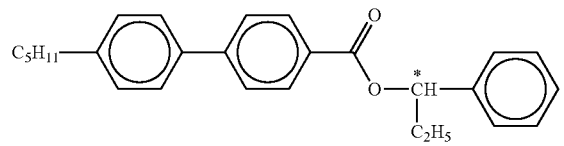
CM 45

TABLE E-continued
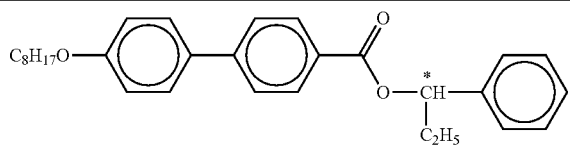
CM 47
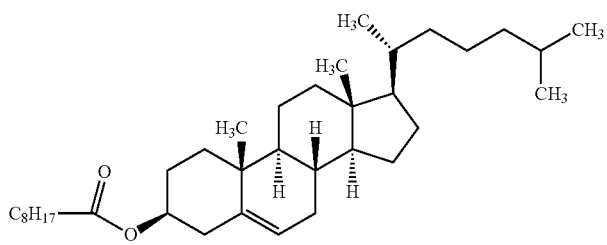
CN
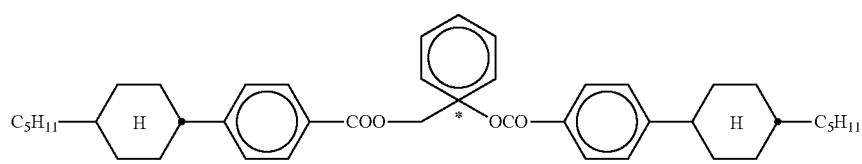
R-1011/S-1011
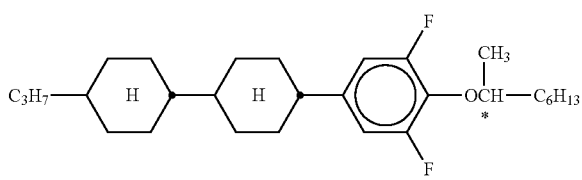
R-2011/S-2011
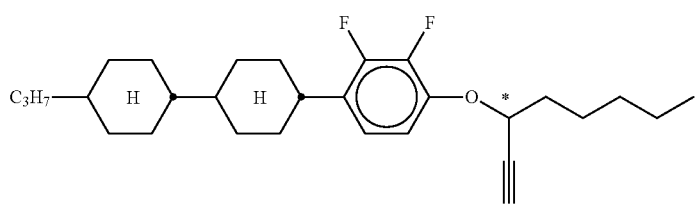
R-3011/S-3011
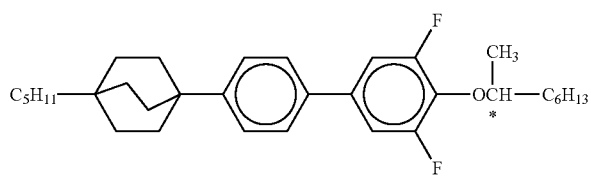
R-4011/S-4011
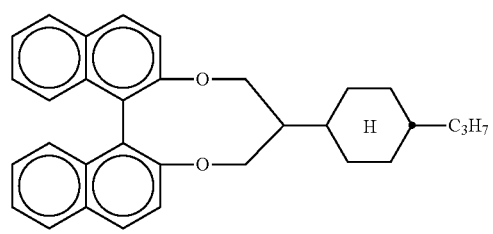
R-5011/S-5011

In a preferred embodiment of the present invention, the media according to the invention comprise one or more compounds selected from the group of the compounds from Table E.

Table F shows stabilisers which can preferably be employed in the mixtures according to the invention in addition to the compounds of formula B. The parameter n here denotes an integer in the range from 1 to 12. In particular, the phenol derivatives shown can be employed as additional stabilisers since they act as antioxidants.

TABLE F

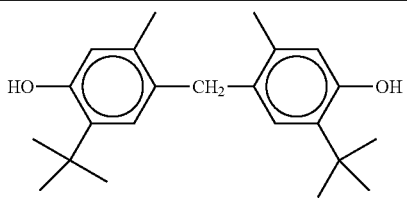

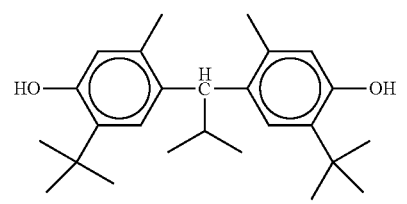

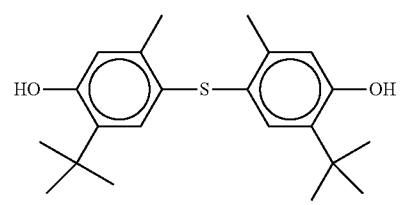

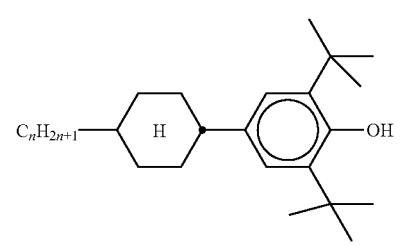

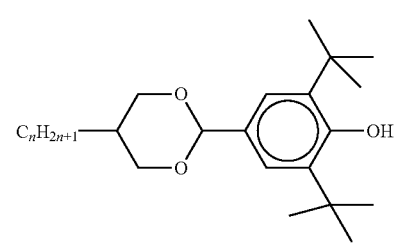

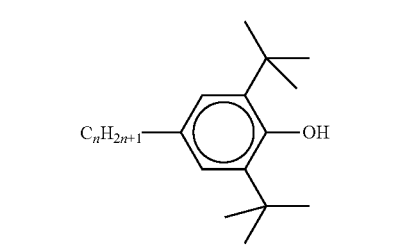

TABLE F-continued

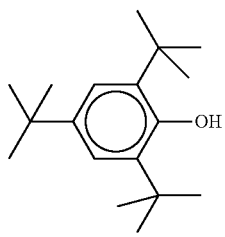

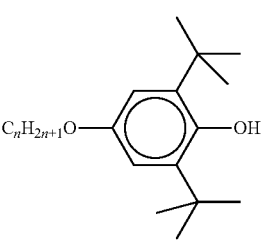

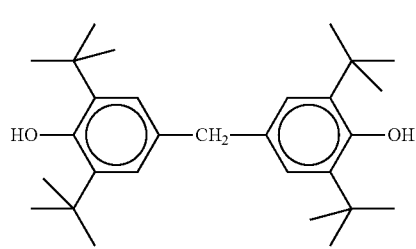

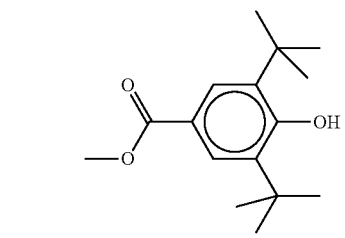

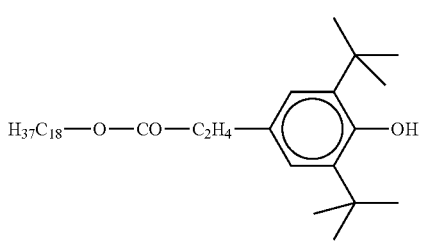

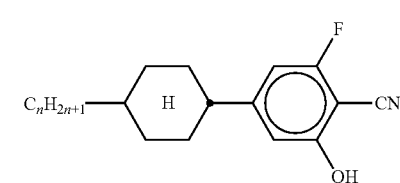

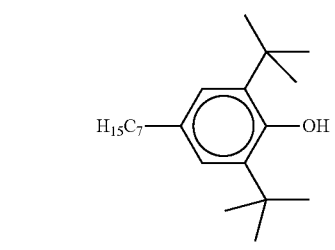

TABLE F-continued
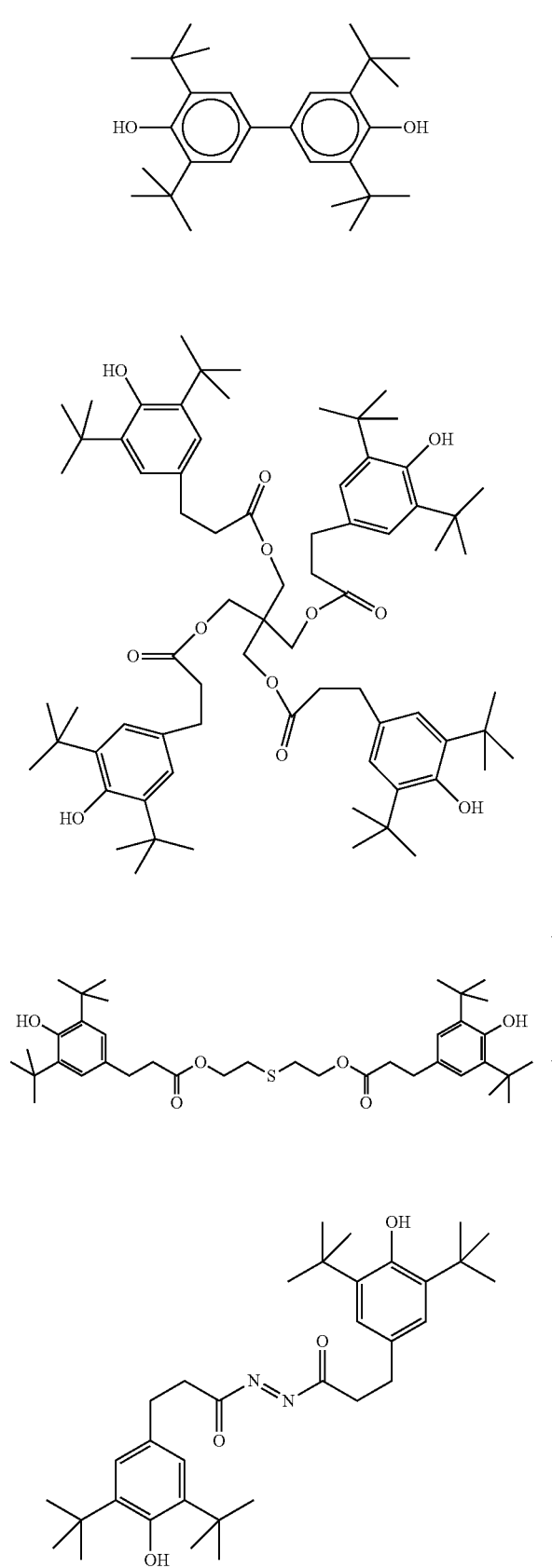
TABLE F-continued
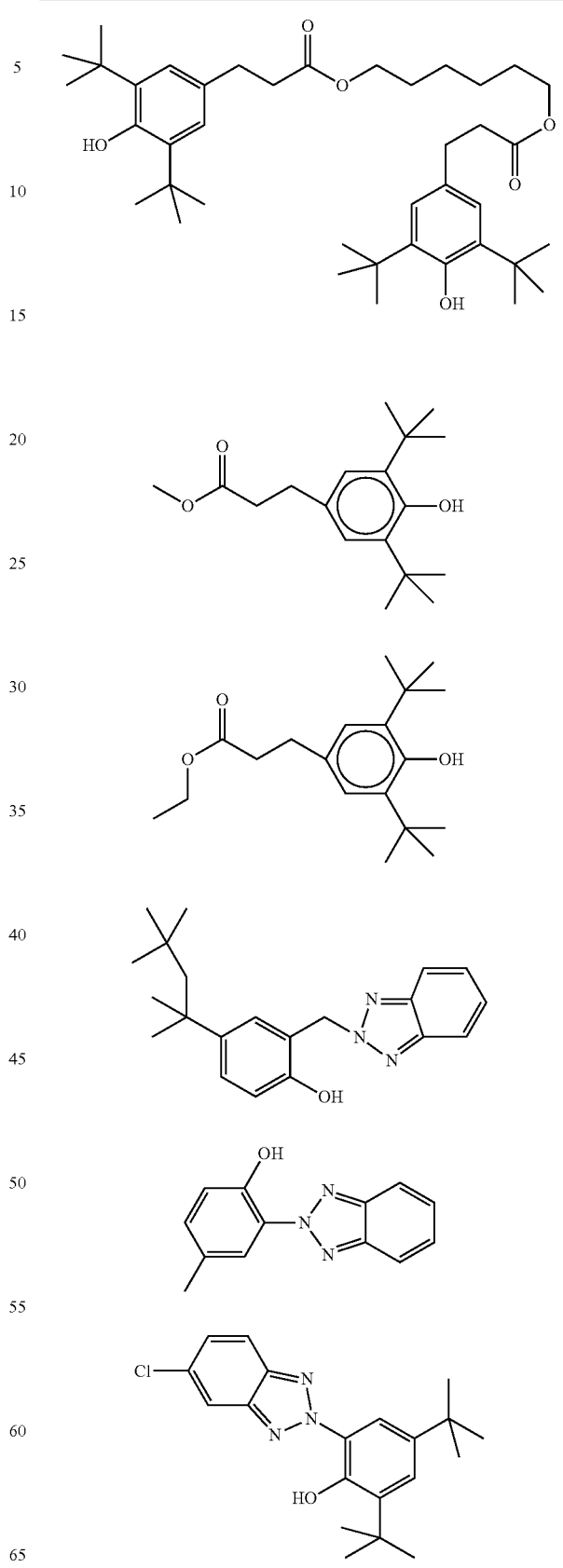

TABLE F-continued
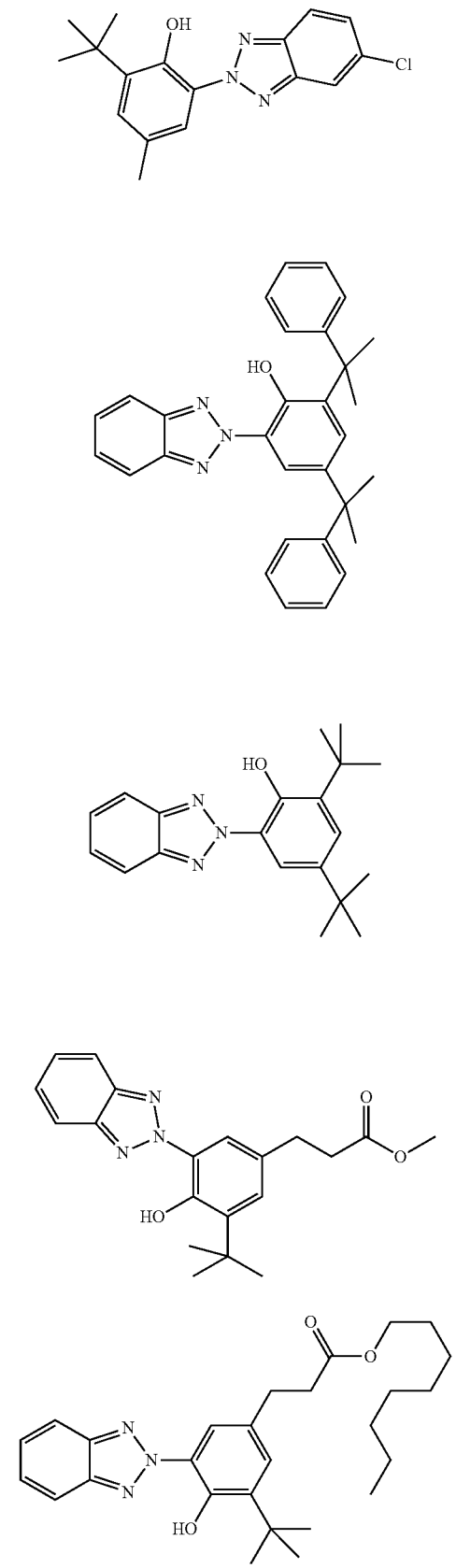
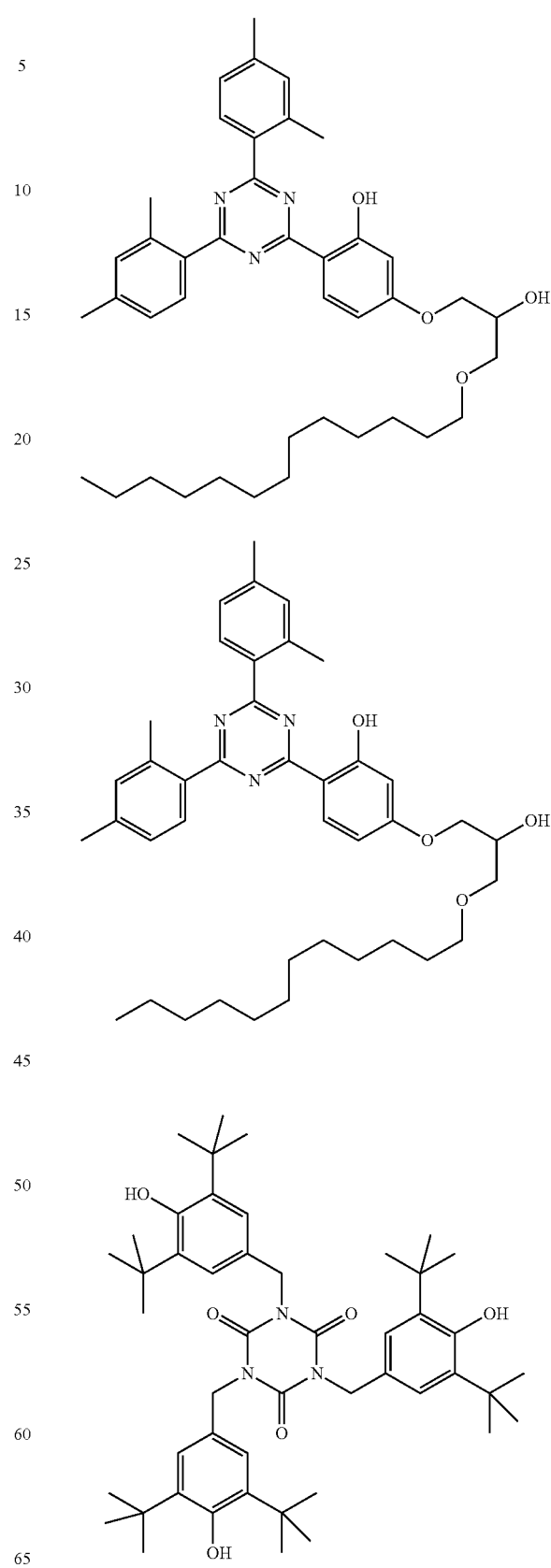

TABLE F-continued

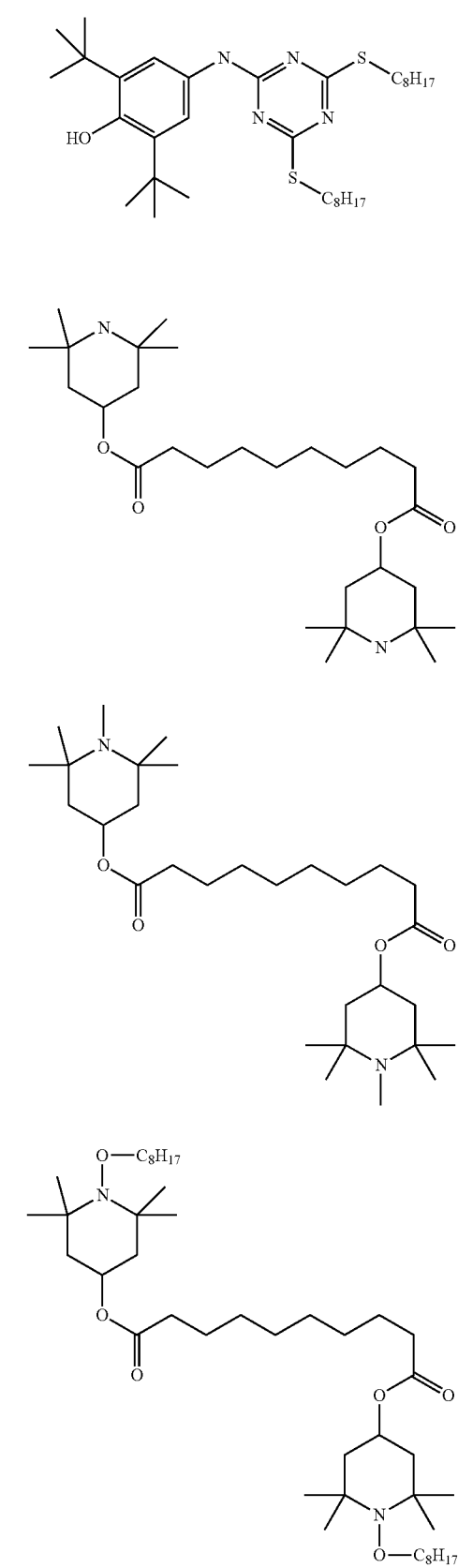

TABLE F-continued

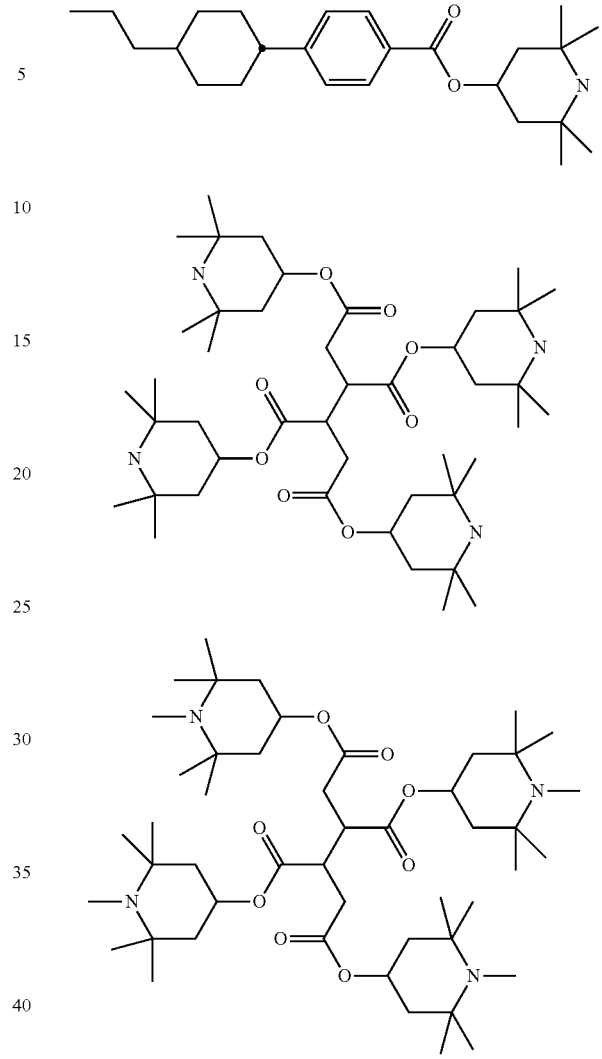

In a preferred embodiment of the present invention, the media according to the invention comprise one or more compounds selected from the group of the compounds from Table F.

The invention is explained in greater detail below with reference to working examples, but without being restricted thereby.

Above and below, Δn denotes the optical anisotropy (589 nm, 20° C.) and Δε denotes the dielectric anisotropy (1 kHz, 20° C.).

The Δε and Δn values of the compounds according to the invention are obtained by extrapolation from liquid-crystalline mixtures consisting of 10% of the respective compound according to the invention and 90% of the commercially available liquid-crystal mixture ZLI-2857 (for Δε) or ZLI-4792 (for Δn) (Merck KGaA, Darmstadt). In cases of limited solubility, the compound is measured in a mixture comprising only 5% of the compound, which is noted by the addition (5%) after the values in question.

Abbreviations

THF Tetrahydrofuran
MTB ether Methyl tert.-butyl ether

CataCXium A Di(1-adamantyl)-n-butylphosphine
Cr crystalline
S smectic
N nematic
I isotropic
Sx is used as a generic label for unidentified higher-ordered smectic phases.

SYNTHESIS EXAMPLES

Example 1: 2,4-Difluoro-7-(4-propylcyclohexen-1-yl)-3-(trifluoromethyl)dibenzofuran (1)

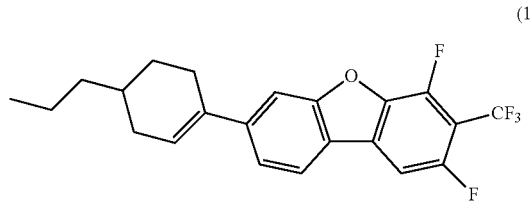
(1)

Step 1.1:
1-(4-Bromo-3-fluoro-phenyl)-4-propyl-cyclohexanol

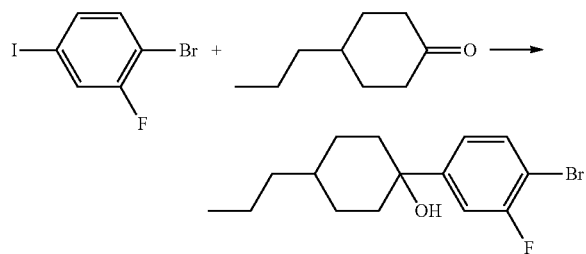

A solution of 1-bromo-2-fluoro-4-iodo-benzene (CAS-no. 136434-77-0, 40.2 g, 134 mmol) in THF (250 mL) is cooled to −5° C., followed by dropwise addition of a solution of isopropyl magnesium chloride (2 mol/L in THF, 68 mL, 136 mmol) and THF (100 mL). The reaction mixture is stirred for 90 min at 0° C. Then a solution of 4-propylcyclohexanone (CAS-no. 40649-36-3, 19.1 g, 136 mmol) in THF (50 mL) is added dropwise at 0° C., and the reaction mixture is slowly warmed up to room temperature and stirred for 3 h. The reaction mixture is hydrolyzed with ice water, diluted with MTB ether and acidified with hydrochloride acid (2 N). The aqueous phase is separated and extracted with MTB ether. The combined organic phases are washed with brine, dried (sodium sulfate) and concentrated in vacuo. 1-(4-bromo-3-fluoro-phenyl)-4-propyl-cyclohexanol is isolated as a yellow oil.

Step 1.2: 1-Bromo-2-fluoro-4-(4-propylcyclohexen-1-yl)benzene

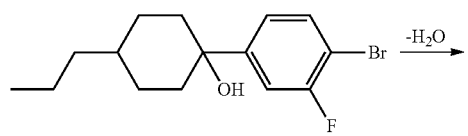

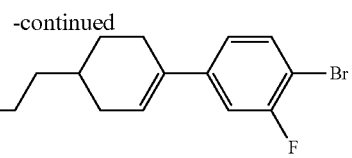

A mixture of 1-(4-bromo-3-fluoro-phenyl)-4-propyl-cyclohexanol (44 g, 97 mmol) and toluene-4-sulfonic acid monohydrate (1.5 g, 8 mmol) in toluene (400 mL) is heated at reflux temperature for 2 h. Then it is cooled to room temperature, neutralized with sodium hydroxide solution (2 N) and diluted with water. The aqueous phase is separated and extracted with toluene. The combined organic phases are dried (sodium sulfate) and concentrated in vacuo. The residue is purified by silica gel chromatography (solvent n-heptane) to give 1-bromo-2-fluoro-4-(4-propylcyclohexen-1-yl)benzene as a colorless oil.

Step 1.3: [2-Fluoro-4-(4-propylcyclohexen-1-yl)phenyl]boronic acid

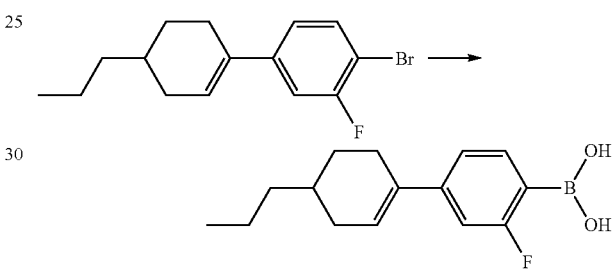

A solution of 1-bromo-2-fluoro-4-(4-propylcyclohexen-1-yl)benzene (80 g, 245 mmol) in THF (650 mL) is cooled to −65° C., followed by dropwise addition of butyl lithium solution (175 mL, 279 mmol) at −60° C. and stirred for 1 h. A solution of trimethyl borate (31 mL, 273 mmol) in THF (100 mL) is added dropwise at −65° C. and stirred for further 60 minutes. Then the reaction mixture is slowly allowed to warm up and hydrolyzed at 5° C. with water, diluted with MTB ether and acidified with hydrochloride solution (2 N). The aqueous phase is separated and extracted with MTB ether, the combined organic phases are washed with brine, dried (sodium sulfate) and concentrated in vacuo. The residue is extracted with n-heptane to give [2-fluoro-4-(4-propylcyclohexen-1-yl)phenyl]boronic acid as a light yellow solid.

Step 1.4:
6-Bromo-2,4-difluoro-3-(trifluoromethyl)phenol

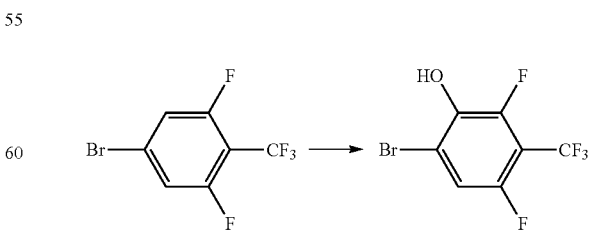

A solution of 5-bromo-1,3-difluoro-2-(trifluoromethyl)benzene (CAS-no. 156243-64-0, 86 g, 321 mmol) in THF (400 mL) is cooled to −75° C., followed by dropwise addition of lithium diisopropyl amide solution (200 mL, 400 mmol) and stirring at −75° C. for 1 h. Then trimethyl borate (75 mL, 660 mmol) is added dropwise at −75° C., and the reaction mixture is stirred for further 60 minutes. Then it is warmed up to 0° C. and a mixture of hydrochloride acid (10%, 500 mL) and THF (100 mL) is added. After phase separation, the organic phase is cooled to 0° C. Hydrogen peroxide (210 mL, 2.68 mol) is added at 0° C. to the reaction mixture, which is stirred for 1 h and then heated up to 40° C. and stirred overnight. It is cooled to room temperature, diluted with MTB ether, and the phases are separated. The organic phase is washed with dist. water, brine and sodium sulfite solution until peroxide-free. The organic phase is dried (sodium sulfate) and concentrated in vacuo. The residue is washed with sodium hydroxide solution and hydrochloride acid and purified by silica gel chromatography (solvent dichloromethane) to give 6-bromo-2,4-difluoro-3-(trifluoromethyl) phenol as a brown oil.

Step 1.5: 2,4-Difluoro-6-[2-fluoro-4-(4-propylcyclohexen-1-yl) phenyl]-3-(trifluoromethyl)phenol

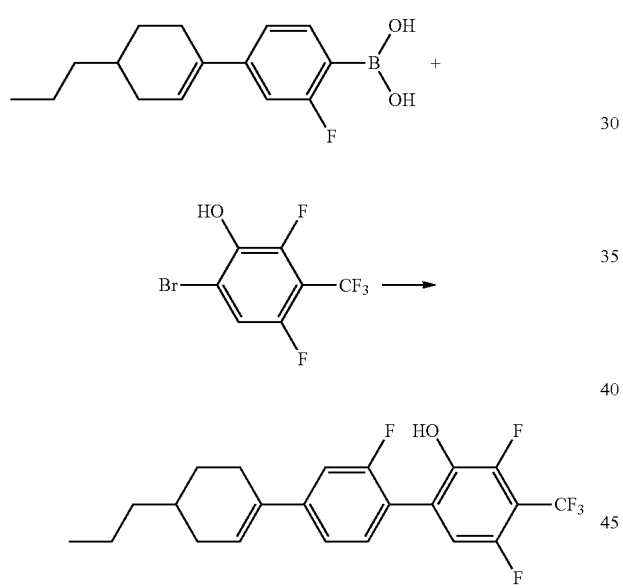

A mixture of 6-bromo-2,4-difluoro-3-(trifluoromethyl) phenol (9.5 g, 30 mmol), potassium carbonate (6.1 g, 44 mol), tris(dibenzylideneacetone)dipalladium(0) (57 mg, 0.1 mmol) and CataCXium A (33 mg, 0.1 mmol) in THF (50 mL) and dist. water (25 mL) is heated to reflux under nitrogen atmosphere, followed by dropwise addition of a solution of [2-fluoro-4-(4-propylcyclohexen-1-yl)phenyl] boronic acid 5 (7.8 g, 30 mmol) in THF (25 mL). The reaction mixture is heated at reflux temperature overnight. Then it is cooled to room temperature and diluted with MTB ether and dist. water. The aqueous phase is separated and extracted with MTB ether. The combined organic phases are washed with brine, dried (sodium sulfate) and concentrated in vacuo. The residue is purified by silica gel chromatography (solvent 1-chlorobutane). 2,4-difluoro-6-[2-fluoro-4-(4-propylcyclohexen-1-yl) phenyl]-3-(trifluoromethyl)phenol 8 is isolated as a light brown solid.

Step 1.6: 2,4-Difluoro-7-(4-propylcyclohexen-1-yl)-3-(trifluoromethyl)dibenzofuran

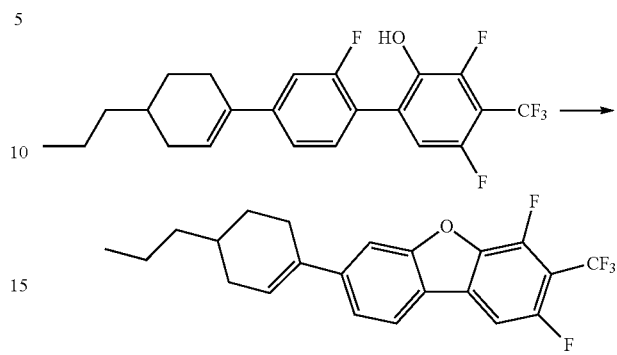

A mixture of 2,4-difluoro-6-[2-fluoro-4-(4-propylcyclohexen-1-yl) phenyl]-3-(trifluoromethyl) phenol 8 (3.2 g, 8 mmol), potassium phosphate monohydrate (2.4 g, 10 mmol) and 1,3-dimethyltetrahydro-2(1H)pyrimidinone (30 mL, 248 mmol) is stirred at 110° C. overnight. The reaction mixture is purified by silica gel chromatography (solvent n-heptane) and crystallization (ethanol) to give 2,4-difluoro-7-(4-propylcyclohexen-1-yl)-3-(trifluoromethyl)dibenzofuran as a colorless solid.

Phase Sequence: Tg−35 Cr 67 Sx (33) SmA (40) I.
Δε=18.5
Δn=0.2036

Example 2: 2,4-Difluoro-7-(4-propylcyclohexen-1-yl)-3-(trifluoromethyl)dibenzothiophene

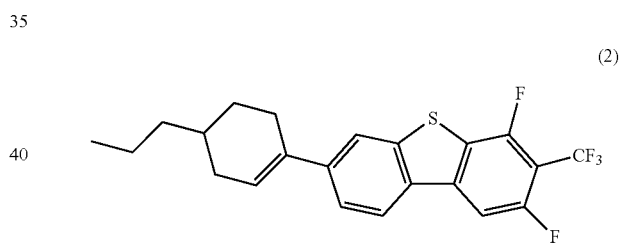

(2)

Step 2.1: [2,4-Difluoro-6-[2-fluoro-4-(4-propylcyclohexen-1-yl)phenyl]-3-(trifluoromethyl)phenyl] trifluoromethanesulfonate

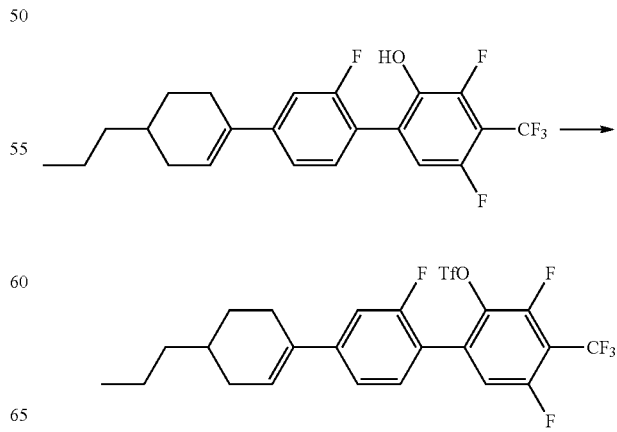

Trifluoromethanesulfonic anhydride (3 mL, 18 mmol) is slowly added to a solution of 2,4-difluoro-6-[2-fluoro-4-(4-propylcyclohexen-1-yl) phenyl]-3-(trifluoromethyl)phenol (6 g, 14 mmol), triethylamine (3 mL, 21 mmol) and 4-(dimethylamino)-pyridine (52 mg, 0.4 mmol) in dichloromethane (65 mL) at 5° C. under nitrogen atmosphere. The solution is stirred at room temperature overnight. The reaction mixture is purified by silica gel chromatography (solvent 1-chlorobutane) to give [2,4-difluoro-6-[2-fluoro-4-(4-propylcyclohexen-1-yl)phenyl]-3-(trifluoromethyl)phenyl] trifluoromethanesulfonate as a yellow oil.

Step 2.2: 2,4-Difluoro-7-(4-propylcyclohexen-1-yl)-3-(trifluoromethyl)dibenzothiophene

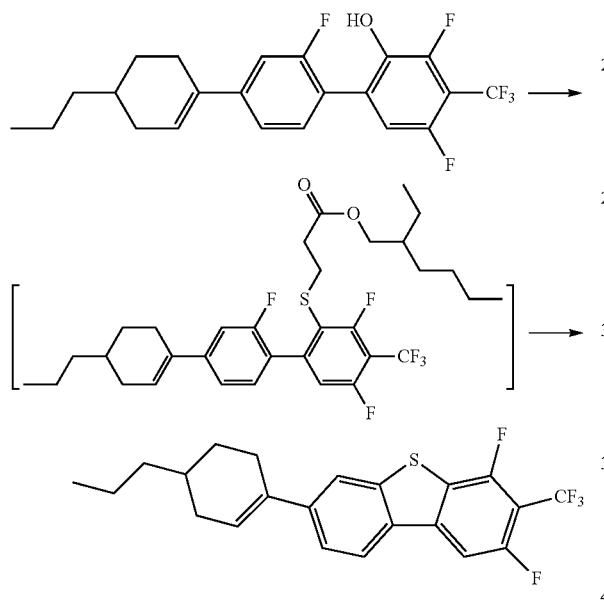

A solution of [2,4-difluoro-6-[2-fluoro-4-(4-propylcyclohexen-1-yl)phenyl]-3-(trifluoromethyl)phenyl] trifluoromethanesulfonate (8.2 g, 15 mmol), 3-mercapto-propionic acid 2-ethylhexyl ester (4.3 mL, 18 mmol) and N-ethyl diisopropyl amine (3.7 mL, 22 mmol) in toluene (40 mL) is degassed with Argon. Tris(dibenzylideneacetone)dipalladium(0) (140 mg, 0.2 mmol) and (oxydi-2,1-phenylene)bis(diphenylphosphine) (160 mg, 0.3 mmol) are quickly added to the solution, and the reaction mixture is heated at reflux overnight. Then it is cooled to room temperature, and a solution of potassium tert-butylate (2.0 g, 18 mmol) in THE (12 mL) is added to the reaction mixture containing intermediate in situ. The reaction mixture is heated at reflux overnight, followed by addition of a second portion of a solution of potassium tert-butylate (1.0 g, 9 mmol) in THE (6 mL). The reaction mixture is heated again at reflux overnight. Then it is cooled to room temperature, quenched with water, acidified with hydrochloric acid (25%) at 0° C. and diluted with MTB ether. The aqueous phase is separated and extracted with MTB ether. The combined organic phases are washed with dist. water and brine, dried (sodium sulfate) and concentrated in vacuo. The residue is purified by silica gel chromatography (solvent n-heptane) and crystallization (ethanol) to give 2,4-difluoro-7-(4-propylcyclohexen-1-yl)-3-(trifluoromethyl)dibenzothiophene 12 as colourless crystals.

Phase sequence: Cr 150 Sx 1161.
Δε=22.9
Δn=0.2101

Example 3

In analogy to example 1 is obtained:

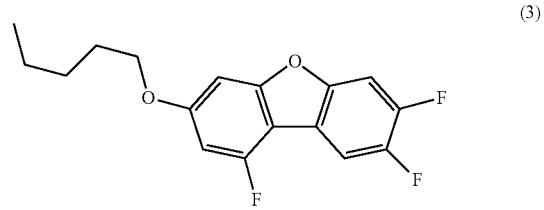 [SMILES: CCCCCOc1cc(F)c2c(c1)oc1cc(F)c(F)cc12]

Phase Sequence: Cr 85 I
Δε=12.3
Δn=0.1742

In analogy to the above described examples the following exemplary compounds of formula I and its respective sub-formulae are obtained:

In the following table the following abbreviations for the end groups are used

| Abbreviation | Structure |
|---|---|
| c-C$_3$H$_5$ | cyclopropyl |
| c-C$_3$H$_5$CH$_2$ | cyclopropylmethyl |
| c-C$_4$H$_7$ | cyclobutyl |
| c-C$_5$H$_7$ | cyclopentenyl |
| c-C$_5$H$_9$ | cyclopentyl |

The physical properties are given at a temperature of 20° C. and γ$_1$ is given in mPa·s. Phase transition temperatures are given in ° C.

I-1-1

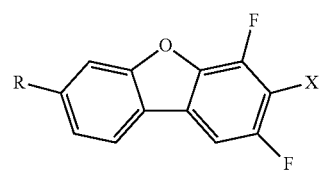

| No: 4- | R | X | Phase Range; properties |
|---|---|---|---|
| 1 | CH$_3$ | F | |
| 2 | C$_2$H$_5$ | F | |
| 3 | n-C$_3$H$_7$ | F | |
| 4 | n-C$_4$H$_9$ | F | |
| 5 | n-C$_5$H$_{11}$ | F | |

-continued

| No: 4- | R | X | Phase Range; properties |
|---|---|---|---|
| 6 | n-C$_6$H$_{13}$ | F | |
| 7 | n-C$_7$H$_{15}$ | F | |
| 8 | n-C$_8$H$_{17}$ | F | |
| 9 | c-C$_3$H$_5$ | F | |
| 10 | c-C$_3$H$_5$CH$_2$ | F | |
| 11 | c-C$_4$H$_7$ | F | |
| 12 | c-C$_5$H$_7$ | F | |
| 13 | c-C$_5$H$_9$ | F | |
| 14 | CH$_2$=CH | F | |
| 15 | CH$_3$CH=CH | F | |
| 16 | CH$_2$=CH(CH$_2$)$_2$ | F | |
| 17 | CH$_3$O | F | Cr 109 I |
| 18 | C$_2$H$_5$O | F | |
| 19 | n-C$_3$H$_7$O | F | Cr 81 I; Δn = 0.1411 Δε = 11.9; γ1 = 58 |
| 20 | n-C$_4$H$_9$O | F | |
| 21 | n-C$_5$H$_{11}$O | F | Cr 48 I; Δn = 0.1351 Δε = 9.9; γ1 = 69 |
| 22 | CH$_3$ | CF$_3$ | |
| 23 | C$_2$H$_5$ | CF$_3$ | |
| 24 | n-C$_3$H$_7$ | CF$_3$ | |
| 25 | n-C$_4$H$_9$ | CF$_3$ | |
| 26 | n-C$_5$H$_{11}$ | CF$_3$ | |
| 27 | n-C$_6$H$_{13}$ | CF$_3$ | |
| 28 | n-C$_7$H$_{15}$ | CF$_3$ | |
| 29 | n-C$_8$H$_{17}$ | CF$_3$ | |
| 30 | c-C$_3$H$_5$ | CF$_3$ | |
| 31 | c-C$_3$H$_5$CH$_2$ | CF$_3$ | |
| 32 | c-C$_4$H$_7$ | CF$_3$ | |
| 33 | c-C$_5$H$_7$ | CF$_3$ | |
| 34 | c-C$_5$H$_9$ | CF$_3$ | |
| 35 | CH$_2$=CH | CF$_3$ | |
| 36 | CH$_3$CH=CH | CF$_3$ | |
| 37 | CH$_2$=CH(CH$_2$)$_2$ | CF$_3$ | |
| 38 | CH$_3$O | CF$_3$ | |
| 39 | C$_2$H$_5$O | CF$_3$ | |
| 40 | n-C$_3$H$_7$O | CF$_3$ | |
| 41 | n-C$_4$H$_9$O | CF$_3$ | Cr 74 I; Δn = 0.1450 Δε = 19.1; γ1 = 121 |
| 42 | n-C$_5$H$_{11}$O | CF$_3$ | |
| 43 | CH$_3$ | OCF$_3$ | |
| 44 | C$_2$H$_5$ | OCF$_3$ | |
| 45 | n-C$_3$H$_7$ | OCF$_3$ | |
| 46 | n-C$_4$H$_9$ | OCF$_3$ | |
| 47 | n-C$_5$H$_{11}$ | OCF$_3$ | |
| 48 | n-C$_6$H$_{13}$ | OCF$_3$ | |
| 49 | n-C$_7$H$_{15}$ | OCF$_3$ | |
| 50 | n-C$_8$H$_{17}$ | OCF$_3$ | |
| 51 | c-C$_3$H$_5$ | OCF$_3$ | |
| 52 | c-C$_3$H$_5$CH$_2$ | OCF$_3$ | |
| 53 | c-C$_4$H$_7$ | OCF$_3$ | |
| 54 | c-C$_5$H$_7$ | OCF$_3$ | |
| 55 | c-C$_5$H$_9$ | OCF$_3$ | |
| 56 | CH$_2$=CH | OCF$_3$ | |
| 57 | CH$_3$CH=CH | OCF$_3$ | |
| 58 | CH$_2$=CH(CH$_2$)$_2$ | OCF$_3$ | |
| 59 | CH$_3$O | OCF$_3$ | |
| 60 | C$_2$H$_5$O | OCF$_3$ | |
| 61 | n-C$_3$H$_7$O | OCF$_3$ | |
| 62 | n-C$_4$H$_9$O | OCF$_3$ | Cr 82 I |
| 63 | n-C$_5$H$_{11}$O | OCF$_3$ | |

| No: 5- | R | X | Phase Range; properties |
|---|---|---|---|
| 1 | CH$_3$ | F | |
| 2 | C$_2$H$_5$ | F | |
| 3 | n-C$_3$H$_7$ | F | |
| 4 | n-C$_4$H$_9$ | F | |
| 5 | n-C$_5$H$_{11}$ | F | |
| 6 | n-C$_6$H$_{13}$ | F | |
| 7 | n-C$_7$H$_{15}$ | F | |
| 8 | n-C$_8$H$_{17}$ | F | |
| 9 | c-C$_3$H$_5$ | F | |
| 10 | c-C$_3$H$_5$CH$_2$ | F | |
| 11 | c-C$_4$H$_7$ | F | |
| 12 | c-C$_5$H$_7$ | F | |
| 13 | c-C$_5$H$_9$ | F | |
| 14 | CH$_2$=CH | F | |
| 15 | CH$_3$CH=CH | F | |
| 16 | CH$_2$=CH(CH$_2$)$_2$ | F | |
| 17 | CH$_3$O | F | Cr 146 I |
| 18 | C$_2$H$_5$O | F | |
| 19 | n-C$_3$H$_7$O | F | |
| 20 | n-C$_4$H$_9$O | F | |
| 21 | n-C$_5$H$_{11}$O | F | |
| 22 | CH$_3$ | CF$_3$ | |
| 23 | C$_2$H$_5$ | CF$_3$ | |
| 24 | n-C$_3$H$_7$ | CF$_3$ | |
| 25 | n-C$_4$H$_9$ | CF$_3$ | |
| 26 | n-C$_5$H$_{11}$ | CF$_3$ | |
| 27 | n-C$_6$H$_{13}$ | CF$_3$ | |
| 28 | n-C$_7$H$_{15}$ | CF$_3$ | |
| 29 | n-C$_8$H$_{17}$ | CF$_3$ | |
| 30 | c-C$_3$H$_5$ | CF$_3$ | |
| 31 | c-C$_3$H$_5$CH$_2$ | CF$_3$ | |
| 32 | c-C$_4$H$_7$ | CF$_3$ | |
| 33 | c-C$_5$H$_7$ | CF$_3$ | |
| 34 | c-C$_5$H$_9$ | CF$_3$ | |
| 35 | CH$_2$=CH | CF$_3$ | |
| 36 | CH$_3$CH=CH | CF$_3$ | |
| 37 | CH$_2$=CH(CH$_2$)$_2$ | CF$_3$ | |
| 38 | CH$_3$O | CF$_3$ | |
| 39 | C$_2$H$_5$O | CF$_3$ | |
| 40 | n-C$_3$H$_7$O | CF$_3$ | |
| 41 | n-C$_4$H$_9$O | CF$_3$ | Cr 97 SA (77) I; Δn =0.1571, Δε = 23.3; γ1 = 287 |
| 42 | n-C$_5$H$_{11}$O | CF$_3$ | |
| 43 | CH$_3$ | OCF$_3$ | |
| 44 | C$_2$H$_5$ | OCF$_3$ | |
| 45 | n-C$_3$H$_7$ | OCF$_3$ | |
| 46 | n-C$_4$H$_9$ | OCF$_3$ | |
| 47 | n-C$_5$H$_{11}$ | OCF$_3$ | |
| 48 | n-C$_6$H$_{13}$ | OCF$_3$ | |
| 49 | n-C$_7$H$_{15}$ | OCF$_3$ | |
| 50 | n-C$_8$H$_{17}$ | OCF$_3$ | |
| 51 | c-C$_3$H$_5$ | OCF$_3$ | |
| 52 | c-C$_3$H$_5$CH$_2$ | OCF$_3$ | |
| 53 | c-C$_4$H$_7$ | OCF$_3$ | |
| 54 | c-C$_5$H$_7$ | OCF$_3$ | |
| 55 | c-C$_5$H$_9$ | OCF$_3$ | |
| 56 | CH$_2$=CH | OCF$_3$ | |
| 57 | CH$_3$CH=CH | OCF$_3$ | |
| 58 | CH$_2$=CH(CH$_2$)$_2$ | OCF$_3$ | |
| 59 | CH$_3$O | OCF$_3$ | |
| 60 | C$_2$H$_5$O | OCF$_3$ | |
| 61 | n-C$_3$H$_7$O | OCF$_3$ | |
| 62 | n-C$_4$H$_9$O | OCF$_3$ | Cr 110 SA (95) I; Δn =0.1450, Δε = 17.3; γ1 = 240 |
| 63 | n-C$_5$H$_{11}$O | OCF$_3$ | |

I-2-1

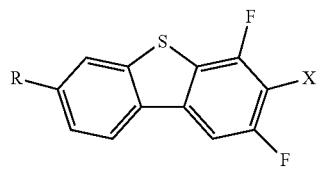

I-3-1

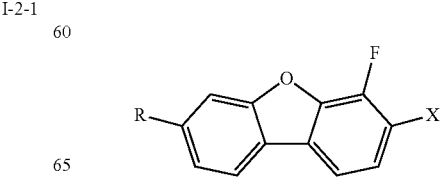

| No: 6- | R | X | Phase Range; properties |
|---|---|---|---|
| 1 | CH$_3$ | F | |
| 2 | C$_2$H$_5$ | F | |
| 3 | n-C$_3$H$_7$ | F | |
| 4 | n-C$_4$H$_9$ | F | |
| 5 | n-C$_5$H$_{11}$ | F | |
| 6 | n-C$_6$H$_{13}$ | F | |
| 7 | n-C$_7$H$_{15}$ | F | |
| 8 | n-C$_8$H$_{17}$ | F | |
| 9 | c-C$_3$H$_5$ | F | |
| 10 | c-C$_3$H$_5$CH$_2$ | F | |
| 11 | c-C$_4$H$_7$ | F | |
| 12 | c-C$_5$H$_7$ | F | |
| 13 | c-C$_5$H$_9$ | F | |
| 14 | CH$_2$=CH | F | |
| 15 | CH$_3$CH=CH | F | |
| 16 | CH$_2$=CH(CH$_2$)$_2$ | F | |
| 17 | CH$_3$O | F | |
| 18 | C$_2$H$_5$O | F | |
| 19 | n-C$_3$H$_7$O | F | |
| 20 | n-C$_4$H$_9$O | F | |
| 21 | n-C$_5$H$_{11}$O | F | |
| 22 | CH$_3$ | CF$_3$ | |
| 23 | C$_2$H$_5$ | CF$_3$ | |
| 24 | n-C$_3$H$_7$ | CF$_3$ | |
| 25 | n-C$_4$H$_9$ | CF$_3$ | |
| 26 | n-C$_5$H$_{11}$ | CF$_3$ | |
| 27 | n-C$_6$H$_{13}$ | CF$_3$ | |
| 28 | n-C$_7$H$_{15}$ | CF$_3$ | |
| 29 | n-C$_8$H$_{17}$ | CF$_3$ | |
| 30 | c-C$_3$H$_5$ | CF$_3$ | |
| 31 | c-C$_3$H$_5$CH$_2$ | CF$_3$ | |
| 32 | c-C$_4$H$_7$ | CF$_3$ | |
| 33 | c-C$_5$H$_7$ | CF$_3$ | |
| 34 | c-C$_5$H$_9$ | CF$_3$ | |
| 35 | CH$_2$=CH | CF$_3$ | |
| 36 | CH$_3$CH=CH | CF$_3$ | |
| 37 | CH$_2$=CH(CH$_2$)$_2$ | CF$_3$ | |
| 38 | CH$_3$O | CF$_3$ | |
| 39 | C$_2$H$_5$O | CF$_3$ | |
| 40 | n-C$_3$H$_7$O | CF$_3$ | |
| 41 | n-C$_4$H$_9$O | CF$_3$ | Cr 86 I; Δn = 0.1512; Δε = 12.1; γ1 = 134 |
| 42 | n-C$_5$H$_{11}$O | CF$_3$ | |
| 43 | CH$_3$ | OCF$_3$ | |
| 44 | C$_2$H$_5$ | OCF$_3$ | |
| 45 | n-C$_3$H$_7$ | OCF$_3$ | |
| 46 | n-C$_4$H$_9$ | OCF$_3$ | |
| 47 | n-C$_5$H$_{11}$ | OCF$_3$ | |
| 48 | n-C$_6$H$_{13}$ | OCF$_3$ | |
| 49 | n-C$_7$H$_{15}$ | OCF$_3$ | |
| 50 | n-C$_8$H$_{17}$ | OCF$_3$ | |
| 51 | c-C$_3$H$_5$ | OCF$_3$ | |
| 52 | c-C$_3$H$_5$CH$_2$ | OCF$_3$ | |
| 53 | c-C$_4$H$_7$ | OCF$_3$ | |
| 54 | c-C$_5$H$_7$ | OCF$_3$ | |
| 55 | c-C$_5$H$_9$ | OCF$_3$ | |
| 56 | CH$_2$=CH | OCF$_3$ | |
| 57 | CH$_3$CH=CH | OCF$_3$ | |
| 58 | CH$_2$=CH(CH$_2$)$_2$ | OCF$_3$ | |
| 59 | CH$_3$O | OCF$_3$ | |
| 60 | C$_2$H$_5$O | OCF$_3$ | |
| 61 | n-C$_3$H$_7$O | OCF$_3$ | |
| 62 | n-C$_4$H$_9$O | OCF$_3$ | Cr 63 I |
| 63 | n-C$_5$H$_{11}$O | OCF$_3$ | |

| No: 7- | R | X | Phase Range; properties |
|---|---|---|---|
| 1 | CH$_3$ | F | |
| 2 | C$_2$H$_5$ | F | |
| 3 | n-C$_3$H$_7$ | F | |
| 4 | n-C$_4$H$_9$ | F | |
| 5 | n-C$_5$H$_{11}$ | F | |
| 6 | n-C$_6$H$_{13}$ | F | |
| 7 | n-C$_7$H$_{15}$ | F | |
| 8 | n-C$_8$H$_{17}$ | F | |
| 9 | c-C$_3$H$_5$ | F | |
| 10 | c-C$_3$H$_5$CH$_2$ | F | |
| 11 | c-C$_4$H$_7$ | F | |
| 12 | c-C$_5$H$_7$ | F | |
| 13 | c-C$_5$H$_9$ | F | |
| 14 | CH$_2$=CH | F | |
| 15 | CH$_3$CH=CH | F | |
| 16 | CH$_2$=CH(CH$_2$)$_2$ | F | |
| 17 | CH$_3$O | F | |
| 18 | C$_2$H$_5$O | F | |
| 19 | n-C$_3$H$_7$O | F | |
| 20 | n-C$_4$H$_9$O | F | |
| 21 | n-C$_5$H$_{11}$O | F | |
| 22 | CH$_3$ | CF$_3$ | |
| 23 | C$_2$H$_5$ | CF$_3$ | |
| 24 | n-C$_3$H$_7$ | CF$_3$ | |
| 25 | n-C$_4$H$_9$ | CF$_3$ | |
| 26 | n-C$_5$H$_{11}$ | CF$_3$ | |
| 27 | n-C$_6$H$_{13}$ | CF$_3$ | |
| 28 | n-C$_7$H$_{15}$ | CF$_3$ | |
| 29 | n-C$_8$H$_{17}$ | CF$_3$ | |
| 30 | c-C$_3$H$_5$ | CF$_3$ | |
| 31 | c-C$_3$H$_5$CH$_2$ | CF$_3$ | |
| 32 | c-C$_4$H$_7$ | CF$_3$ | |
| 33 | c-C$_5$H$_7$ | CF$_3$ | |
| 34 | c-C$_5$H$_9$ | CF$_3$ | |
| 35 | CH$_2$=CH | CF$_3$ | |
| 36 | CH$_3$CH=CH | CF$_3$ | |
| 37 | CH$_2$=CH(CH$_2$)$_2$ | CF$_3$ | |
| 38 | CH$_3$O | CF$_3$ | |
| 39 | C$_2$H$_5$O | CF$_3$ | |
| 40 | n-C$_3$H$_7$O | CF$_3$ | |
| 41 | n-C$_4$H$_9$O | CF$_3$ | Cr 105 SA 113 I; Δn = 0.1591; Δε = 17.7; γ1 = 217 |
| 42 | n-C$_5$H$_{11}$O | CF$_3$ | |
| 43 | CH$_3$ | OCF$_3$ | |
| 44 | C$_2$H$_5$ | OCF$_3$ | |
| 45 | n-C$_3$H$_7$ | OCF$_3$ | |
| 46 | n-C$_4$H$_9$ | OCF$_3$ | |
| 47 | n-C$_5$H$_{11}$ | OCF$_3$ | |
| 48 | n-C$_6$H$_{13}$ | OCF$_3$ | |
| 49 | n-C$_7$H$_{15}$ | OCF$_3$ | |
| 50 | n-C$_8$H$_{17}$ | OCF$_3$ | |
| 51 | c-C$_3$H$_5$ | OCF$_3$ | |
| 52 | c-C$_3$H$_5$CH$_2$ | OCF$_3$ | |
| 53 | c-C$_4$H$_7$ | OCF$_3$ | |
| 54 | c-C$_5$H$_7$ | OCF$_3$ | |
| 55 | c-C$_5$H$_9$ | OCF$_3$ | |
| 56 | CH$_2$=CH | OCF$_3$ | |
| 57 | CH$_3$CH=CH | OCF$_3$ | |
| 58 | CH$_2$=CH(CH$_2$)$_2$ | OCF$_3$ | |
| 59 | CH$_3$O | OCF$_3$ | |
| 60 | C$_2$H$_5$O | OCF$_3$ | |
| 61 | n-C$_3$H$_7$O | OCF$_3$ | |
| 62 | n-C$_4$H$_9$O | OCF$_3$ | Cr 63 I |
| 63 | n-C$_5$H$_{11}$O | OCF$_3$ | |

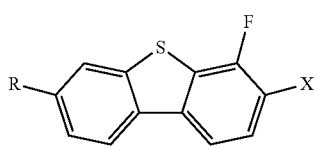

I-4-1

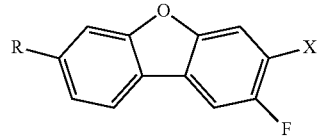

I-5-1

| No: 8- | R | X | Phase Range; properties |
|---|---|---|---|
| 1 | CH$_3$ | F | |
| 2 | C$_2$H$_5$ | F | |
| 3 | n-C$_3$H$_7$ | F | |
| 4 | n-C$_4$H$_9$ | F | |
| 5 | n-C$_5$H$_{11}$ | F | |
| 6 | n-C$_6$H$_{13}$ | F | |
| 7 | n-C$_7$H$_{15}$ | F | |
| 8 | n-C$_8$H$_{17}$ | F | |
| 9 | c-C$_3$H$_5$ | F | |
| 10 | c-C$_3$H$_5$CH$_2$ | F | |
| 11 | c-C$_4$H$_7$ | F | |
| 12 | c-C$_5$H$_7$ | F | |
| 13 | c-C$_5$H$_9$ | F | |
| 14 | CH$_2$=CH | F | |
| 15 | CH$_3$CH=CH | F | |
| 16 | CH$_2$=CH(CH$_2$)$_2$ | F | |
| 17 | CH$_3$O | F | |
| 18 | C$_2$H$_5$O | F | |
| 19 | n-C$_3$H$_7$O | F | |
| 20 | n-C$_4$H$_9$O | F | |
| 21 | n-C$_5$H$_{11}$O | F | |
| 22 | CH$_3$ | CF$_3$ | |
| 23 | C$_2$H$_5$ | CF$_3$ | |
| 24 | n-C$_3$H$_7$ | CF$_3$ | |
| 25 | n-C$_4$H$_9$ | CF$_3$ | |
| 26 | n-C$_5$H$_{11}$ | CF$_3$ | |
| 27 | n-C$_6$H$_{13}$ | CF$_3$ | |
| 28 | n-C$_7$H$_{15}$ | CF$_3$ | |
| 29 | n-C$_8$H$_{17}$ | CF$_3$ | |
| 30 | c-C$_3$H$_5$ | CF$_3$ | |
| 31 | c-C$_3$H$_5$CH$_2$ | CF$_3$ | |
| 32 | c-C$_4$H$_7$ | CF$_3$ | |
| 33 | c-C$_5$H$_7$ | CF$_3$ | |
| 34 | c-C$_5$H$_9$ | CF$_3$ | |
| 35 | CH$_2$=CH | CF$_3$ | |
| 36 | CH$_3$CH=CH | CF$_3$ | |
| 37 | CH$_2$=CH(CH$_2$)$_2$ | CF$_3$ | |
| 38 | CH$_3$O | CF$_3$ | |
| 39 | C$_2$H$_5$O | CF$_3$ | |
| 40 | n-C$_3$H$_7$O | CF$_3$ | |
| 41 | n-C$_4$H$_9$O | CF$_3$ | |
| 42 | n-C$_5$H$_{11}$O | CF$_3$ | |
| 43 | CH$_3$ | OCF$_3$ | |
| 44 | C$_2$H$_5$ | OCF$_3$ | |
| 45 | n-C$_3$H$_7$ | OCF$_3$ | |
| 46 | n-C$_4$H$_9$ | OCF$_3$ | |
| 47 | n-C$_5$H$_{11}$ | OCF$_3$ | |
| 48 | n-C$_6$H$_{13}$ | OCF$_3$ | |
| 49 | n-C$_7$H$_{15}$ | OCF$_3$ | |
| 50 | n-C$_8$H$_{17}$ | OCF$_3$ | |
| 51 | c-C$_3$H$_5$ | OCF$_3$ | |
| 52 | c-C$_3$H$_5$CH$_2$ | OCF$_3$ | |
| 53 | c-C$_4$H$_7$ | OCF$_3$ | |
| 54 | c-C$_5$H$_7$ | OCF$_3$ | |
| 55 | c-C$_5$H$_9$ | OCF$_3$ | |
| 56 | CH$_2$=CH | OCF$_3$ | |
| 57 | CH$_3$CH=CH | OCF$_3$ | |
| 58 | CH$_2$=CH(CH$_2$)$_2$ | OCF$_3$ | |
| 59 | CH$_3$O | OCF$_3$ | |
| 60 | C$_2$H$_5$O | OCF$_3$ | |
| 61 | n-C$_3$H$_7$O | OCF$_3$ | |
| 62 | n-C$_4$H$_9$O | OCF$_3$ | |
| 63 | n-C$_5$H$_{11}$O | OCF$_3$ | |

| No: 9- | R | X | Phase Range; properties |
|---|---|---|---|
| 1 | CH$_3$ | F | |
| 2 | C$_2$H$_5$ | F | |
| 3 | n-C$_3$H$_7$ | F | |
| 4 | n-C$_4$H$_9$ | F | |
| 5 | n-C$_5$H$_{11}$ | F | |
| 6 | n-C$_6$H$_{13}$ | F | |
| 7 | n-C$_7$H$_{15}$ | F | |
| 8 | n-C$_8$H$_{17}$ | F | |
| 9 | c-C$_3$H$_5$ | F | |
| 10 | c-C$_3$H$_5$CH$_2$ | F | |
| 11 | c-C$_4$H$_7$ | F | |
| 12 | c-C$_5$H$_7$ | F | |
| 13 | c-C$_5$H$_9$ | F | |
| 14 | CH$_2$=CH | F | |
| 15 | CH$_3$CH=CH | F | |
| 16 | CH$_2$=CH(CH$_2$)$_2$ | F | |
| 17 | CH$_3$O | F | |
| 18 | C$_2$H$_5$O | F | |
| 19 | n-C$_3$H$_7$O | F | |
| 20 | n-C$_4$H$_9$O | F | |
| 21 | n-C$_5$H$_{11}$O | F | |
| 22 | CH$_3$ | CF$_3$ | |
| 23 | C$_2$H$_5$ | CF$_3$ | |
| 24 | n-C$_3$H$_7$ | CF$_3$ | |
| 25 | n-C$_4$H$_9$ | CF$_3$ | |
| 26 | n-C$_5$H$_{11}$ | CF$_3$ | |
| 27 | n-C$_6$H$_{13}$ | CF$_3$ | |
| 28 | n-C$_7$H$_{15}$ | CF$_3$ | |
| 29 | n-C$_8$H$_{17}$ | CF$_3$ | |
| 30 | c-C$_3$H$_5$ | CF$_3$ | |
| 31 | c-C$_3$H$_5$CH$_2$ | CF$_3$ | |
| 32 | c-C$_4$H$_7$ | CF$_3$ | |
| 33 | c-C$_5$H$_7$ | CF$_3$ | |
| 34 | c-C$_5$H$_9$ | CF$_3$ | |
| 35 | CH$_2$=CH | CF$_3$ | |
| 36 | CH$_3$CH=CH | CF$_3$ | |
| 37 | CH$_2$=CH(CH$_2$)$_2$ | CF$_3$ | |
| 38 | CH$_3$O | CF$_3$ | |
| 39 | C$_2$H$_5$O | CF$_3$ | |
| 40 | n-C$_3$H$_7$O | CF$_3$ | |
| 41 | n-C$_4$H$_9$O | CF$_3$ | |
| 42 | n-C$_5$H$_{11}$O | CF$_3$ | |
| 43 | CH$_3$ | OCF$_3$ | |
| 44 | C$_2$H$_5$ | OCF$_3$ | |
| 45 | n-C$_3$H$_7$ | OCF$_3$ | |
| 46 | n-C$_4$H$_9$ | OCF$_3$ | |
| 47 | n-C$_5$H$_{11}$ | OCF$_3$ | |
| 48 | n-C$_6$H$_{13}$ | OCF$_3$ | |
| 49 | n-C$_7$H$_{15}$ | OCF$_3$ | |
| 50 | n-C$_8$H$_{17}$ | OCF$_3$ | |
| 51 | c-C$_3$H$_5$ | OCF$_3$ | |
| 52 | c-C$_3$H$_5$CH$_2$ | OCF$_3$ | |
| 53 | c-C$_4$H$_7$ | OCF$_3$ | |
| 54 | c-C$_5$H$_7$ | OCF$_3$ | |
| 55 | c-C$_5$H$_9$ | OCF$_3$ | |
| 56 | CH$_2$=CH | OCF$_3$ | |
| 57 | CH$_3$CH=CH | OCF$_3$ | |
| 58 | CH$_2$=CH(CH$_2$)$_2$ | OCF$_3$ | |
| 59 | CH$_3$O | OCF$_3$ | |
| 60 | C$_2$H$_5$O | OCF$_3$ | |
| 61 | n-C$_3$H$_7$O | OCF$_3$ | |
| 62 | n-C$_4$H$_9$O | OCF$_3$ | |
| 63 | n-C$_5$H$_{11}$O | OCF$_3$ | |

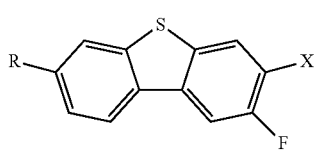

I-6-1

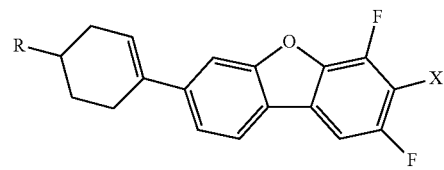

I-1-2

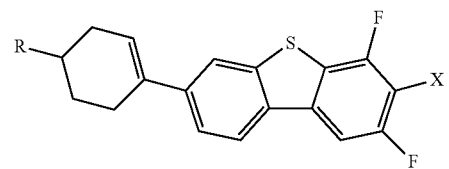

I-2-2

| No: 10- | R | X | Phase Range; properties |
|---|---|---|---|
| 1 | $CH_3$ | F | |
| 2 | $C_2H_5$ | F | |
| 3 | $n-C_3H_7$ | F | Cr 85 N 94.3 I; $\Delta n$ = 0.2090; $\Delta\varepsilon$ = 9.7; $\gamma_1$ =366 |
| 4 | $n-C_4H_9$ | F | |
| 5 | $n-C_5H_{11}$ | F | |
| 6 | $n-C_6H_{13}$ | F | |
| 7 | $n-C_7H_{15}$ | F | |
| 8 | $n-C_8H_{17}$ | F | |
| 9 | $c-C_3H_5$ | F | |
| 10 | $c-C_3H_5CH_2$ | F | |
| 11 | $c-C_4H_7$ | F | |
| 12 | $c-C_5H_7$ | F | |
| 13 | $c-C_5H_9$ | F | |
| 14 | $CH_2=CH$ | F | |
| 15 | $CH_3CH=CH$ | F | |
| 16 | $CH_2=CH(CH_2)_2$ | F | |
| 17 | $CH_3O$ | F | |
| 18 | $C_2H_5O$ | F | |
| 19 | $n-C_3H_7O$ | F | |
| 20 | $n-C_4H_9O$ | F | |
| 21 | $n-C_5H_{11}O$ | F | |
| 22 | $CH_3$ | $CF_3$ | |
| 23 | $C_2H_5$ | $CF_3$ | |
| 24 | $n-C_3H_7$ | $CF_3$ | Tg −35 Cr 67 SX (33) SA (40) I; $\Delta n$ = 0.2036; $\Delta\varepsilon$ = 18.5 |
| 25 | $n-C_4H_9$ | $CF_3$ | |
| 26 | $n-C_5H_{11}$ | $CF_3$ | |
| 27 | $n-C_6H_{13}$ | $CF_3$ | |
| 28 | $n-C_7H_{15}$ | $CF_3$ | |
| 29 | $n-C_8H_{17}$ | $CF_3$ | |
| 30 | $c-C_3H_5$ | $CF_3$ | |
| 31 | $c-C_3H_5CH_2$ | $CF_3$ | |
| 32 | $c-C_4H_7$ | $CF_3$ | |
| 33 | $c-C_5H_7$ | $CF_3$ | |
| 34 | $c-C_5H_9$ | $CF_3$ | |
| 35 | $CH_2=CH$ | $CF_3$ | |
| 36 | $CH_3CH=CH$ | $CF_3$ | |
| 37 | $CH_2=CH(CH_2)_2$ | $CF_3$ | |
| 38 | $CH_3O$ | $CF_3$ | |
| 39 | $C_2H_5O$ | $CF_3$ | |
| 40 | $n-C_3H_7O$ | $CF_3$ | |
| 41 | $n-C_4H_9O$ | $CF_3$ | |
| 42 | $n-C_5H_{11}O$ | $CF_3$ | |
| 43 | $CH_3$ | $OCF_3$ | |
| 44 | $C_2H_5$ | $OCF_3$ | |
| 45 | $n-C_3H_7$ | $OCF_3$ | Cr 75 SA 75 N 86 I; $\Delta n$ = 0.1341; $\Delta\varepsilon$ = 13.3; $\gamma_1$ =424 |
| 46 | $n-C_4H_9$ | $OCF_3$ | |
| 47 | $n-C_5H_{11}$ | $OCF_3$ | |
| 48 | $n-C_6H_{13}$ | $OCF_3$ | |
| 49 | $n-C_7H_{15}$ | $OCF_3$ | |
| 50 | $n-C_8H_{17}$ | $OCF_3$ | |
| 51 | $c-C_3H_5$ | $OCF_3$ | |
| 52 | $c-C_3H_5CH_2$ | $OCF_3$ | |
| 53 | $c-C_4H_7$ | $OCF_3$ | |
| 54 | $c-C_5H_7$ | $OCF_3$ | |
| 55 | $c-C_5H_9$ | $OCF_3$ | |
| 56 | $CH_2=CH$ | $OCF_3$ | |
| 57 | $CH_3CH=CH$ | $OCF_3$ | |
| 58 | $CH_2=CH(CH_2)_2$ | $OCF_3$ | |
| 59 | $CH_3O$ | $OCF_3$ | |
| 60 | $C_2H_5O$ | $OCF_3$ | |
| 61 | $n-C_3H_7O$ | $OCF_3$ | |
| 62 | $n-C_4H_9O$ | $OCF_3$ | |
| 63 | $n-C_5H_{11}O$ | $OCF_3$ | |

| No: 11- | R | X | Phase Range; properties |
|---|---|---|---|
| 1 | $CH_3$ | F | |
| 2 | $C_2H_5$ | F | |
| 3 | $n-C_3H_7$ | F | |
| 4 | $n-C_4H_9$ | F | |
| 5 | $n-C_5H_{11}$ | F | |
| 6 | $n-C_6H_{13}$ | F | |
| 7 | $n-C_7H_{15}$ | F | |
| 8 | $n-C_8H_{17}$ | F | |
| 9 | $c-C_3H_5$ | F | |
| 10 | $c-C_3H_5CH_2$ | F | |
| 11 | $c-C_4H_7$ | F | |
| 12 | $c-C_5H_7$ | F | |
| 13 | $c-C_5H_9$ | F | |
| 14 | $CH_2=CH$ | F | |
| 15 | $CH_3CH=CH$ | F | |
| 16 | $CH_2=CH(CH_2)_2$ | F | |
| 17 | $CH_3O$ | F | |
| 18 | $C_2H_5O$ | F | |
| 19 | $n-C_3H_7O$ | F | |
| 20 | $n-C_4H_9O$ | F | |
| 21 | $n-C_5H_{11}O$ | F | |
| 22 | $CH_3$ | $CF_3$ | |
| 23 | $C_2H_5$ | $CF_3$ | |
| 24 | $n-C_3H_7$ | $CF_3$ | Cr 150 $S_X$ 116 I; $\Delta n$ = 0.2101; $\Delta\varepsilon$ = 22.9; $\gamma_1$ = 635 |
| 25 | $n-C_4H_9$ | $CF_3$ | |
| 26 | $n-C_5H_{11}$ | $CF_3$ | |
| 27 | $n-C_6H_{13}$ | $CF_3$ | |
| 28 | $n-C_7H_{15}$ | $CF_3$ | |
| 29 | $n-C_8H_{17}$ | $CF_3$ | |
| 30 | $c-C_3H_5$ | $CF_3$ | |
| 31 | $c-C_3H_5CH_2$ | $CF_3$ | |
| 32 | $c-C_4H_7$ | $CF_3$ | |
| 33 | $c-C_5H_7$ | $CF_3$ | |
| 34 | $c-C_5H_9$ | $CF_3$ | |
| 35 | $CH_2=CH$ | $CF_3$ | |
| 36 | $CH_3CH=CH$ | $CF_3$ | |
| 37 | $CH_2=CH(CH_2)_2$ | $CF_3$ | |
| 38 | $CH_3O$ | $CF_3$ | |
| 39 | $C_2H_5O$ | $CF_3$ | |
| 40 | $n-C_3H_7O$ | $CF_3$ | |
| 41 | $n-C_4H_9O$ | $CF_3$ | |
| 42 | $n-C_5H_{11}O$ | $CF_3$ | |
| 43 | $CH_3$ | $OCF_3$ | |
| 44 | $C_2H_5$ | $OCF_3$ | |
| 45 | $n-C_3H_7$ | $OCF_3$ | |
| 46 | $n-C_4H_9$ | $OCF_3$ | |
| 47 | $n-C_5H_{11}$ | $OCF_3$ | |
| 48 | $n-C_6H_{13}$ | $OCF_3$ | |
| 49 | $n-C_7H_{15}$ | $OCF_3$ | |
| 50 | $n-C_8H_{17}$ | $OCF_3$ | |
| 51 | $c-C_3H_5$ | $OCF_3$ | |
| 52 | $c-C_3H_5CH_2$ | $OCF_3$ | |
| 53 | $c-C_4H_7$ | $OCF_3$ | |
| 54 | $c-C_5H_7$ | $OCF_3$ | |
| 55 | $c-C_5H_9$ | $OCF_3$ | |
| 56 | $CH_2=CH$ | $OCF_3$ | |
| 57 | $CH_3CH=CH$ | $OCF_3$ | |
| 58 | $CH_2=CH(CH_2)_2$ | $OCF_3$ | |
| 59 | $CH_3O$ | $OCF_3$ | |
| 60 | $C_2H_5O$ | $OCF_3$ | |
| 61 | $n-C_3H_7O$ | $OCF_3$ | |
| 62 | $n-C_4H_9O$ | $OCF_3$ | |
| 63 | $n-C_5H_{11}O$ | $OCF_3$ | |

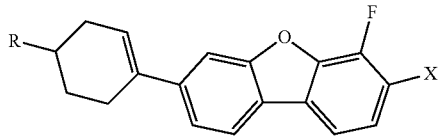

I-3-2

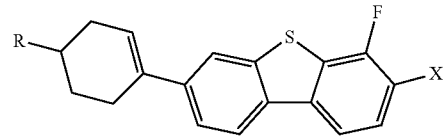

I-4-2

| No:12- | R | X | Phase Range; properties |
|---|---|---|---|
| 1 | CH$_3$ | F | |
| 2 | C$_2$H$_5$ | F | |
| 3 | n-C$_3$H$_7$ | F | |
| 4 | n-C$_4$H$_9$ | F | |
| 5 | n-C$_5$H$_{11}$ | F | |
| 6 | n-C$_6$H$_{13}$ | F | |
| 7 | n-C$_7$H$_{15}$ | F | |
| 8 | n-C$_8$H$_{17}$ | F | |
| 9 | c-C$_3$H$_5$ | F | |
| 10 | c-C$_3$H$_5$CH$_2$ | F | |
| 11 | c-C$_4$H$_7$ | F | |
| 12 | c-C$_5$H$_7$ | F | |
| 13 | c-C$_5$H$_9$ | F | |
| 14 | CH$_2$=CH | F | |
| 15 | CH$_3$CH=CH | F | |
| 16 | CH$_2$=CH(CH$_2$)$_2$ | F | |
| 17 | CH$_3$O | F | |
| 18 | C$_2$H$_5$O | F | |
| 19 | n-C$_3$H$_7$O | F | |
| 20 | n-C$_4$H$_9$O | F | |
| 21 | n-C$_5$H$_{11}$O | F | |
| 22 | CH$_3$ | CF$_3$ | |
| 23 | C$_2$H$_5$ | CF$_3$ | |
| 24 | n-C$_3$H$_7$ | CF$_3$ | Cr 85 S$_A$ 108 I; Δn = 0.2168; Δε = 9.5; γ$_1$ = 462 |
| 25 | n-C$_4$H$_9$ | CF$_3$ | |
| 26 | n-C$_5$H$_{11}$ | CF$_3$ | |
| 27 | n-C$_6$H$_{13}$ | CF$_3$ | |
| 28 | n-C$_7$H$_{15}$ | CF$_3$ | |
| 29 | n-C$_8$H$_{17}$ | CF$_3$ | |
| 30 | c-C$_3$H$_5$ | CF$_3$ | |
| 31 | c-C$_3$H$_5$CH$_2$ | CF$_3$ | |
| 32 | c-C$_4$H$_7$ | CF$_3$ | |
| 33 | c-C$_5$H$_7$ | CF$_3$ | |
| 34 | c-C$_5$H$_9$ | CF$_3$ | |
| 35 | CH$_2$=CH | CF$_3$ | |
| 36 | CH$_3$CH=CH | CF$_3$ | |
| 37 | CH$_2$=CH(CH$_2$)$_2$ | CF$_3$ | |
| 38 | CH$_3$O | CF$_3$ | |
| 39 | C$_2$H$_5$O | CF$_3$ | |
| 40 | n-C$_3$H$_7$O | CF$_3$ | |
| 41 | n-C$_4$H$_9$O | CF$_3$ | |
| 42 | n-C$_5$H$_{11}$O | CF$_3$ | |
| 43 | CH$_3$ | OCF$_3$ | |
| 44 | C$_2$H$_5$ | OCF$_3$ | |
| 45 | n-C$_3$H$_7$ | OCF$_3$ | Cr 83 S$_A$ 132 I; Δn = 0.2068; Δε = 6.2; γ$_1$ = 338 |
| 46 | n-C$_4$H$_9$ | OCF$_3$ | |
| 47 | n-C$_5$H$_{11}$ | OCF$_3$ | |
| 48 | n-C$_6$H$_{13}$ | OCF$_3$ | |
| 49 | n-C$_7$H$_{15}$ | OCF$_3$ | |
| 50 | n-C$_8$H$_{17}$ | OCF$_3$ | |
| 51 | c-C$_3$H$_5$ | OCF$_3$ | |
| 52 | c-C$_3$H$_5$CH$_2$ | OCF$_3$ | |
| 53 | c-C$_4$H$_7$ | OCF$_3$ | |
| 54 | c-C$_5$H$_7$ | OCF$_3$ | |
| 55 | c-C$_5$H$_9$ | OCF$_3$ | |
| 56 | CH$_2$=CH | OCF$_3$ | |
| 57 | CH$_3$CH=CH | OCF$_3$ | |
| 58 | CH$_2$=CH(CH$_2$)$_2$ | OCF$_3$ | |
| 59 | CH$_3$O | OCF$_3$ | |
| 60 | C$_2$H$_5$O | OCF$_3$ | |
| 61 | n-C$_3$H$_7$O | OCF$_3$ | |
| 62 | n-C$_4$H$_9$O | OCF$_3$ | Cr 63 I |
| 63 | n-C$_5$H$_{11}$O | OCF$_3$ | |

| No: 13- | R | X | Phase Range; properties |
|---|---|---|---|
| 1 | CH$_3$ | F | |
| 2 | C$_2$H$_5$ | F | |
| 3 | n-C$_3$H$_7$ | F | |
| 4 | n-C$_4$H$_9$ | F | |
| 5 | n-C$_5$H$_{11}$ | F | |
| 6 | n-C$_6$H$_{13}$ | F | |
| 7 | n-C$_7$H$_{15}$ | F | |
| 8 | n-C$_8$H$_{17}$ | F | |
| 9 | c-C$_3$H$_5$ | F | |
| 10 | c-C$_3$H$_5$CH$_2$ | F | |
| 11 | c-C$_4$H$_7$ | F | |
| 12 | c-C$_5$H$_7$ | F | |
| 13 | c-C$_5$H$_9$ | F | |
| 14 | CH$_2$=CH | F | |
| 15 | CH$_3$CH=CH | F | |
| 16 | CH$_2$=CH(CH$_2$)$_2$ | F | |
| 17 | CH$_3$O | F | |
| 18 | C$_2$H$_5$O | F | |
| 19 | n-C$_3$H$_7$O | F | |
| 20 | n-C$_4$H$_9$O | F | |
| 21 | n-C$_5$H$_{11}$O | F | |
| 22 | CH$_3$ | CF$_3$ | |
| 23 | C$_2$H$_5$ | CF$_3$ | |
| 24 | n-C$_3$H$_7$ | CF$_3$ | Cr 142 S$_A$ 181 I; Δn = 0.2251; Δε = 16.1; γ$_1$ = 750 |
| 25 | n-C$_4$H$_9$ | CF$_3$ | |
| 26 | n-C$_5$H$_{11}$ | CF$_3$ | |
| 27 | n-C$_6$H$_{13}$ | CF$_3$ | |
| 28 | n-C$_7$H$_{15}$ | CF$_3$ | |
| 29 | n-C$_8$H$_{17}$ | CF$_3$ | |
| 30 | c-C$_3$H$_5$ | CF$_3$ | |
| 31 | c-C$_3$H$_5$CH$_2$ | CF$_3$ | |
| 32 | c-C$_4$H$_7$ | CF$_3$ | |
| 33 | c-C$_5$H$_7$ | CF$_3$ | |
| 34 | c-C$_5$H$_9$ | CF$_3$ | |
| 35 | CH$_2$=CH | CF$_3$ | |
| 36 | CH$_3$CH=CH | CF$_3$ | |
| 37 | CH$_2$=CH(CH$_2$)$_2$ | CF$_3$ | |
| 38 | CH$_3$O | CF$_3$ | |
| 39 | C$_2$H$_5$O | CF$_3$ | |
| 40 | n-C$_3$H$_7$O | CF$_3$ | |
| 41 | n-C$_4$H$_9$O | CF$_3$ | |
| 42 | n-C$_5$H$_{11}$O | CF$_3$ | |
| 43 | CH$_3$ | OCF$_3$ | |
| 44 | C$_2$H$_5$ | OCF$_3$ | |
| 45 | n-C$_3$H$_7$ | OCF$_3$ | Cr 101 S$_A$ 194 I; Δn = 0.2143; Δε = 10.8; γ$_1$ = 556 |
| 46 | n-C$_4$H$_9$ | OCF$_3$ | |
| 47 | n-C$_5$H$_{11}$ | OCF$_3$ | |
| 48 | n-C$_6$H$_{13}$ | OCF$_3$ | |
| 49 | n-C$_7$H$_{15}$ | OCF$_3$ | |
| 50 | n-C$_8$H$_{17}$ | OCF$_3$ | |
| 51 | c-C$_3$H$_5$ | OCF$_3$ | |
| 52 | c-C$_3$H$_5$CH$_2$ | OCF$_3$ | |
| 53 | c-C$_4$H$_7$ | OCF$_3$ | |
| 54 | c-C$_5$H$_7$ | OCF$_3$ | |
| 55 | c-C$_5$H$_9$ | OCF$_3$ | |
| 56 | CH$_2$=CH | OCF$_3$ | |
| 57 | CH$_3$CH=CH | OCF$_3$ | |
| 58 | CH$_2$=CH(CH$_2$)$_2$ | OCF$_3$ | |
| 59 | CH$_3$O | OCF$_3$ | |
| 60 | C$_2$H$_5$O | OCF$_3$ | |
| 61 | n-C$_3$H$_7$O | OCF$_3$ | |
| 62 | n-C$_4$H$_9$O | OCF$_3$ | |
| 63 | n-C$_5$H$_{11}$O | OCF$_3$ | |

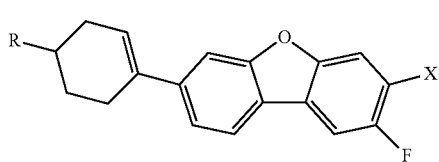

I-5-2

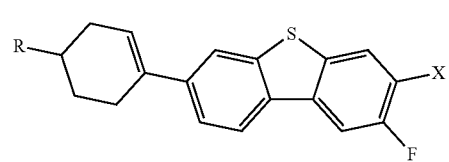

I-6-2

| No: 14- | R | X | Phase Range; properties |
|---|---|---|---|
| 1 | CH₃ | F | |
| 2 | C₂H₅ | F | |
| 3 | n-C₃H₇ | F | |
| 4 | n-C₄H₉ | F | |
| 5 | n-C₅H₁₁ | F | |
| 6 | n-C₆H₁₃ | F | |
| 7 | n-C₇H₁₅ | F | |
| 8 | n-C₈H₁₇ | F | |
| 9 | c-C₃H₅ | F | |
| 10 | c-C₃H₅CH₂ | F | |
| 11 | c-C₄H₇ | F | |
| 12 | c-C₅H₇ | F | |
| 13 | c-C₅H₉ | F | |
| 14 | CH₂=CH | F | |
| 15 | CH₃CH=CH | F | |
| 16 | CH₂=CH(CH₂)₂ | F | |
| 17 | CH₃O | F | |
| 18 | C₂H₅O | F | |
| 19 | n-C₃H₇O | F | |
| 20 | n-C₄H₉O | F | |
| 21 | n-C₅H₁₁O | F | |
| 22 | CH₃ | CF₃ | |
| 23 | C₂H₅ | CF₃ | |
| 24 | n-C₃H₇ | CF₃ | |
| 25 | n-C₄H₉ | CF₃ | |
| 26 | n-C₅H₁₁ | CF₃ | |
| 27 | n-C₆H₁₃ | CF₃ | |
| 28 | n-C₇H₁₅ | CF₃ | |
| 29 | n-C₈H₁₇ | CF₃ | |
| 30 | c-C₃H₅ | CF₃ | |
| 31 | c-C₃H₅CH₂ | CF₃ | |
| 32 | c-C₄H₇ | CF₃ | |
| 33 | c-C₅H₇ | CF₃ | |
| 34 | c-C₅H₉ | CF₃ | |
| 35 | CH₂=CH | CF₃ | |
| 36 | CH₃CH=CH | CF₃ | |
| 37 | CH₂=CH(CH₂)₂ | CF₃ | |
| 38 | CH₃O | CF₃ | |
| 39 | C₂H₅O | CF₃ | |
| 40 | n-C₃H₇O | CF₃ | |
| 41 | n-C₄H₉O | CF₃ | |
| 42 | n-C₅H₁₁O | CF₃ | |
| 43 | CH₃ | OCF₃ | |
| 44 | C₂H₅ | OCF₃ | |
| 45 | n-C₃H₇ | OCF₃ | |
| 46 | n-C₄H₉ | OCF₃ | |
| 47 | n-C₅H₁₁ | OCF₃ | |
| 48 | n-C₆H₁₃ | OCF₃ | |
| 49 | n-C₇H₁₅ | OCF₃ | |
| 50 | n-C₈H₁₇ | OCF₃ | |
| 51 | c-C₃H₅ | OCF₃ | |
| 52 | c-C₃H₅CH₂ | OCF₃ | |
| 53 | c-C₄H₇ | OCF₃ | |
| 54 | c-C₅H₇ | OCF₃ | |
| 55 | c-C₅H₉ | OCF₃ | |
| 56 | CH₂=CH | OCF₃ | |
| 57 | CH₃CH=CH | OCF₃ | |
| 58 | CH₂=CH(CH₂)₂ | OCF₃ | |
| 59 | CH₃O | OCF₃ | |
| 60 | C₂H₅O | OCF₃ | |
| 61 | n-C₃H₇O | OCF₃ | |
| 62 | n-C₄H₉O | OCF₃ | |
| 63 | n-C₅H₁₁O | OCF₃ | |

| No: 15- | R | X | Phase Range; properties |
|---|---|---|---|
| 1 | CH₃ | F | |
| 2 | C₂H₅ | F | |
| 3 | n-C₃H₇ | F | |
| 4 | n-C₄H₉ | F | |
| 5 | n-C₅H₁₁ | F | |
| 6 | n-C₆H₁₃ | F | |
| 7 | n-C₇H₁₅ | F | |
| 8 | n-C₈H₁₇ | F | |
| 9 | c-C₃H₅ | F | |
| 10 | c-C₃H₅CH₂ | F | |
| 11 | c-C₄H₇ | F | |
| 12 | c-C₅H₇ | F | |
| 13 | c-C₅H₉ | F | |
| 14 | CH₂=CH | F | |
| 15 | CH₃CH=CH | F | |
| 16 | CH₂=CH(CH₂)₂ | F | |
| 17 | CH₃O | F | |
| 18 | C₂H₅O | F | |
| 19 | n-C₃H₇O | F | |
| 20 | n-C₄H₉O | F | |
| 21 | n-C₅H₁₁O | F | |
| 22 | CH₃ | CF₃ | |
| 23 | C₂H₅ | CF₃ | |
| 24 | n-C₃H₇ | CF₃ | |
| 25 | n-C₄H₉ | CF₃ | |
| 26 | n-C₅H₁₁ | CF₃ | |
| 27 | n-C₆H₁₃ | CF₃ | |
| 28 | n-C₇H₁₅ | CF₃ | |
| 29 | n-C₈H₁₇ | CF₃ | |
| 30 | c-C₃H₅ | CF₃ | |
| 31 | c-C₃H₅CH₂ | CF₃ | |
| 32 | c-C₄H₇ | CF₃ | |
| 33 | c-C₅H₇ | CF₃ | |
| 34 | c-C₅H₉ | CF₃ | |
| 35 | CH₂=CH | CF₃ | |
| 36 | CH₃CH=CH | CF₃ | |
| 37 | CH₂=CH(CH₂)₂ | CF₃ | |
| 38 | CH₃O | CF₃ | |
| 39 | C₂H₅O | CF₃ | |
| 40 | n-C₃H₇O | CF₃ | |
| 41 | n-C₄H₉O | CF₃ | |
| 42 | n-C₅H₁₁O | CF₃ | |
| 43 | CH₃ | OCF₃ | |
| 44 | C₂H₅ | OCF₃ | |
| 45 | n-C₃H₇ | OCF₃ | |
| 46 | n-C₄H₉ | OCF₃ | |
| 47 | n-C₅H₁₁ | OCF₃ | |
| 48 | n-C₆H₁₃ | OCF₃ | |
| 49 | n-C₇H₁₅ | OCF₃ | |
| 50 | n-C₈H₁₇ | OCF₃ | |
| 51 | c-C₃H₅ | OCF₃ | |
| 52 | c-C₃H₅CH₂ | OCF₃ | |
| 53 | c-C₄H₇ | OCF₃ | |
| 54 | c-C₅H₇ | OCF₃ | |
| 55 | c-C₅H₉ | OCF₃ | |
| 56 | CH₂=CH | OCF₃ | |
| 57 | CH₃CH=CH | OCF₃ | |
| 58 | CH₂=CH(CH₂)₂ | OCF₃ | |
| 59 | CH₃O | OCF₃ | |
| 60 | C₂H₅O | OCF₃ | |
| 61 | n-C₃H₇O | OCF₃ | |
| 62 | n-C₄H₉O | OCF₃ | |
| 63 | n-C₅H₁₁O | OCF₃ | |

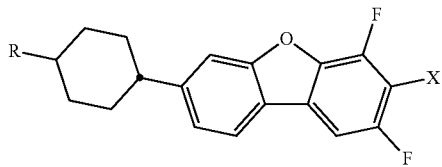

I-1-3

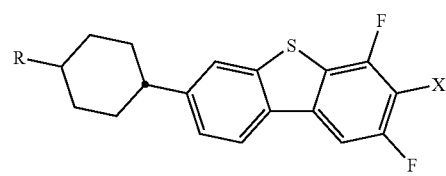

I-2-3

| No: 16- | R^(1X) | X | Phase Range; properties |
|---|---|---|---|
| 1 | $CH_3$ | F | |
| 2 | $C_2H_5$ | F | |
| 3 | $n-C_3H_7$ | F | |
| 4 | $n-C_4H_9$ | F | |
| 5 | $n-C_5H_{11}$ | F | |
| 6 | $n-C_6H_{13}$ | F | |
| 7 | $n-C_7H_{15}$ | F | |
| 8 | $n-C_8H_{17}$ | F | |
| 9 | $c-C_3H_5$ | F | |
| 10 | $c-C_3H_5CH_2$ | F | |
| 11 | $c-C_4H_7$ | F | |
| 12 | $c-C_5H_7$ | F | |
| 13 | $c-C_5H_9$ | F | |
| 14 | $CH_2=CH$ | F | |
| 15 | $CH_3CH=CH$ | F | |
| 16 | $CH_2=CH(CH_2)_2$ | F | |
| 17 | $CH_3O$ | F | |
| 18 | $C_2H_5O$ | F | |
| 19 | $n-C_3H_7O$ | F | |
| 20 | $n-C_4H_9O$ | F | |
| 21 | $n-C_5H_{11}O$ | F | |
| 22 | $CH_3$ | $CF_3$ | |
| 23 | $C_2H_5$ | $CF_3$ | |
| 24 | $n-C_3H_7$ | $CF_3$ | $T_g$ −35 Cr 67 $S_X$ (33 $S_A$ 40) I; $\Delta n = 0.2036$; $\Delta\varepsilon = 18.5$; $\gamma_1 = 518$ |
| 25 | $n-C_4H_9$ | $CF_3$ | |
| 26 | $n-C_5H_{11}$ | $CF_3$ | |
| 27 | $n-C_6H_{13}$ | $CF_3$ | |
| 28 | $n-C_7H_{15}$ | $CF_3$ | |
| 29 | $n-C_8H_{17}$ | $CF_3$ | |
| 30 | $c-C_3H_5$ | $CF_3$ | |
| 31 | $c-C_3H_5CH_2$ | $CF_3$ | |
| 32 | $c-C_4H_7$ | $CF_3$ | |
| 33 | $c-C_5H_7$ | $CF_3$ | |
| 34 | $c-C_5H_9$ | $CF_3$ | |
| 35 | $CH_2=CH$ | $CF_3$ | |
| 36 | $CH_3CH=CH$ | $CF_3$ | |
| 37 | $CH_2=CH(CH_2)_2$ | $CF_3$ | |
| 38 | $CH_3O$ | $CF_3$ | |
| 39 | $C_2H_5O$ | $CF_3$ | |
| 40 | $n-C_3H_7O$ | $CF_3$ | |
| 41 | $n-C_4H_9O$ | $CF_3$ | |
| 42 | $n-C_5H_{11}O$ | $CF_3$ | |
| 43 | $CH_3$ | $OCF_3$ | |
| 44 | $C_2H_5$ | $OCF_3$ | |
| 45 | $n-C_3H_7$ | $OCF_3$ | |
| 46 | $n-C_4H_9$ | $OCF_3$ | |
| 47 | $n-C_5H_{11}$ | $OCF_3$ | |
| 48 | $n-C_6H_{13}$ | $OCF_3$ | |
| 49 | $n-C_7H_{15}$ | $OCF_3$ | |
| 50 | $n-C_8H_{17}$ | $OCF_3$ | |
| 51 | $c-C_3H_5$ | $OCF_3$ | |
| 52 | $c-C_3H_5CH_2$ | $OCF_3$ | |
| 53 | $c-C_4H_7$ | $OCF_3$ | |
| 54 | $c-C_5H_7$ | $OCF_3$ | |
| 55 | $c-C_5H_9$ | $OCF_3$ | |
| 56 | $CH_2=CH$ | $OCF_3$ | |
| 57 | $CH_3CH=CH$ | $OCF_3$ | |
| 58 | $CH_2=CH(CH_2)_2$ | $OCF_3$ | |
| 59 | $CH_3O$ | $OCF_3$ | |
| 60 | $C_2H_5O$ | $OCF_3$ | |
| 61 | $n-C_3H_7O$ | $OCF_3$ | |
| 62 | $n-C_4H_9O$ | $OCF_3$ | |
| 63 | $n-C_5H_{11}O$ | $OCF_3$ | |

| No: 17- | R | X | Phase Range; properties |
|---|---|---|---|
| 1 | $CH_3$ | F | |
| 2 | $C_2H_5$ | F | |
| 3 | $n-C_3H_7$ | F | |
| 4 | $n-C_4H_9$ | F | |
| 5 | $n-C_5H_{11}$ | F | |
| 6 | $n-C_6H_{13}$ | F | |
| 7 | $n-C_7H_{15}$ | F | |
| 8 | $n-C_8H_{17}$ | F | |
| 9 | $c-C_3H_5$ | F | |
| 10 | $c-C_3H_5CH_2$ | F | |
| 11 | $c-C_4H_7$ | F | |
| 12 | $c-C_5H_7$ | F | |
| 13 | $c-C_5H_9$ | F | |
| 14 | $CH_2=CH$ | F | |
| 15 | $CH_3CH=CH$ | F | |
| 16 | $CH_2=CH(CH_2)_2$ | F | |
| 17 | $CH_3O$ | F | |
| 18 | $C_2H_5O$ | F | |
| 19 | $n-C_3H_7O$ | F | |
| 20 | $n-C_4H_9O$ | F | |
| 21 | $n-C_5H_{11}O$ | F | |
| 22 | $CH_3$ | $CF_3$ | |
| 23 | $C_2H_5$ | $CF_3$ | |
| 24 | $n-C_3H_7$ | $CF_3$ | |
| 25 | $n-C_4H_9$ | $CF_3$ | |
| 26 | $n-C_5H_{11}$ | $CF_3$ | |
| 27 | $n-C_6H_{13}$ | $CF_3$ | |
| 28 | $n-C_7H_{15}$ | $CF_3$ | |
| 29 | $n-C_8H_{17}$ | $CF_3$ | |
| 30 | $c-C_3H_5$ | $CF_3$ | |
| 31 | $c-C_3H_5CH_2$ | $CF_3$ | |
| 32 | $c-C_4H_7$ | $CF_3$ | |
| 33 | $c-C_5H_7$ | $CF_3$ | |
| 34 | $c-C_5H_9$ | $CF_3$ | |
| 35 | $CH_2=CH$ | $CF_3$ | |
| 36 | $CH_3CH=CH$ | $CF_3$ | |
| 37 | $CH_2=CH(CH_2)_2$ | $CF_3$ | |
| 38 | $CH_3O$ | $CF_3$ | |
| 39 | $C_2H_5O$ | $CF_3$ | |
| 40 | $n-C_3H_7O$ | $CF_3$ | |
| 41 | $n-C_4H_9O$ | $CF_3$ | |
| 42 | $n-C_5H_{11}O$ | $CF_3$ | |
| 43 | $CH_3$ | $OCF_3$ | |
| 44 | $C_2H_5$ | $OCF_3$ | |
| 45 | $n-C_3H_7$ | $OCF_3$ | |
| 46 | $n-C_4H_9$ | $OCF_3$ | |
| 47 | $n-C_5H_{11}$ | $OCF_3$ | |
| 48 | $n-C_6H_{13}$ | $OCF_3$ | |
| 49 | $n-C_7H_{15}$ | $OCF_3$ | |
| 50 | $n-C_8H_{17}$ | $OCF_3$ | |
| 51 | $c-C_3H_5$ | $OCF_3$ | |
| 52 | $c-C_3H_5CH_2$ | $OCF_3$ | |
| 53 | $c-C_4H_7$ | $OCF_3$ | |
| 54 | $c-C_5H_7$ | $OCF_3$ | |
| 55 | $c-C_5H_9$ | $OCF_3$ | |
| 56 | $CH_2=CH$ | $OCF_3$ | |
| 57 | $CH_3CH=CH$ | $OCF_3$ | |
| 58 | $CH_2=CH(CH_2)_2$ | $OCF_3$ | |
| 59 | $CH_3O$ | $OCF_3$ | |
| 60 | $C_2H_5O$ | $OCF_3$ | |
| 61 | $n-C_3H_7O$ | $OCF_3$ | |
| 62 | $n-C_4H_9O$ | $OCF_3$ | |
| 63 | $n-C_5H_{11}O$ | $OCF_3$ | |

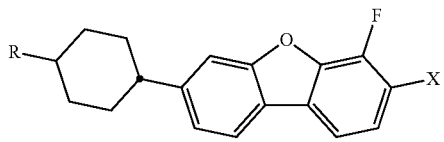

I-3-3

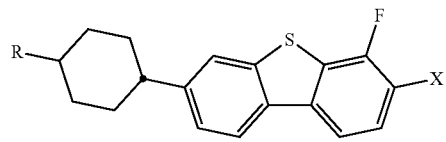

I-4-3

| No: 18- | R | X | Phase Range; properties |
|---|---|---|---|
| 1 | CH₃ | F | |
| 2 | C₂H₅ | F | |
| 3 | n-C₃H₇ | F | |
| 4 | n-C₄H₉ | F | |
| 5 | n-C₅H₁₁ | F | |
| 6 | n-C₆H₁₃ | F | |
| 7 | n-C₇H₁₅ | F | |
| 8 | n-C₈H₁₇ | F | |
| 9 | c-C₃H₅ | F | |
| 10 | c-C₃H₅CH₂ | F | |
| 11 | c-C₄H₇ | F | |
| 12 | c-C₅H₇ | F | |
| 13 | c-C₅H₉ | F | |
| 14 | CH₂=CH | F | |
| 15 | CH₃CH=CH | F | |
| 16 | CH₂=CH(CH₂)₂ | F | |
| 17 | CH₃O | F | |
| 18 | C₂H₅O | F | |
| 19 | n-C₃H₇O | F | |
| 20 | n-C₄H₉O | F | |
| 21 | n-C₅H₁₁O | F | |
| 22 | CH₃ | CF₃ | |
| 23 | C₂H₅ | CF₃ | |
| 24 | n-C₃H₇ | CF₃ | Cr 112 I; Δn = 0.1672 Δε = 8.1; γ₁ = 451 |
| 25 | n-C₄H₉ | CF₃ | |
| 26 | n-C₅H₁₁ | CF₃ | |
| 27 | n-C₆H₁₃ | CF₃ | |
| 28 | n-C₇H₁₅ | CF₃ | |
| 29 | n-C₈H₁₇ | CF₃ | |
| 30 | c-C₃H₅ | CF₃ | |
| 31 | c-C₃H₅CH₂ | CF₃ | |
| 32 | c-C₄H₇ | CF₃ | |
| 33 | c-C₅H₇ | CF₃ | |
| 34 | c-C₅H₉ | CF₃ | |
| 35 | CH₂=CH | CF₃ | |
| 36 | CH₃CH=CH | CF₃ | |
| 37 | CH₂=CH(CH₂)₂ | CF₃ | |
| 38 | CH₃O | CF₃ | |
| 39 | C₂H₅O | CF₃ | |
| 40 | n-C₃H₇O | CF₃ | |
| 41 | n-C₄H₉O | CF₃ | |
| 42 | n-C₅H₁₁O | CF₃ | |
| 43 | CH₃ | OCF₃ | |
| 44 | C₂H₅ | OCF₃ | |
| 45 | n-C₃H₇ | OCF₃ | Cr 62 S₄ 78 N 85.5 I; Δn = 0.1630; Δε = 4.7; γ₁ = 366 |
| 46 | n-C₄H₉ | OCF₃ | |
| 47 | n-C₅H₁₁ | OCF₃ | |
| 48 | n-C₆H₁₃ | OCF₃ | |
| 49 | n-C₇H₁₅ | OCF₃ | |
| 50 | n-C₈H₁₇ | OCF₃ | |
| 51 | c-C₃H₅ | OCF₃ | |
| 52 | c-C₃H₅CH₂ | OCF₃ | |
| 53 | c-C₄H₇ | OCF₃ | |
| 54 | c-C₅H₇ | OCF₃ | |
| 55 | c-C₅H₉ | OCF₃ | |
| 56 | CH₂=CH | OCF₃ | |
| 57 | CH₃CH=CH | OCF₃ | |
| 58 | CH₂=CH(CH₂)₂ | OCF₃ | |
| 59 | CH₃O | OCF₃ | |
| 60 | C₂H₅O | OCF₃ | |
| 61 | n-C₃H₇O | OCF₃ | |
| 62 | n-C₄H₉O | OCF₃ | |
| 63 | n-C₅H₁₁O | OCF₃ | |

| No: 19- | R | X | Phase Range; properties |
|---|---|---|---|
| 1 | CH₃ | F | |
| 2 | C₂H₅ | F | |
| 3 | n-C₃H₇ | F | |
| 4 | n-C₄H₉ | F | |
| 5 | n-C₅H₁₁ | F | |
| 6 | n-C₆H₁₃ | F | |
| 7 | n-C₇H₁₅ | F | |
| 8 | n-C₈H₁₇ | F | |
| 9 | c-C₃H₅ | F | |
| 10 | c-C₃H₅CH₂ | F | |
| 11 | c-C₄H₇ | F | |
| 12 | c-C₅H₇ | F | |
| 13 | c-C₅H₉ | F | |
| 14 | CH₂=CH | F | |
| 15 | CH₃CH=CH | F | |
| 16 | CH₂=CH(CH₂)₂ | F | |
| 17 | CH₃O | F | |
| 18 | C₂H₅O | F | |
| 19 | n-C₃H₇O | F | |
| 20 | n-C₄H₉O | F | |
| 21 | n-C₅H₁₁O | F | |
| 22 | CH₃ | CF₃ | |
| 23 | C₂H₅ | CF₃ | |
| 24 | n-C₃H₇ | CF₃ | Cr 143 I; Δn = 0.1862; Δε = 13.7; γ₁ = 885 |
| 25 | n-C₄H₉ | CF₃ | |
| 26 | n-C₅H₁₁ | CF₃ | |
| 27 | n-C₆H₁₃ | CF₃ | |
| 28 | n-C₇H₁₅ | CF₃ | |
| 29 | n-C₈H₁₇ | CF₃ | |
| 30 | c-C₃H₅ | CF₃ | |
| 31 | c-C₃H₅CH₂ | CF₃ | |
| 32 | c-C₄H₇ | CF₃ | |
| 33 | c-C₅H₇ | CF₃ | |
| 34 | c-C₅H₉ | CF₃ | |
| 35 | CH₂=CH | CF₃ | |
| 36 | CH₃CH=CH | CF₃ | |
| 37 | CH₂=CH(CH₂)₂ | CF₃ | |
| 38 | CH₃O | CF₃ | |
| 39 | C₂H₅O | CF₃ | |
| 40 | n-C₃H₇O | CF₃ | |
| 41 | n-C₄H₉O | CF₃ | |
| 42 | n-C₅H₁₁O | CF₃ | |
| 43 | CH₃ | OCF₃ | |
| 44 | C₂H₅ | OCF₃ | |
| 45 | n-C₃H₇ | OCF₃ | |
| 46 | n-C₄H₉ | OCF₃ | |
| 47 | n-C₅H₁₁ | OCF₃ | |
| 48 | n-C₆H₁₃ | OCF₃ | |
| 49 | n-C₇H₁₅ | OCF₃ | |
| 50 | n-C₈H₁₇ | OCF₃ | |
| 51 | c-C₃H₅ | OCF₃ | |
| 52 | c-C₃H₅CH₂ | OCF₃ | |
| 53 | c-C₄H₇ | OCF₃ | |
| 54 | c-C₅H₇ | OCF₃ | |
| 55 | c-C₅H₉ | OCF₃ | |
| 56 | CH₂=CH | OCF₃ | |
| 57 | CH₃CH=CH | OCF₃ | |
| 58 | CH₂=CH(CH₂)₂ | OCF₃ | |
| 59 | CH₃O | OCF₃ | |
| 60 | C₂H₅O | OCF₃ | |
| 61 | n-C₃H₇O | OCF₃ | |
| 62 | n-C₄H₉O | OCF₃ | |
| 63 | n-C₅H₁₁O | OCF₃ | |

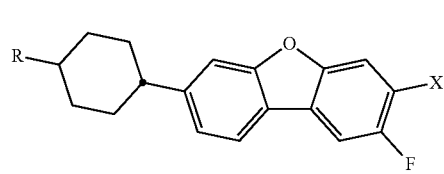

I-5-3

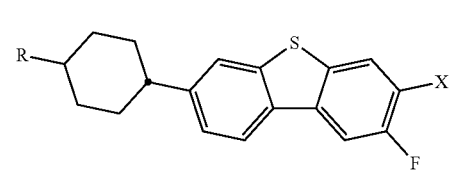

I-6-3

| No: 20- | R | X | Phase Range; properties |
|---|---|---|---|
| 1 | CH$_3$ | F | |
| 2 | C$_2$H$_5$ | F | |
| 3 | n-C$_3$H$_7$ | F | |
| 4 | n-C$_4$H$_9$ | F | |
| 5 | n-C$_5$H$_{11}$ | F | |
| 6 | n-C$_6$H$_{13}$ | F | |
| 7 | n-C$_7$H$_{15}$ | F | |
| 8 | n-C$_8$H$_{17}$ | F | |
| 9 | c-C$_3$H$_5$ | F | |
| 10 | c-C$_3$H$_5$CH$_2$ | F | |
| 11 | c-C$_4$H$_7$ | F | |
| 12 | c-C$_5$H$_7$ | F | |
| 13 | c-C$_5$H$_9$ | F | |
| 14 | CH$_2$=CH | F | |
| 15 | CH$_3$CH=CH | F | |
| 16 | CH$_2$=CH(CH$_2$)$_2$ | F | |
| 17 | CH$_3$O | F | |
| 18 | C$_2$H$_5$O | F | |
| 19 | n-C$_3$H$_7$O | F | |
| 20 | n-C$_4$H$_9$O | F | |
| 21 | n-C$_5$H$_{11}$O | F | |
| 22 | CH$_3$ | CF$_3$ | |
| 23 | C$_2$H$_5$ | CF$_3$ | |
| 24 | n-C$_3$H$_7$ | CF$_3$ | |
| 25 | n-C$_4$H$_9$ | CF$_3$ | |
| 26 | n-C$_5$H$_{11}$ | CF$_3$ | |
| 27 | n-C$_6$H$_{13}$ | CF$_3$ | |
| 28 | n-C$_7$H$_{15}$ | CF$_3$ | |
| 29 | n-C$_8$H$_{17}$ | CF$_3$ | |
| 30 | c-C$_3$H$_5$ | CF$_3$ | |
| 31 | c-C$_3$H$_5$CH$_2$ | CF$_3$ | |
| 32 | c-C$_4$H$_7$ | CF$_3$ | |
| 33 | c-C$_5$H$_7$ | CF$_3$ | |
| 34 | c-C$_5$H$_9$ | CF$_3$ | |
| 35 | CH$_2$=CH | CF$_3$ | |
| 36 | CH$_3$CH=CH | CF$_3$ | |
| 37 | CH$_2$=CH(CH$_2$)$_2$ | CF$_3$ | |
| 38 | CH$_3$O | CF$_3$ | |
| 39 | C$_2$H$_5$O | CF$_3$ | |
| 40 | n-C$_3$H$_7$O | CF$_3$ | |
| 41 | n-C$_4$H$_9$O | CF$_3$ | |
| 42 | n-C$_5$H$_{11}$O | CF$_3$ | |
| 43 | CH$_3$ | OCF$_3$ | |
| 44 | C$_2$H$_5$ | OCF$_3$ | |
| 45 | n-C$_3$H$_7$ | OCF$_3$ | |
| 46 | n-C$_4$H$_9$ | OCF$_3$ | |
| 47 | n-C$_5$H$_{11}$ | OCF$_3$ | |
| 48 | n-C$_6$H$_{13}$ | OCF$_3$ | |
| 49 | n-C$_7$H$_{15}$ | OCF$_3$ | |
| 50 | n-C$_8$H$_{17}$ | OCF$_3$ | |
| 51 | c-C$_3$H$_5$ | OCF$_3$ | |
| 52 | c-C$_3$H$_5$CH$_2$ | OCF$_3$ | |
| 53 | c-C$_4$H$_7$ | OCF$_3$ | |
| 54 | c-C$_5$H$_7$ | OCF$_3$ | |
| 55 | c-C$_5$H$_9$ | OCF$_3$ | |
| 56 | CH$_2$=CH | OCF$_3$ | |
| 57 | CH$_3$CH=CH | OCF$_3$ | |
| 58 | CH$_2$=CH(CH$_2$)$_2$ | OCF$_3$ | |
| 59 | CH$_3$O | OCF$_3$ | |
| 60 | C$_2$H$_5$O | OCF$_3$ | |
| 61 | n-C$_3$H$_7$O | OCF$_3$ | |
| 62 | n-C$_4$H$_9$O | OCF$_3$ | |
| 63 | n-C$_5$H$_{11}$O | OCF$_3$ | |

| No: 21- | R | X | Phase Range; properties |
|---|---|---|---|
| 1 | CH$_3$ | F | |
| 2 | C$_2$H$_5$ | F | |
| 3 | n-C$_3$H$_7$ | F | |
| 4 | n-C$_4$H$_9$ | F | |
| 5 | n-C$_5$H$_{11}$ | F | |
| 6 | n-C$_6$H$_{13}$ | F | |
| 7 | n-C$_7$H$_{15}$ | F | |
| 8 | n-C$_8$H$_{17}$ | F | |
| 9 | c-C$_3$H$_5$ | F | |
| 10 | c-C$_3$H$_5$CH$_2$ | F | |
| 11 | c-C$_4$H$_7$ | F | |
| 12 | c-C$_5$H$_7$ | F | |
| 13 | c-C$_5$H$_9$ | F | |
| 14 | CH$_2$=CH | F | |
| 15 | CH$_3$CH=CH | F | |
| 16 | CH$_2$=CH(CH$_2$)$_2$ | F | |
| 17 | CH$_3$O | F | |
| 18 | C$_2$H$_5$O | F | |
| 19 | n-C$_3$H$_7$O | F | |
| 20 | n-C$_4$H$_9$O | F | |
| 21 | n-C$_5$H$_{11}$O | F | |
| 22 | CH$_3$ | CF$_3$ | |
| 23 | C$_2$H$_5$ | CF$_3$ | |
| 24 | n-C$_3$H$_7$ | CF$_3$ | |
| 25 | n-C$_4$H$_9$ | CF$_3$ | |
| 26 | n-C$_5$H$_{11}$ | CF$_3$ | |
| 27 | n-C$_6$H$_{13}$ | CF$_3$ | |
| 28 | n-C$_7$H$_{15}$ | CF$_3$ | |
| 29 | n-C$_8$H$_{17}$ | CF$_3$ | |
| 30 | c-C$_3$H$_5$ | CF$_3$ | |
| 31 | c-C$_3$H$_5$CH$_2$ | CF$_3$ | |
| 32 | c-C$_4$H$_7$ | CF$_3$ | |
| 33 | c-C$_5$H$_7$ | CF$_3$ | |
| 34 | c-C$_5$H$_9$ | CF$_3$ | |
| 35 | CH$_2$=CH | CF$_3$ | |
| 36 | CH$_3$CH=CH | CF$_3$ | |
| 37 | CH$_2$=CH(CH$_2$)$_2$ | CF$_3$ | |
| 38 | CH$_3$O | CF$_3$ | |
| 39 | C$_2$H$_5$O | CF$_3$ | |
| 40 | n-C$_3$H$_7$O | CF$_3$ | |
| 41 | n-C$_4$H$_9$O | CF$_3$ | |
| 42 | n-C$_5$H$_{11}$O | CF$_3$ | |
| 43 | CH$_3$ | OCF$_3$ | |
| 44 | C$_2$H$_5$ | OCF$_3$ | |
| 45 | n-C$_3$H$_7$ | OCF$_3$ | |
| 46 | n-C$_4$H$_9$ | OCF$_3$ | |
| 47 | n-C$_5$H$_{11}$ | OCF$_3$ | |
| 48 | n-C$_6$H$_{13}$ | OCF$_3$ | |
| 49 | n-C$_7$H$_{15}$ | OCF$_3$ | |
| 50 | n-C$_8$H$_{17}$ | OCF$_3$ | |
| 51 | c-C$_3$H$_5$ | OCF$_3$ | |
| 52 | c-C$_3$H$_5$CH$_2$ | OCF$_3$ | |
| 53 | c-C$_4$H$_7$ | OCF$_3$ | |
| 54 | c-C$_5$H$_7$ | OCF$_3$ | |
| 55 | c-C$_5$H$_9$ | OCF$_3$ | |
| 56 | CH$_2$=CH | OCF$_3$ | |
| 57 | CH$_3$CH=CH | OCF$_3$ | |
| 58 | CH$_2$=CH(CH$_2$)$_2$ | OCF$_3$ | |
| 59 | CH$_3$O | OCF$_3$ | |
| 60 | C$_2$H$_5$O | OCF$_3$ | |
| 61 | n-C$_3$H$_7$O | OCF$_3$ | |
| 62 | n-C$_4$H$_9$O | OCF$_3$ | |
| 63 | n-C$_5$H$_{11}$O | OCF$_3$ | |

Use Examples

A nematic liquid-crystal mixture N-1 having the composition and properties as indicated in the following table is prepared.

| Mixture N-1 | | | |
|---|---|---|---|
| BCH-3F.F | 12.0% | T(N, I) = | 92 °C. |
| BCH-5F.F | 10.0% | Δn (20° C., 589.3 nm) = | 0.0969 |
| ECCP-30CF3 | 5.0% | Δε (20° C., 1 kHz) = | 5.2 |
| ECCP-50CF3 | 5.0% | $\gamma_1$ (20° C.) = | 134 mPa·s |
| CBC-33F | 2.0% | | |
| CBC-53F | 2.0% | | |
| CBC-55F | 2.0% | | |
| PCH-6F | 8.0% | | |
| PCH-7F | 6.0% | | |
| CCP-20CF3 | 8.0% | | |
| CCP-30CF3 | 12.0% | | |
| CCP-40CF3 | 7.0% | | |
| CCP-50CF3 | 11.0% | | |
| PCH-5F | 10.0% | | |
| Σ | 100.0% | | |

A nematic liquid-crystal medium M-1 consisting of 90% of the medium N-1 and 10% of the compound of Synthesis Example 1 (compound (1)) has the following properties:

| N-1 | 90.0% | T(N, I) = | 90 °C. |
|---|---|---|---|
| (1) | 10.0% | Δn (20° C., 589.3 nm) = | 0.1075 |
| Σ | 100.0% | Δε (20° C., 1 kHz) = | 6.6 |
| | | $\gamma_1$ (20° C.) = | 150 mPa·s |

The compound (1) is well soluble in the medium N-1. The addition of the compound (1) according to the invention to the medium N-1 has the effect that the dielectric anisotropy is advantageously increased.

A nematic liquid-crystal medium M-2 consisting of 95% of the medium N-1 and 5% of the compound of Synthesis Example (2) (compound (2)) has the following properties:

| N-1 | 95.0% | T(N, I) = | 92.8 °C. |
|---|---|---|---|
| (2) | 5.0% | Δn (20° C., 589.3 nm) = | 0.1026 |
| Σ | 100.0% | Δε (20° C., 1 kHz) = | 6.2 |
| | | $\gamma_1$ (20° C.) = | 143 mPa·s |

The compound (2) is well soluble in the medium N-1. The addition of the compound (2) according to the invention to the medium N-1 has the effect that the dielectric anisotropy is advantageously increased.

The invention claimed is:

1. A compound of formula I

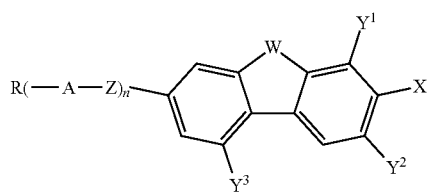

in which

W denotes O or S

R denotes H, an alkyl radical having 1 to 15 C atoms, wherein one or more $CH_2$ groups in these radicals may each be replaced, independently of one another, by —C≡C—, —$CF_2$O—, —O$CF_2$—, —CH=CH—,

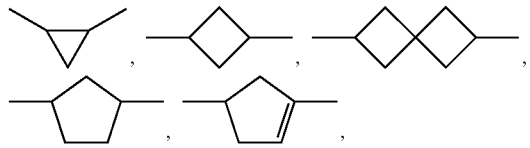

—O—, —CO—O— or —O—CO— in such a way that 0 atoms are not linked directly to one another, and in which one or more H atoms may be replaced by halogen, A on each occurrence, identically or differently, denotes a radical selected from the following groups:
a) the group consisting of trans-1,4-cyclohexylene, 1,4-cyclohexenylene, and decaline-2,6-diyl, in which one or more non-adjacent $CH_2$ groups may be replaced by —O— and/or —S— and in which one or more H atoms may be replaced by F,
b) the group consisting of 1,4-phenylene and 2,6-naphthylene, in which one or two CH groups may be replaced by N and in which, in addition, one or more H atoms may be replaced by L,
c) the group consisting of 1,3-dioxane-2,5-diyl, tetrahydrofuran-2,5-diyl, cyclobutane-1,3-diyl, thiophene-2,5-diyl, selenophene-2,5-diyl, and 1,2,3,4-tetrahydronanaphthaline-2,6-diyl, each of which may be mono- or polysubstituted by L,
d) the group consisting of bicyclo[1.1.1]pentane-1,3-diyl, bicyclo[2.2.2]octane-1,4-diyl, and spiro[3.3]heptane-2,6-diyl, in which one or more H atoms may be replaced by F, L on each occurrence, identically or differently, denotes halogen, cyano, alkyl, alkoxy, alkylcarbonyl or alkoxycarbonyl group with 1 to 7 C atoms, wherein one or more H atoms may be substituted by F or Cl, Z on each occurrence, identically or differently, denotes a single bond, —$CF_2$O—, —O$CF_2$—, —$CH_2CH_2$—, —$CF_2CF_2$—,
—C(O)O—, —OC(O)—, —$CH_2$O—, —O$CH_2$—, —CF=CH—, —CH=CF—, —CF=CF—, —CH=CH— or —C≡C—, $Y^1$ and $Y^2$ denote F and $Y^3$ denotes H, X denotes $OCF_3$ or $CF_3$ and n is 0, 1 or 2, wherein the compound has positive dielectric anosotropy.

2. The compound according to claim 1 selected from the following sub-formulae:

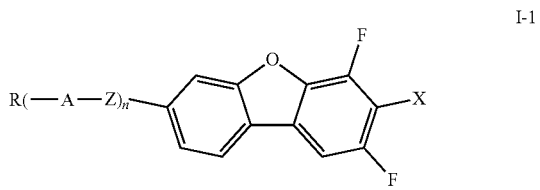

-continued

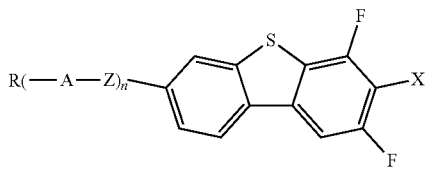

I-2 in which R, A, Z, X and n have the meanings given in claim 1.

3. The compound according to claim 1, wherein Z denotes a single bond.

4. The compound according to claim 1, wherein n is 1 and A denotes trans-1,4-cyclohexylene or 1,4-cyclohexenylene.

5. A compound of formula P or P′

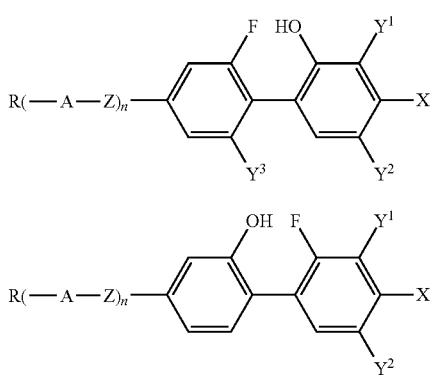

in which

R denotes H, an alkyl radical having 1 to 15 C atoms, wherein one or more $CH_2$ groups in these radicals may each be replaced, independently of one another, by —C≡C—, —$CF_2$O—, —O$CF_2$—, —CH=CH—,

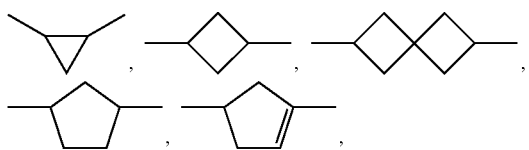

—O—, —CO—O— or —O—CO— in such a way that O atoms are not linked directly to one another, and in which one or more H atoms may be replaced by halogen, A on each occurrence, identically or differently, denotes a radical selected from the following groups:

a) the group consisting of trans-1,4-cyclohexylene, 1,4-cyclohexenylene, and decaline-2,6-diyl, in which one or more non-adjacent $CH_2$ groups may be replaced by —O— and/or —S— and in which one or more H atoms may be replaced by F, b) the group consisting of 1,4-phenylene and 2,6-naphthylene, in which one or two CH groups may be replaced by N and in which, in addition, one or more H atoms may be replaced by L, c) the group consisting of 1,3-dioxane-2,5-diyl, tetrahydrofuran-2,5-diyl, cyclobutane-1,3-diyl, thiophene-2,5-diyl, selenophene-2,5-diyl, and 1,2,3,4-tetrahydronanaphthaline-2,6-diyl, each of which may be mono- or polysubstituted by L, d) the group consisting of bicyclo[1.1.1]pentane-1,3-diyl, bicyclo[2.2.2]octane-1,4-diyl, and spiro[3.3]heptane-2,6-diyl, in which one or more H atoms may be replaced by F, L on each occurrence, identically or differently, denotes halogen, cyano, alkyl, alkoxy, alkylcarbonyl or alkoxycarbonyl group with 1 to 7 C atoms, wherein one or more H atoms may be substituted by F or Cl, Z on each occurrence, identically or differently, denotes a single bond, —$CF_2$O—, —O$CF_2$—, —$CH_2CH_2$—, —$CF_2CF_2$—, —C(O)O—, —OC(O)—, —$CH_2$O—, —O$CH_2$—, —CF=CH—, —CH=CF—, —CF=CF—, —CH=CH— or —C≡C—, $Y^1$ and $Y^2$ denote F and $Y^3$ denotes H, X denotes $OCF_3$ or $CF_3$, n is 0, 1 or 2.

6. A process for the preparation of a compound of formula I of claim 1, treating a compound of formula P or P′

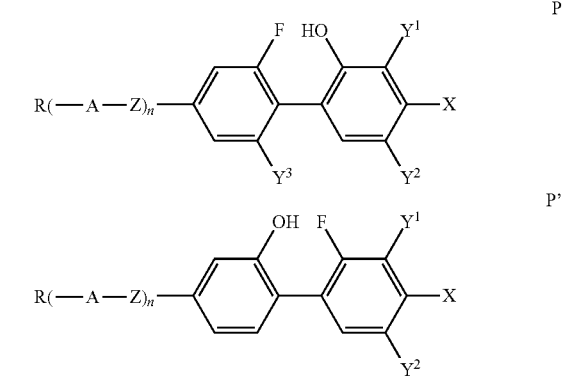

wherein R, A, Z, n, X, $Y^1$, $Y^2$ and $Y^3$ are defined as in formula I with a base.

7. A liquid-crystalline medium comprising one or more compounds of formula I according to claim 1.

8. The liquid-crystalline medium according to claim 7, wherein the medium comprises one or more compounds selected from the group of compounds of formulae II and III

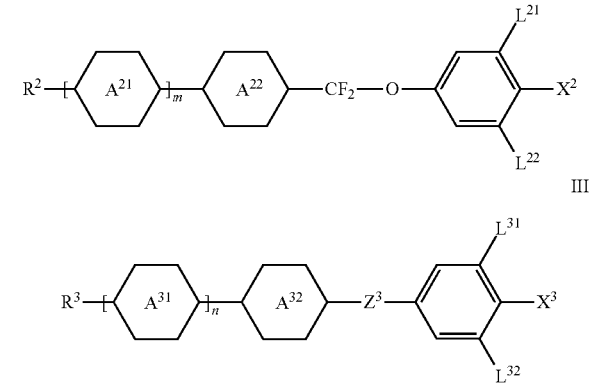

in which $R^2$ denotes alkyl, alkoxy, fluorinated alkyl or fluorinated alkoxy having 1 to 7 C atoms, alkenyl, alkenyloxy, alkoxyalkyl or fluorinated alkenyl having 2 to 7 C atoms,

71

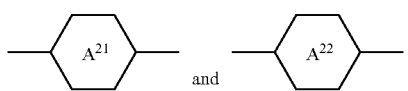

on each appearance, independently of one another, denote

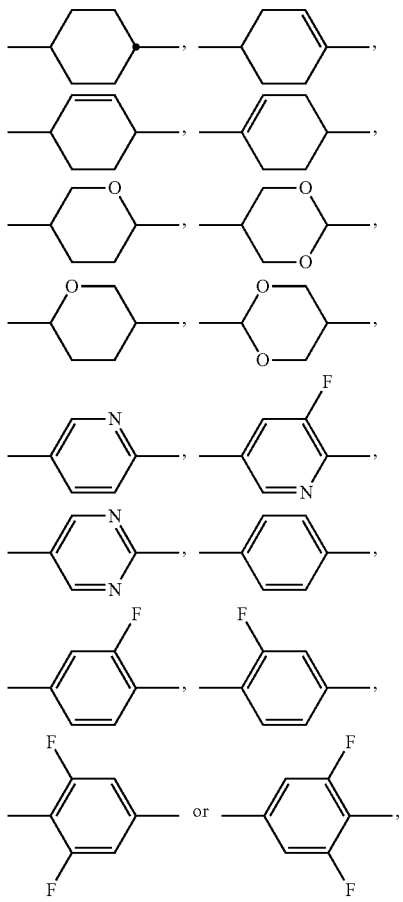

$L^{21}$ and $L^{22}$ denote H or F, $X^2$ denotes halogen, halogenated alkyl or alkoxy having 1 to 3 C atoms or halogenated alkenyl or alkenyloxy having 2 or 3 C atoms, m denotes 0, 1, 2 or 3;

$R^3$ denotes alkyl, alkoxy, fluorinated alkyl or fluorinated alkoxy having 1 to 7 C atoms, alkenyl, alkenyloxy, alkoxyalkyl or fluorinated alkenyl having 2 to 7 C atoms

72

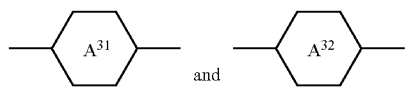

on each appearance, independently of one another, are

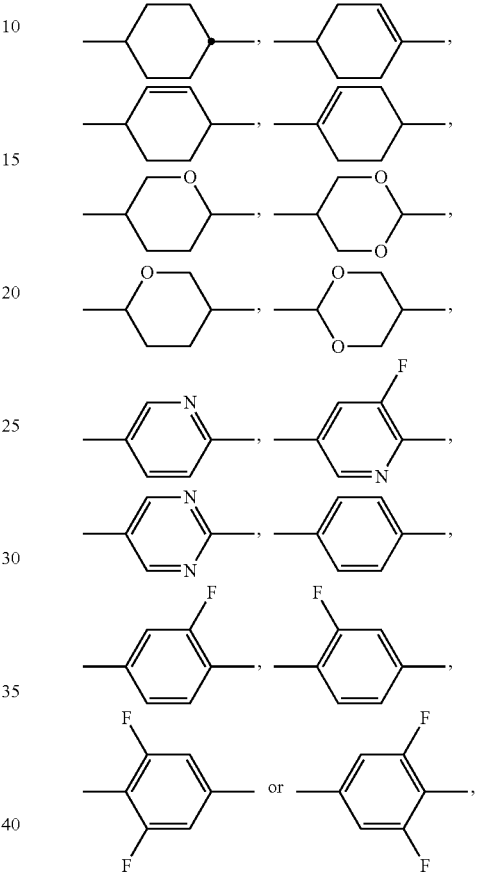

$L^{31}$ and $L^{32}$, independently of one another, denote H or F, $X^3$ denotes halogen, halogenated alkyl or alkoxy having 1 to 3 C atoms or halogenated alkenyl or alkenyloxy having 2 or 3 C atoms, $Z^3$ denotes —$CH_2CH_2$—, —$CF_2CF_2$—, —COO—, trans-CH=CH—, trans-CF=CF—,
—$CH_2O$— or a single bond, and n is 0, 1, 2 or 3.

9. Electro-optical display element containing a liquid-crystalline medium according to claim 7.

10. The display element according to claim 9, wherein the display element is a TN-TFT, IPS or FFS display.

* * * * *